(12) United States Patent
Strittmatter et al.

(10) Patent No.: US 9,217,036 B2
(45) Date of Patent: Dec. 22, 2015

(54) PRION PROTEIN AS A RECEPTOR FOR AMYLOID-β OLIGOMERS

(75) Inventors: Stephen M. Strittmatter, Guilford, CT (US); Juha Lauren, New Haven, CT (US); David Gimbel, New Haven, CT (US)

(73) Assignee: YALE UNIVERSITY, New Haven, CT (US)

( * ) Notice: Subject to any disclaimer, the term of this patent is extended or adjusted under 35 U.S.C. 154(b) by 1080 days.

(21) Appl. No.: 12/597,535

(22) PCT Filed: Apr. 28, 2008

(86) PCT No.: PCT/US2008/005427
§ 371 (c)(1),
(2), (4) Date: Feb. 16, 2010

(87) PCT Pub. No.: WO2008/134034
PCT Pub. Date: Nov. 6, 2008

(65) Prior Publication Data
US 2010/0291090 A1    Nov. 18, 2010

Related U.S. Application Data
(60) Provisional application No. 60/926,605, filed on Apr. 26, 2007.

(51) Int. Cl.
*C07K 16/28* (2006.01)
*A61K 39/00* (2006.01)

(52) U.S. Cl.
CPC ....... *C07K 16/2872* (2013.01); *A61K 2039/505* (2013.01); *C07K 2317/34* (2013.01); *C07K 2317/76* (2013.01)

(58) Field of Classification Search
CPC ........... C07K 14/4711; C07K 2317/33; A61K 2039/505; G01N 33/6896; G01N 2800/2821; G01N 2333/4709; G01N 33/5008
See application file for complete search history.

(56) References Cited

U.S. PATENT DOCUMENTS

2003/0087407 A1    5/2003    Soto-Jara et al.
2005/0222036 A1   10/2005    During et al.

FOREIGN PATENT DOCUMENTS

WO    WO 2009/018625 A1    2/2009

OTHER PUBLICATIONS

Pankiewicz et al. Clearance and prevention of prion infection in cell culture by anti-PrP antibodies. Eur J Neurosci. May 2006;23(10):2635-47.*
Zeisel et al. Non-pharmacological Treatment for Alzheimer's Disease: A mind-brain approach. Non-pharmacological Treatment for Alzheimer's. Mar. 1999, p. 1-16.*
Westergard et al. The cellular prion protein (PrPc): Its physiological function and role in disease. Biochim Biophys Acta. Jun. 2007; 1772(6): 629-644.*
Hirsch et al. PrPc signalling in neurons: From basics to clinical challenges. Biochimie, in press, available online (Jun. 18, 2014) pp. 1-10.*
Hampel et al. The future of Alzheimer's disease: the next 10 years. Prog Neurobiol. Dec. 2011;95(4):718-28.*
Vickers. A vaccine against Alzheimer's disease: developments to date. Drugs Aging. 2002;19(7):487-94. Review.*
Perrin et al. Multimodal techniques for diagnosis and prognosis of Alzheimer's disease. Nature. Oct. 15, 2009;461(7266):916-22.*
Golabek et al. Abstract Only. Amyloid beta binding proteins in vitro and in normal human cerebrospinal fluid. Neurosci Lett. May 19, 1995;191(1-2):79-82.*
Parkin, et al., "Cellular prion protein regulates β-secretase cleavage of the Alzheimer's amyloid precursor protein," *PNAS* 104(26):11062-11067, The National Academy of Sciences of the USA, United States (2007).
Yehiely, F., et al., "Identification of Candidate Proteins Binding to Prion Protein," *Neurobiology of Disease* 3:339-355, Academic Press, United States (1997).
Baumann, F., et al., "Lethal recessive myelin toxicity of prion protein lacking its central domain," *EMBO J.* 26:538-547, Nature Publishing Group, United Kingdom (Jan. 2007).
Büeler, H., et al., "Normal development and behaviour of mice lacking the neuronal cell-surface PrP protein," *Nature* 356: 577-582, Nature Publishing Group, United Kingdom (1992).
Chapman, P., et al., "Impaired synaptic plasticity and learning in aged amyloid precursor protein transgenic mice," *Nat. Neurosci.* 2: 271-276, Nature Publishing Group, United States (1999).
Chen, G.,et al., "A learning deficit related to age and β-amyloid plaques in a mouse model of Alzheimer's disease," *Nature* 408: 975-979, Nature Publishing Group, United Kingdom (2000).
Chromy, B., et al., "Self-Assembly of $a\beta_{1-42}$ into Globular Neurotoxins," *Biochemistry* 42:12749-12760, American Chemical Society, United States (2003).
Cleary, J., et al., "Natural oligomers of the amyloid-β protein specifically disrupt cognitive function," *Nat. Neurosci.* 8:79-84, Nature Publishing Group, United States (2005).
Fournier, A., et al., "Identification of a receptor mediating Nogo-66 inhibition of axonal regeneration," *Nature* 409: 341-346, Nature Publishing Group, United Kingdom (2001).
Haass, C. and Selkoe, D.J., "Soluble protein oligomers in neurodegeneration: lessons from the Alzheimer's amyloid β-peptide," *Nat. Rev. Mol. Cell Biol.* 8:101-112, Nature Publishing Group, United Kingdom (Feb. 2007).

(Continued)

*Primary Examiner* — Michelle S Horning
(74) *Attorney, Agent, or Firm* — Sterne, Kessler, Goldstein & Fox, P.L.L.C.

(57) ABSTRACT

The invention provides methods of inhibiting suppression of long term potentiation, improving acute memory retention and spatial memory performance and treating Alzheimer's disease by administration of a PrPc antagonist or combinations thereof. Additionally, this invention provides pharmaceutical kits comprising, and methods for making and using, such combinations, as well as methods of identifying molecules that could function as $PrP^c$ antagonists.

28 Claims, 7 Drawing Sheets

(56) References Cited

OTHER PUBLICATIONS

Hardy, J. and Selkoe, D.J., "The Amyloid Hypothesis of Alzheimer's disease: Progress and Problems on the Road to Therapeutics," *Science* 297:353-356, American Association for the Advancement of Science, United States (2002).
Jankowsky, J., et al., "Mutant presenilins specifically elevate the levels of the 42 residue β-amyloid peptide in vivo: evidence for augmenation of a 42-specific γ secretase," *Hum. Mol. Genet.* 13:159-170, IRL Press at Oxford University Press, United Kingdom (2004).
Knobloch, M., et al., "Aβ Oligomer-Mediated Long-Term Potentiation Impairment Involves Protein Phosphatase 1-Dependent Mechanisms," *J. Neurosci.* 27:7648-7653, Society for Neuroscience, United States (Jul. 2007).
Lacor, P., et al.,"Aβ Oligomer-Induced Aberrations in Synapse Composition, Shape, and Density Provide a Molecular Basis for Loss of Connectivity in Alzheimer's disease," *J. Neurosci.* 27:796-807, Society for Neuroscience, United States (Jan. 2007).
Lacor, P., et al., "Synaptic Targeting by Alzheimer's-Related Amyloid β Oligomers," *J. Neurosci.* 24:10191-10200, Society for Neuroscience, United States (2004).
Lee, J., et al., "Nogo Receptor Antagonism Promotes Stroke Recovery by Enhancing Axonal Plasticity," *J. Neurosci.* 24:6209-6217, Society for Neuroscience, United States (2004).
Lesné, S., et al., "A specific amyloid-β protein assembly in the brain impairs memory," *Nature* 440:352-357, Nature Publishing Group, United Kingdom (Mar. 2006).
Li, A., et al., "Neonatal lethality in transgenic mice expressing prion protein with a deletion of residues 105-125," *EMBO J.* 26:548-558, Nature Publishing Group, United Kingdom (Jan. 2007).
Lledo, P.-M., et al., "Mice deficient for prion protein exhibit normal neuronal excitability and synaptic transmission in the hippocampus," *Proc. Natl. Acad. Sci. U.S.A.* 93:2403-2407, National Academy of Sciences, United States (1996).
Manson, J., et al., "129/Ola Mice Carrying a Null Mutation in PrP that abolishes mRNA Production are Developmentally Normal," *Mol. Neurobiol.* 8:121-127, Humana Press, United States (1994).
Park, J., et al., "Subcutaneous Nogo Receptor Removes Brain Amyloid-β and Improves Spatial Memory in Alzheimer's Transgenic Mice," *J. Neurosci.* 26:13279-13286, Society for Neuroscience, United States (Dec. 2006).
Park, J., et al., "Alzheimer Precursor Protein Interaction with the Nogo-66 Receptor Reduces Amyloid-β Plaque Deposition," *J. Neurosci.* 26:1386-1395, Society for Neuroscience, United States (Feb. 2006).
Prusiner, S., "Prions," *Proc. Natl. Acad. Sci. U.S.A.* 95:13363-13383, National Academy of Sciences, United States (1998).
Rajagopalan, S., et al., "Neogenin mediates the action of repulsive guidance molecule," *Nat. Cell Biol.* 6: 756-762, Macmillan Magazines Ltd., United Kingdom (2004).
Riek, R., et al., NMR structure of the mouse prion protein domain PrP(121-231), *Nature* 382:180-82, Nature Publishing Group, United Kingdom (1996).
Shankar, G., et al., "Natural Oligomers of the Alzheimer Amyloid-β Protein Induce Reversible Synapse Loss by Modulating an NMDA-Type Glutamate Receptor-Dependent Signaling Pathway," *J. Neurosci.* 27:2866-2875, Society for Neuroscience, United States (Mar. 2007).
Solforosi, L., et al., "Cross-Linking Cellular Prion Protein Triggers Neuronal Apoptosis in Vivo," *Science* 303: 1514-1516, American Association for the Advancement of Science, United States (2004).
Viles, J., et al., "Copper binding to the prion protein: Structural implications of four identical cooperative binding sites," *Proc. Natl. Acad. U.S.A.* 96:2042-47, National Academy of Sciences, United States (1999).
Walsh, D., et al., "Naturally secreted oligomers of amyloid β protein potently inhibit hippocampal long-term potentiation in vivo," *Nature* 416:535-539, Nature Publishing Group, United Kingdom (2002).
Wang, X., et al., "Delayed Nogo Receptor Therapy Improves Recovery from Spinal Cord Contusion," *Ann. Neurol.* 60:540-549, Wiley-Liss, United States (Nov. 2006).
International Search Report for International Application No. PCT/US08/05427, mailed on Sep. 19, 2008, ISA/US, Alexandria, Virginia, United States.
Chung E., et al., "Anti-PrP$^c$ monoclonal antibody infusion as a novel treatment for cognitive deficits in an alzheimer's disease model mouse," *BMC Neuroscience* 11:130, BioMed Central Ltd., United Kingdom (2010).
Dermaut, B., et al., "PRNP Val129 Homozygosity Increases Risk for Early Onset Alzheimer's Disease," *Ann. Neurol.* 53:409-12, Wiley-Liss, Inc., United States(2003).
Filesi, I., et al., "Selective re-routing of prion protein to proteasomes and alteration of its vesicular secretion prevent PrP$^{Sc}$ formation," *J. Neurochemistry* 101:1516-26, Int'l Society for Neurochemistry, United Kingdom (2007).
McNeill, A., "A Molecular Analysis of Prion Protein Expression in Alzheimer's Disease," *McGill J. Medicine* 8:7-14, MJM, Canada (2004).
Pankiewicz, J., et al., "Clearance and prevention of prion infection in cell culture by anti-PrP antibodies," *Eur. J. Neurosci.* 23:2635-47, Federation of European Neuroscience Societies and Blackwell Publishing, Ltd., United Kingdom (2006).
Schwarze-Eicker, K., et al., "Prion protein (PrP$^c$) promotes B-amyloid plaque formation," *Neurobiology of Aging* 26:1 177-82, Elsevier Inc., United States (2005).
White, A.R., et al., "Monoclonal antibodies inhibit prion replication and delay the development of prion disease," *Nature* 422:80-83, Nature Publishing Group, United Kingdom (2003).
International Preliminary Report on Patentability for International Application No. PCT/US2008/005427, issued Oct. 27, 2009, International Bureau, Geneva, Switzerland.
Supplementary European Search Report for European Application No. EP 08743351, completed Dec. 9, 2011, EPO, The Hague, Netherlands.
Freir D.B., et al., "Interaction between prion protein and toxic amyloid β assemblies can be therapeutically targeted at multiple sites," *Nature Communications* 2:336:1-9, Macmillian Publishers Ltd., United States (2011).

* cited by examiner

PRION PROTEIN AS A RECEPTOR FOR AMYLOID-β OLIGOMERS

This application is the National Stage of International Application Number PCT/US2008/005427, filed Apr. 28, 2008, which claims the benefit of U.S. Provisional Application No. 60/926,605, filed Apr. 26, 2007, all of which are incorporated by reference herein.

REFERENCE TO A SEQUENCE LISTING SUBMITTED ELECTRONICALLY VIA EFS-WEB

The content of the electronically submitted sequence listing (Name: sequencelisting_ascii.txt, Size: 19,835 bytes; and Date of Creation: Jun.12, 2012) is herein incorporated by reference in its entirety.

BACKGROUND OF THE INVENTION

1. Field of the Invention

This invention relates to neurobiology and molecular biology. More particularly, this invention relates to methods for inhibiting suppression of long term potentiation, improving or increasing acute memory retention or spatial memory performance, and treating Alzheimer's disease by administering antagonists of $PrP^c$, including $PrP^c$ soluble polypeptides, anti-$PrP^c$ antibodies and antigen-binding fragments thereof, soluble and fusion proteins thereof, and $PrP^c$ antagonist polynucleotides or aptamers. This invention further relates to pharmaceutical kits comprising, and methods for making and using, such combinations, as well as methods of identifying molecules that could function as $PrP^c$ antagonists.

2. Background Art

A pathological hallmark of Alzheimer's disease (AD) is an accumulation of insoluble plaque containing the amyloid-β peptide (Aβ) of 40-42 aa residues. Hardy & Selkoe, *Science* 297:353-356 (2002). Dementia in familial and sporadic AD is correlated with elevated concentrations of soluble Aβ42. Prefibrillar, soluble oligomers of Aβ have been recognized to be early and key intermediates in AD-related synaptic dysfunction. Lesne, et al., *Nature* 440:352-357 (2006); Haass & Selkoe, *Nat Rev Mol Cell Biol* 8: 101-112 (2007); Cleary et al., *Nat Neurosci* 8, 79-84 (2005); Chromy et al., *Biochemistry* 42: 12749-12760 (2003); Lacor et al., *J Neurosci* 27: 796-807 (2007); Lacor et al., *J Neurosci* 24: 10191-10200 (2004); Walsh et al., *Nature* 416: 535-539 (2002); Shankar, et al., *J Neurosci* 27: 2866-2875 (2007). At nanomolar concentrations, soluble Aβ-oligomers block long-term potentiation in hippocampal slices (Walsh et al., *Nature* 416: 535-539 (2002)) cause dendritic spine retraction from pyramidal cells (Lacor et al., *J Neurosci* 27: 796-807 (2007); Shankar, et al., *J Neurosci* 27: 2866-2875 (2007)) and impair rodent spatial memory (Lesne, et al., *Nature* 440:352-357 (2006)). Highly potent, soluble Aβ-oligomers have been prepared from chemical syntheses, from transfected cell culture supernatants, from transgenic mouse brain and from human AD brain. Lesne, et al., *Nature* 440:352-357 (2006); Chromy et al., *Biochemistry* 42: 12749-12760 (2003); Walsh et al., *Nature* 416: 535-539 (2002). Together, these data imply a high affinity cell surface receptor for soluble Aβ-oligomers on neurons, one that it is central to the pathophysiological process in AD.

While previous studies have provided direct evidence for the existence of a disease-mediating receptor, its identity has remained unknown. Here, we utilize expression cloning to reveal the cellular prion protein $PrP^c$ (hereinafter $PrP^c$) as a high affinity receptor for Aβ-oligomers. Moreover, Aβ binds to a domain of $PrP^c$ which is implicated in neurodegeneration (Baumann, et al., *EMBO J* 26: 538-547 (2007); Li et al. *EMBO J* 26: 548-558 (2007)), and $PrP^c$ is required for Aβ-oligomer-induced synaptic dysfunction in vitro and in vivo. The identification of $PrP^c$ as a synapto-toxic receptor for the Aβ42-oligomers of Alzheimer's disease provides a novel site for the development of therapeutics designed to relieve Alzheimer's disease symptoms. Pharmaceutical compounds targeting $PrP^c$ may have higher specificity for the alleviation of synaptic dysfunction than those directed against other molecular targets.

BRIEF SUMMARY OF THE INVENTION

Although methods and materials similar or equivalent to those described herein can be used in the practice or testing of the invention, the preferred methods and materials are described below. The materials, methods and examples are illustrative only, and are not intended to be limiting. Other features and advantages of the invention will be apparent from the detailed description and from the claims.

In some embodiments, the invention is directed to a method of inhibiting suppression of long term potentiation in a mammal comprising administering a therapeutically effective amount of a $PrP^c$ antagonist. In further embodiments, the invention is directed to a method of improving or increasing acute memory retention or spatial memory performance in a mammal comprising administering a therapeutically effective amount of a $PrP^c$ antagonist. In other embodiments, the invention is directed to a method of treating Alzheimer's disease comprising administering a therapeutically effective amount of a $PrP^c$ antagonist. In certain embodiments, the mammal is a human.

In various embodiments of the above methods, the antagonist is selected from the group consisting of (i) a soluble $PrP^c$ polypeptide; (ii) a $PrP^c$ antagonist polynucleotide; (iii) a anti-$PrP^c$ antibody or fragment thereof; (iv) a $PrP^c$ aptamer; and (v) a combination of two or more of said $PrP^c$ antagonists.

Certain soluble $PrP^c$ polypeptides include, but are not limited to, a soluble $PrP^c$ polypeptide or an active variant, fragment or derivative thereof comprising amino acid residues X to Y of SEQ ID NOs: 2, 4 or 6 wherein X=20-25 and Y=225-235; amino acid residues $X_1$ to $Y_1$ of SEQ ID NOs: 2, 4 or 6 wherein $X_1$=90-100 and $Y_1$=105-115; amino acid residues $X_2$ to $Y_2$ of SEQ ID NOs: 2, 4 or 6 wherein $X_2$=25-40 and $Y_2$=100-112; amino acid residues $X_2$ to $Y_2$ of SEQ ID NOs: 2, 4 or 6, wherein $Y_3$ is any interger from 120-130.

Certain soluble $PrP^c$ polypeptides include, but are not limited to, soluble PrPc polypeptide that are 90% identical to a reference amino acid sequence selected from the group consisting of: (i) amino acids 95-110 of SEQ ID NOs:2, 4 or 6; (ii) amino acids 32 to 121 of SEQ ID NOs:2, 4 or 6; (iii) amino acids 32 to 106 of SEQ ID NOs:2, 4 or 6; (iv) amino acids 23 to 230 of SEQ ID NOs:2, 4 or 6; and (v) a combination of one ore more of said reference amino acid sequences. In certain embodiments, the soluble PrPc polypeptide is selected from the group consisting of: (i) amino acids 95-110 of SEQ ID NOs:2, 4 or 6; (ii) amino acids 32 to 121 of SEQ ID NOs:2, 4 or 6; (iii) amino acids 32 to 106 of SEQ ID NOs:2, 4 or 6;(iv) amino acids 22 to 231 of SEQ ID NOs:2, 4 or 6; (v) variants or derivatives of any of said polypeptide fragments; and (vi) a combination of at least two of said polypeptide fragments or variants or derivatives thereof. In one embodiment, the soluble $PrP^c$ polypeptide is amino acids 95-110 of SEQ ID NOs:2, 4 or 6. In another embodiment, the soluble PrPc polypeptide is amino acids 32 to 121 of SEQ ID NOs:2, 4 or 6. In a further embodiment, the soluble $PrP^c$ polypeptide is amino acids 32 to 106 of SEQ ID NOs:2, 4 or 6. In a still further embodiment, the soluble PrP$^c$ polypeptide is amino acids 22 to 231 of SEQ ID NOs:2, 4 or 6.

In some embodiments, the soluble PrP$^c$ polypeptide is cyclic. In some embodiments, the cyclic polypeptides further comprise a first molecule linked at the N-terminus and a second molecule linked at the C-terminus; wherein the first molecule and the second molecule are joined to each other to form said cyclic molecule. In some embodiments, the first and second molecules are selected from the group consisting of: a biotin molecule, a cysteine residue, and an acetylated cysteine residue. In some embodiments, the first molecule is a biotin molecule attached to the N-terminus and the second molecule is a cysteine residue attached to the C-terminus of the polypeptide of the invention. In some embodiments, the first molecule is an acetylated cysteine residue attached to the N-terminus and the second molecule is a cysteine residue attached to the C-terminus of the polypeptide of the invention. In some embodiments, the first molecule is an acetylated cysteine residue attached to the N-terminus and the second molecule is a cysteine residue attached to the C-terminus of the polypeptide of the invention. In some embodiments, the C-terminal cysteine has an NH2 moiety attached.

In some embodiments, the soluble PrP$^c$ polypeptide further comprises a non-PrP$^c$ moiety. In some embodiments, the non-PrP$^c$ moiety is a heterologous polypeptide fused to the soluble PrP$^c$ polypeptide. In some embodiments, the heterologous polypeptide is selected from the group consisting of an immunoglobulin fragment, serum albumin, a targeting protein, a reporter protein, and a purification-facilitating protein. In some embodiments, the antibody Ig polypeptide is a hinge and Fc polypeptide.

In some embodiments, the polypeptides and antibodies used in the methods of the present invention are conjugated to a polymer. In some embodiments, the polymer is selected from the group consisting of a polyalkylene glycol, a sugar polymer, and a polypeptide. In some embodiments, the polyalkylene glycol is polyethylene glycol (PEG). In some embodiments, the polypeptides and antibodies of the present invention are conjugated to 1, 2, 3 or 4 polymers. In some embodiments, the total molecular weight of the polymers is from 5,000 Da to 100,000 Da.

In some embodiments, the PrP$^c$ antagonist comprises an anti-PrP$^c$ antibody, or antigen-binding fragment thereof. In certain embodiments, the anti-PrP$^c$ antibody or antigen-binding fragment thereof specifically binds to an epitope consisting essentially of a polypeptide fragment selected from the group consisting of: (i) amino acids 95 to 110 of SEQ ID NOs:2, 4 or 6; (ii) amino acids 32 to 121 of SEQ ID NOs:2, 4 or 6; (iii) amino acids 32 to 106 of SEQ ID NOs:2, 4 or 6; and (iv) amino acids 22 to 230 of SEQ ID NOs:2, 4 or 6.

In certain embodiments, the anti-PrP$^c$ antibody is a monoclonal antibody. In certain embodiments, the monoclonal antibody is selected from the group consisting of: a humanized antibody, a chimeric antibody, and a human antibody, and antigen-binding fragments of any of the foregoing. In certain embodiments, the monoclonal antibody specifically binds an epitope within SEQ ID NOs:2, 4 and 6. In one embodiment, the anti-PrP$^c$ antibody is 6D11. In another embodiment, the anti-PrP$^c$ antibody specifically binds to the same epitope as 6D11. In one embodiment, the anti-PrP$^c$ antibody is 8G8. In another embodiment, the anti-PrP$^c$ antibody specifically binds to the same epitope as 8G8.

In certain other embodiments, the PrP$^c$ antagonist comprises a PrP$^c$ antagonist polynucleotide selected from the group consisting of an antisense polynucleotide; a ribozyme; a small interfering RNA (siRNA); and a small-hairpin RNA (shRNA). In other embodiments, the PrP$^c$ antagonist is an aptamer.

In certain embodiments of the invention, the method further comprises administering an additional therapeutic agent. Additional therapeutic agents include, but are not limited to an adrenergic agent, anti-adrenergic agent, anti-androgen agent, anti-anginal agent, anti-anxiety agent, anticonvulsant agent, antidepressant agent, anti-epileptic agent, antihyperlipidemic agent, antihyperlipoproteinemic agent, antihypertensive agent, anti-inflammatory agent, antiobessional agent, antiparkinsonian agent, antipsychotic agent, adrenocortical steroid agent; adrenocortical suppressant agent; aldosterone antagonist agent; amino acid agent; anabolic steroid; analeptic agent; androgen agent; blood glucose regulator; cardioprotectant agent; cardiovascular agent; cholinergic agonist or antagonist; cholinesterase deactivator or inhibitor, such as galantamine, rivastigmine, tacrine and donepezil; cognition adjuvant or enhancer; dopaminergic agent; enzyme inhibitor, estrogen, free oxygen radical scavenger; GABA agonist; glutamate antagonist; hormone; hypocholesterolemic agent; hypolipidemic agent; hypotensive agent; immunizing agent; immunostimulant agent; monoamine oxidase inhibitor, neuroprotective agent; N-methyl D-aspartate (NMDA) antagonist, such as memantine; AMPA antagonist, competitive or-non-competitive NMDA antagonist; opioid antagonist; potassium channel opener; non-hormonal sterol derivative; post-stroke and post-head trauma treatment; prostaglandin; psychotropic agent; relaxant; sedative; sedative-hypnotic agent; selective adenosine antagonist; serotonin antagonist; serotonin inhibitor; selective serotonin uptake inhibitor; serotonin receptor antagonist; sodium and calcium channel blocker; steroid; stimulant; and thyroid hormone and inhibitor agents.

In various embodiments of the above methods, the PrPc antagonist is formulated for administration by a route selected from the group consisting of: parenteral administration, subcutaneous administration, intravenous administration, intramuscular administration, intraperitoneal administration, transdermal administration, inhalational administration, buccal administration, oral administration, microinfusion administration, intrathecal administration, intracranial administration, intracerebroventricular administration, systemic administration, and peripheral administration.

In some embodiments, the PrPc antagonist is administered directly into the central nervous system. In some embodiments, the PrPc antagonist is administered systemically. In other embodiments, the PrPc antagonist is administered peripherally.

In some embodiments, the invention further provides a pharmaceutical kit comprising PrPc antagonist. In further embodiments, the kit further comprises an additional therapeutic agent. Additional therapeutic agents include, but are not limited to an adrenergic agent, anti-adrenergic agent, anti-androgen agent, anti-anginal agent, anti-anxiety agent, anticonvulsant agent, antidepressant agent, anti-epileptic agent, antihyperlipidemic agent, antihyperlipoproteinemic agent, antihypertensive agent, anti-inflammatory agent, anti-obessional agent, antiparkinsonian agent, antipsychotic agent, adrenocortical steroid agent; adrenocortical suppressant agent; aldosterone antagonist agent; amino acid agent; anabolic steroid; analeptic agent; androgen agent; blood glucose regulator; cardioprotectant agent; cardiovascular agent; cholinergic agonist or antagonist; cholinesterase deactivator or inhibitor, such as galantamine, rivastigmine, tacrine and donepezil; cognition adjuvant or enhancer; dopaminergic agent; enzyme inhibitor, estrogen, free oxygen radical scavenger; GABA agonist; glutamate antagonist; hormone; hypocholesterolemic agent; hypolipidemic agent; hypotensive agent; immunizing agent; immunostimulant agent; monoamine oxidase inhibitor, neuroprotective agent; N-methyl D-aspartate (NMDA) antagonist, such as memantine; AMPA antagonist, competitive or- non-competitive NMDA antagonist; opioid antagonist; potassium channel opener; non-hormonal sterol derivative; post-stroke and post-head trauma treatment; prostaglandin; psychotropic agent; relaxant; sedative; sedative-hypnotic agent; selective adenosine antagonist; serotonin antagonist; serotonin inhibitor; selective serotonin uptake inhibitor; serotonin receptor antagonist; sodium and calcium channel blocker; steroid; stimulant; and thyroid hormone and inhibitor agents.

Other embodiments of the invention include a method for identifying a molecule that inhibits suppression of long term potentiation in a mammal, the method comprising: (a) providing a $PrP^c$ polypeptide; (b) contacting the $PrP^c$ polypeptide with a candidate molecule; and (c) detecting a decrease in binding of oligomeric Aβ42 peptide to $PrP^c$ in the presence of the candidate molecule, as compared to the binding of the oligomeric Aβ42 peptide to the $PrP^c$ in the absence of the candidate molecule. A still further embodiment of the invention includes a method for identifying a molecule that inhibits suppression of long term potentiation in a mammal, the method comprising: (a) providing a $PrP^c$ polypeptide; (b) contacting the $PrP^c$ polypeptide with a candidate molecule; and (c) detecting a decrease in expression of $PrP^c$ in the presence of the candidate molecule, as compared to the expression of the $PrP^c$ in the absence of the candidate molecule.

BRIEF DESCRIPTION OF THE DRAWINGS/FIGURES

Figure 2:
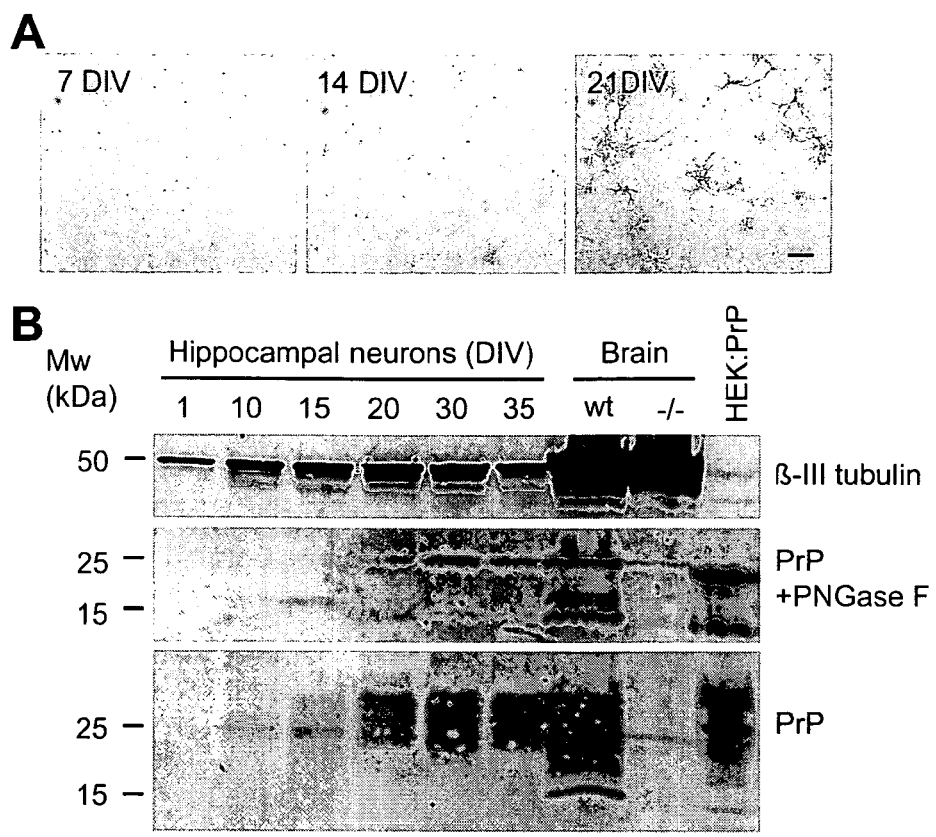
FIG. 2A shows the binding of oligomeric Aβ42 to hippocampal neurons after 4, 14 and 21 days, respectively. Neuronal cell density is similar in the three panels.

FIG. 2B shows an immunoblot of the total protein from hippocampal cultures, whole brain of the indicated genotype or HEK293T cells expressing $PrP^c$ probed with anti-PrP antibody (8F4) and with anti-βIII tubulin antibody. Samples for the middle panel were pretreated with endoglycosidase before gel electrophoresis. Mol wt standards at left. Scale bars, 100 μm.

Figure 3:
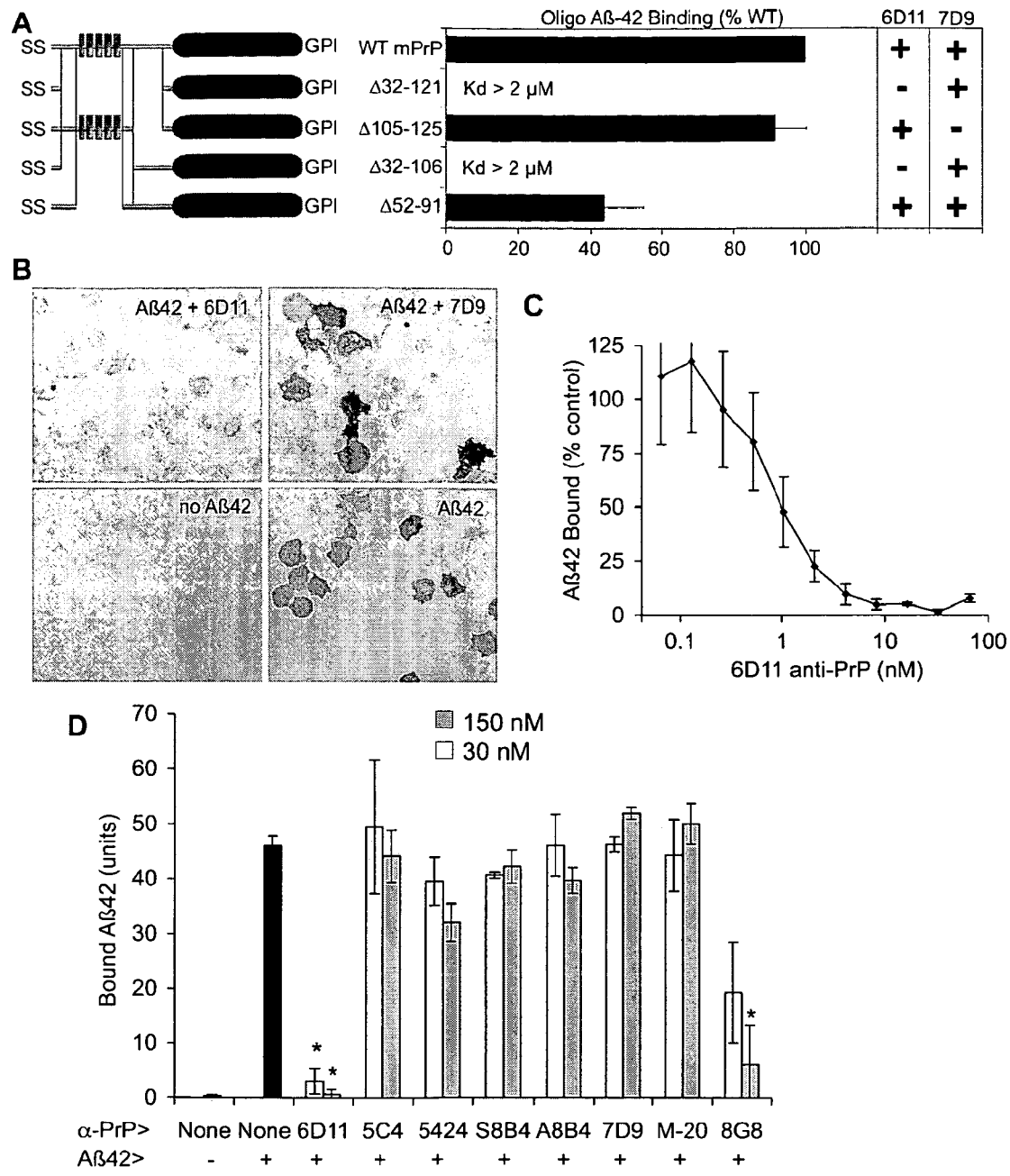

FIG. 3A illustrates the ability of COS-7 cells transfected with various PrP deletion mutants to bind oligomeric Aβ42 and be recognized by anti-PrP antibodies, 6D11 and 7D9. The 5 boxes on the schematic of the PrP sequence are the octapeptide repeats and the shaded area adjacent to the GPI anchor is the globular domain.

FIG. 3B shows the binding of oligomeric Aβ42 to $PrP^c$-expressing COS-7 cells after exposure to anti-PrP antibodies, 6D11 and 7D9, for one hour.

FIG. 3C shows a graph of the level of Aβ42 bound to $PrP^c$-expressing COS-7 cells as a function of the 6D11 antibody concentration.

FIG. 3D shows a graph of the inhibition of Aβ42 bound to $PrP^c$-expressing COS-7 cells after exposure to a panel of anti-PrP antibodies. Data are mean±standard error of the mean (SEM) from 4 experiments. Inhibition of binding by 6D11 or 8G8 is significant relative to no antibody control (*, P<0.02, ANOVA). Scale bar in B is 100 μm.

Figure 4:
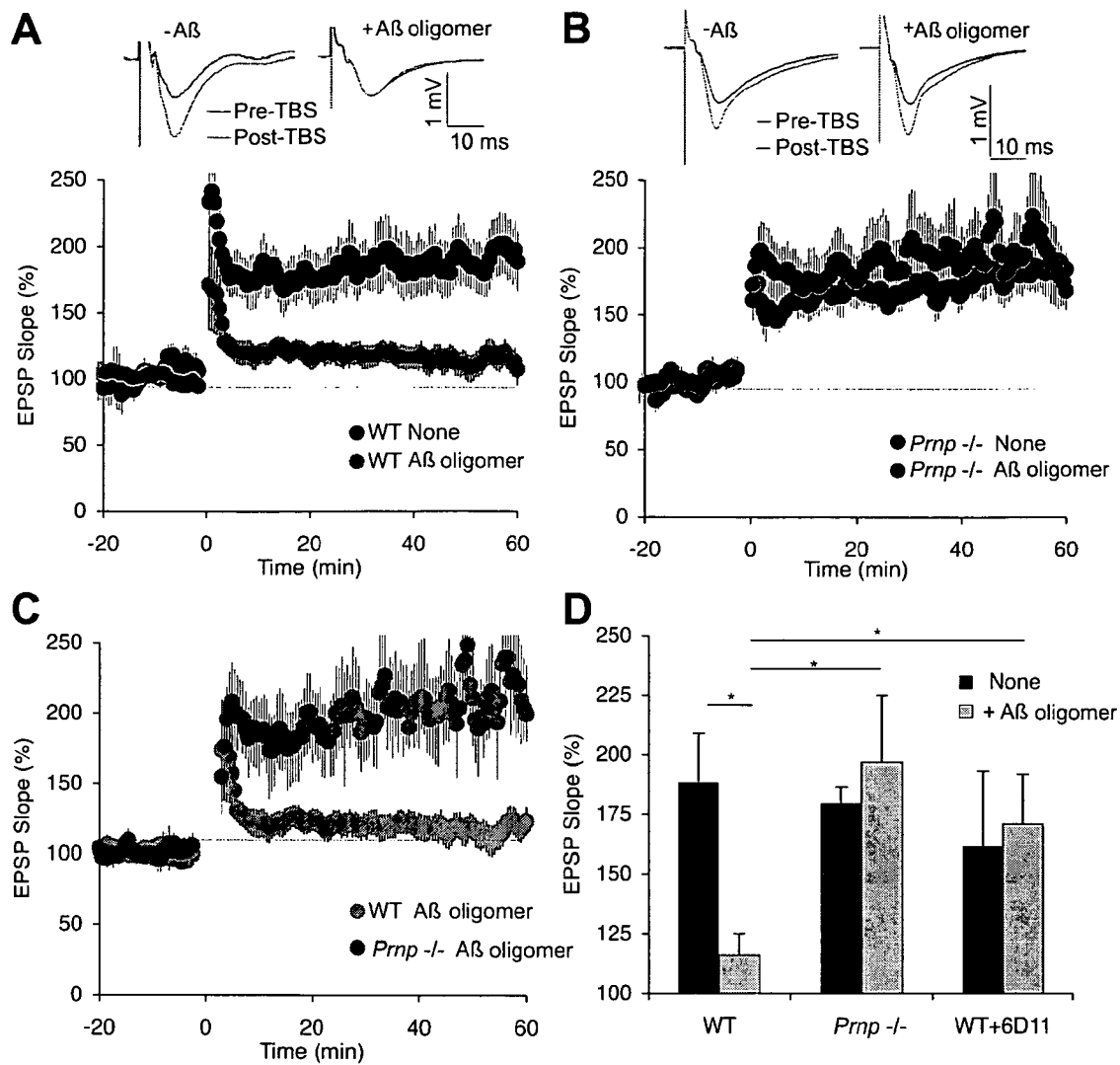

FIG. 4A shows the field potentials from the CA1 region of hippocampal slices from wild type mice with or without the addition of 500 nM oligomeric Aβ42 to the perfusion 20 minutes prior to theta burst stimulation (TBS). The top panels show traces before and after TBS. The slope of the EPSP relative to the pre-TBS level is a plotted as a function of time in the lower panel. Data are mean±standard error of the mean (SEM) from separate slices.

FIG. 4B shows the field potentials from the CA1 region of hippocampal slices from PrP null mice with or without the addition of 500 nM oligomeric Aβ42 to the perfusion 20 minutes prior to theta burst stimulation (TBS).

FIG. 4C shows the field potentials from the CA1 region of hippocampal slices from wild type mice and PrP null mice with the addition of 500 nM oligomeric Aβ42 to the perfusion 20 minutes prior to theta burst stimulation (TBS). For WT, n=17 slices and for Prnp −/−, n=18 slices.

FIG. 4D shows a graph of the magnitude of long term potentiation (LTP) between 30-60 minutes versus a function of genotype, the addition of the 6D11 antibody and/or Aβ42 oligomer prior to the induction of LTP. Data are mean±standard error of the mean (SEM). The indicated comparisons are significant at P<0.02, ANOVA.

Figure 5:
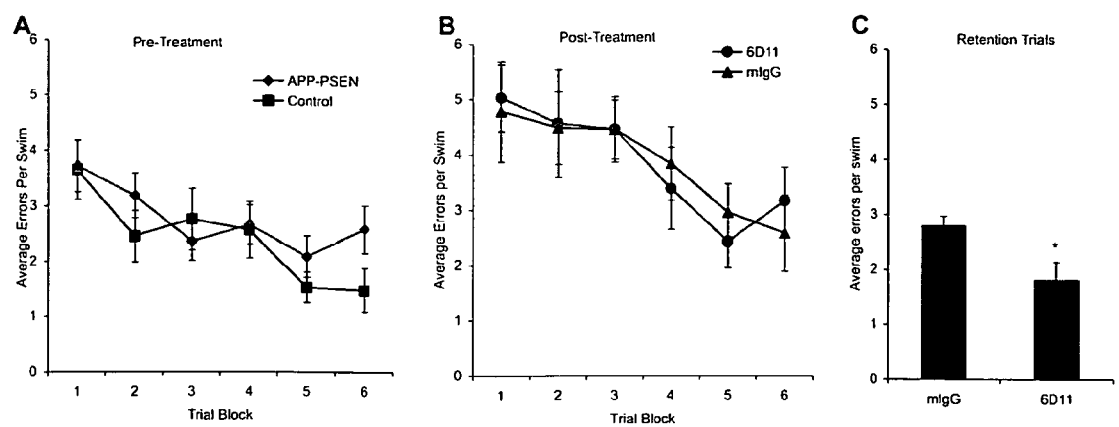

FIG. 5A shows a pre-treatment graph of the number of swim errors in the radial arm water maze versus the number of blocks of 5 swim trials for APPswe/PSEN1ΔE9 transgenic mice and control mice.

FIG. 5B shows a post-treatment graph of the number of swim errors in the radial arm water maze versus the number of blocks of 5 swim trials for 6D11-treated mice and control IgG-treated mice.

FIG. 5C shows a post-treatment graph of the retention of the newly learned spatial memory at 4 and 8 days after the post-injection training session. Mice were scored on one block of 5 swims to measure the retention of the learned platform location. The values for 4 and 8 days were averaged. Data are mean±standard error of the mean (SEM). The indicated comparisons are significant at the P<0.02, ANOVA.

Figure 6:
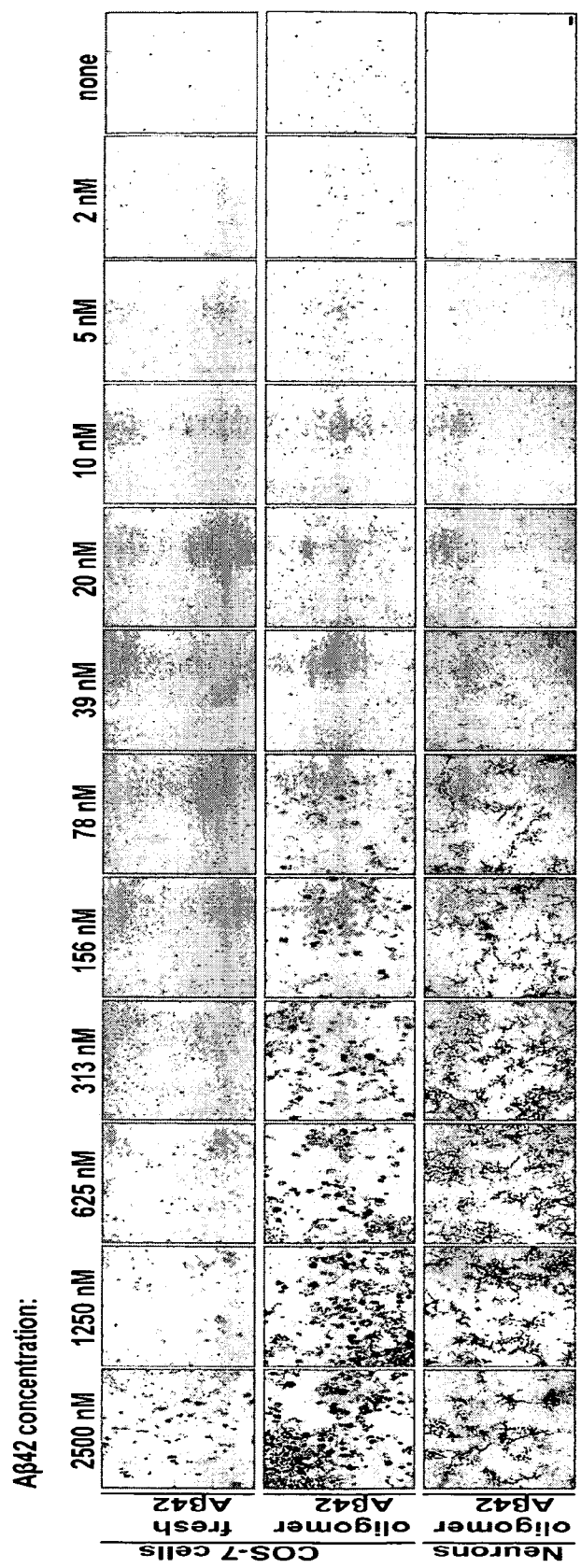

FIG. 6 shows a comparison of fresh and clustered Abeta42 binding to prion protein and to cultured fully differentiated hippocampal neurons. Scale bar 100 μm.

Figure 7:
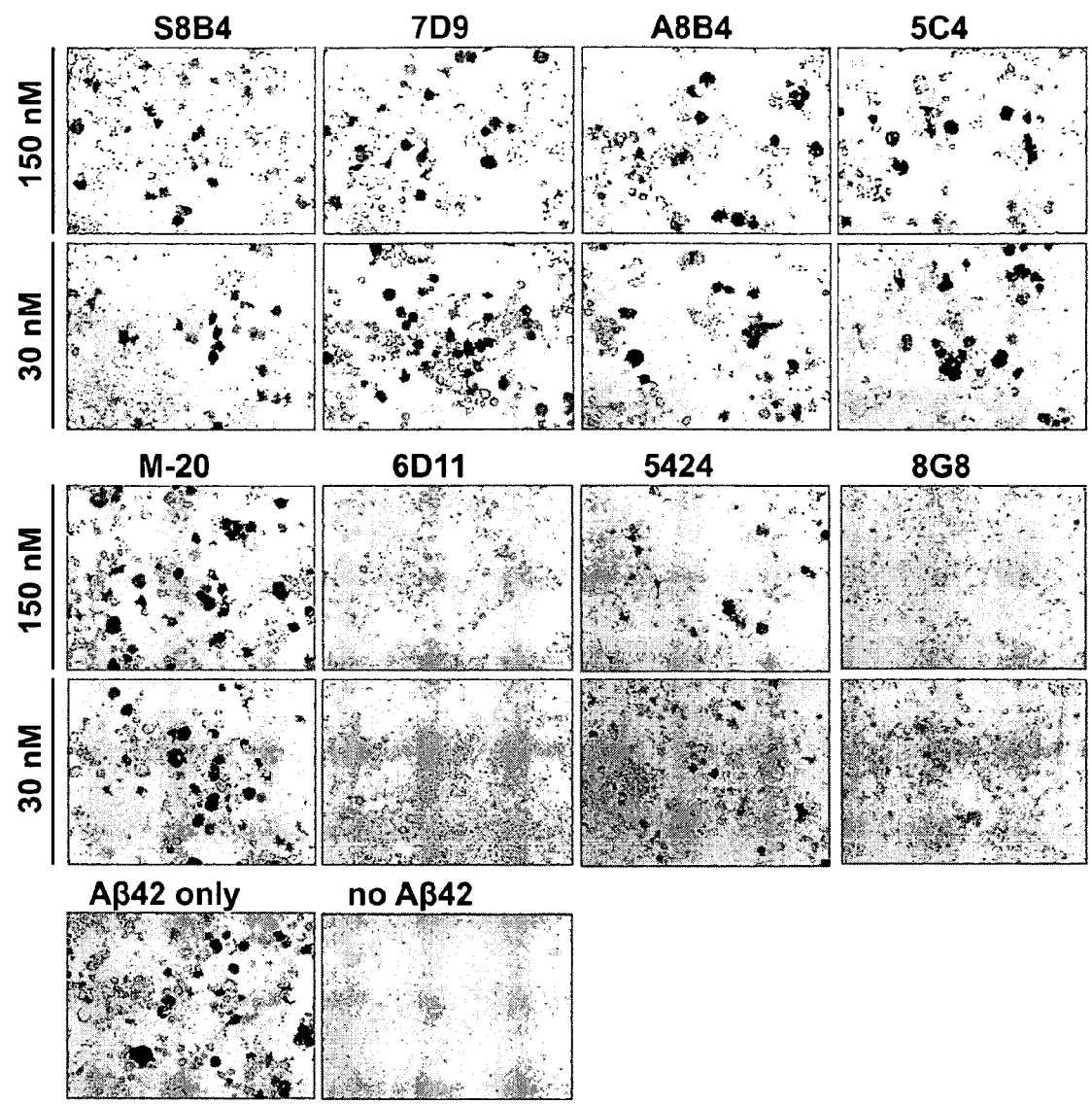

FIG. 7 shows that 6D11 and 8G8 anti-PrP antibodies inhibit binding of Aβ42 to PrP.

DETAILED DESCRIPTION OF THE INVENTION

Definitions

Unless defined otherwise, all technical and scientific terms used herein have the same meaning as commonly understood by one of ordinary skill in the art to which this invention belongs. In case of conflict, the present application including the definitions will control. Unless otherwise required by context, singular terms shall include pluralities and plural terms shall include the singular. All publications, patents and other references mentioned herein are incorporated by reference in their entireties for all purposes as if each individual publication or patent application were specifically and individually indicated to be incorporated by reference.

Although methods and materials similar or equivalent to those described herein can be used in practice or testing of the present invention, suitable methods and materials are described below. The materials, methods and examples are illustrative only and are not intended to be limiting. Other features and advantages of the invention will be apparent from the detailed description and from the claims.

In order to further define this invention, the following terms and definitions are provided.

It is to be noted that the term "a" or "an" entity, refers to one or more of that entity; for example, "an immunoglobulin molecule," is understood to represent one or more immunoglobulin molecules. As such, the terms "a" (or "an"), "one or more," and "at least one" can be used interchangeably herein.

Throughout this specification and claims, the word "comprise," or variations such as "comprises" or "comprising," indicate the inclusion of any recited integer or group of integers but not the exclusion of any other integer or group of integers in the specified method, structure, or composition.

As used herein, the term "consists of," or variations such as "consist of" or "consisting of," as used throughout the specification and claims, indicate the inclusion of any recited integer or group of integers, but that no additional integer or group of integers may be added to the specified method, structure or composition.

As used herein, the term "consists essentially of," or variations such as "consist essentially of" or "consisting essentially of," as used throughout the specification and claims, indicate the inclusion of any recited integer or group of integers, and the optional inclusion of any recited integer or group of integers that do not materially change the basic or novel properties of the specified method, structure or composition.

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" may be used instead of, or interchangeably with any of these terms. The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide may be derived from a natural biological source or produced by recombinant technology, but is not necessarily translated from a designated nucleic acid sequence. It may be generated in any manner, including by chemical synthesis.

In the present invention, a polypeptide can be composed of amino acids joined to each other by peptide bonds or modified peptide bonds, i.e., peptide isosteres, and may contain amino acids other than the 20 gene-encoded amino acids (e.g. non-naturally occurring amino acids). The polypeptides of the present invention may be modified by either natural processes, such as posttranslational processing, or by chemical modification techniques which are well known in the art. Such modifications are well described in basic texts and in more detailed monographs, as well as in a voluminous research literature. Modifications can occur anywhere in the polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched, for example, as a result of ubiquitination, and they may be cyclic, with or without branching. Cyclic, branched, and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, Proteins—Structure And Molecular Properties, 2nd Ed., T. E. Creighton, W. H. Freeman and Company, New York (1993); Posttranslational Covalent Modification of Proteins, B. C. Johnson, Ed., Academic Press, New York, pgs. 1-12 (1983); Seifter et al., *Meth Enzymol* 182:626-646 (1990); Rattan et al., *Ann NY Acad Sci* 663:48-62 (1992).)

A polypeptide of the invention may be of a size of about 3 or more, 5 or more, 10 or more, 20 or more, 25 or more, 50 or more, 75 or more, 100 or more, 200 or more, 500 or more, 1,000 or more, or 2,000 or more amino acids. Polypeptides may have a defined three-dimensional structure, although they do not necessarily have such structure. Polypeptides with a defined three-dimensional structure are referred to as folded, and polypeptides which do not possess a defined three-dimensional structure, but rather can adopt a large number of different conformations, and are referred to as unfolded. As used herein, the term glycoprotein refers to a protein coupled to at least one carbohydrate moiety that is attached to the protein via an oxygen-containing or a nitrogen-containing side chain of an amino acid residue, e.g., a serine residue or an asparagine residue.

By an "isolated" polypeptide or a fragment, variant, or derivative thereof is intended a polypeptide that is not in its natural milieu. No particular level of purification is required. For example, an isolated polypeptide can be removed from its native or natural environment. Recombinantly produced polypeptides and proteins expressed in host cells are considered isolated for purposed of the invention, as are native or recombinant polypeptides which have been separated, fractionated, or partially or substantially purified by any suitable technique.

In the present invention, a "polypeptide fragment" refers to a short amino acid sequence of a larger polypeptide. Protein fragments may be "free-standing," or comprised within a larger polypeptide of which the fragment forms a part of region. Representative examples of polypeptide fragments of the invention, include, for example, fragments comprising about 5 amino acids, about 10 amino acids, about 15 amino acids, about 20 amino acids, about 30 amino acids, about 40 amino acids, about 50 amino acids, about 60 amino acids, about 70 amino acids, about 80 amino acids, about 90 amino acids, and about 100 amino acids or more in length.

The terms "fragment," "variant," "derivative" and "analog" when referring to a polypeptide of the present invention include any polypeptide which retains at least some biological activity. Polypeptides as described herein may include fragment, variant, or derivative molecules therein without limitation, so long as the polypeptide still serves its function. Polypeptides and polypeptide fragments of the present invention may include proteolytic fragments, deletion fragments and in particular, fragments which more easily reach the site of action when delivered to an animal. Polypeptide fragments further include any portion of the polypeptide which comprises an antigenic or immunogenic epitope of the native polypeptide, including linear as well as three-dimensional epitopes. $PrP^c$ antagonist polypeptides and polypeptide fragments of the present invention may comprise variant regions, including fragments as described above, and also polypeptides with altered amino acid sequences due to amino acid substitutions, deletions, or insertions. Variants may occur naturally, such as an allelic variant. By an "allelic variant" is intended alternate forms of a gene occupying a given locus on a chromosome of an organism. Genes II, Lewin, B., ed., John Wiley & Sons, New York (1985). Non-naturally occurring variants may be produced using art-known mutagenesis techniques. $PrP^c$ antagonist polypeptides and polypeptide fragments of the invention may comprise conservative or non-conservative amino acid substitutions, deletions or additions. $PrP^c$ antagonist polypeptides and polypeptide fragments of the present invention may also include derivative molecules. Variant polypeptides may also be referred to herein as "polypeptide analogs." As used herein a "derivative" of a polypeptide or a polypeptide fragment refers to a subject polypeptide having one or more residues chemically derivatized by reaction of a functional side group. Also included as "derivatives" are those peptides which contain one or more naturally occurring amino acid derivatives of the twenty standard amino acids. For example, 4-hydroxyproline may be substituted for proline; 5-hydroxylysine may be substituted for lysine; 3-methylhistidine may be substituted for histidine; homoserine may be substituted for serine; and ornithine may be substituted for lysine.

As used herein the term "disulfide bond" includes the covalent bond formed between two sulfur atoms. The amino acid cysteine comprises a thiol group that can form a disulfide bond or bridge with a second thiol group.

As used herein, "fusion protein" means a protein comprising a first polypeptide linearly connected, via peptide bonds, to a second, polypeptide. The first polypeptide and the second polypeptide may be identical or different, and they may be directly connected, or connected via a peptide linker (see below).

The term "polynucleotide" is intended to encompass a singular nucleic acid as well as plural nucleic acids, and refers to an isolated nucleic acid molecule or construct, e.g., messenger RNA (mRNA) or plasmid DNA (pDNA). A polynucleotide may comprise a conventional phosphodiester bond or a non-conventional bond (e.g., an amide bond, such as found in peptide nucleic acids (PNA)). A polynucleotide can contain the nucleotide sequence of the full length cDNA sequence, including the untranslated 5' and 3' sequences, the coding sequences, as well as fragments, epitopes, domains, and variants of the nucleic acid sequence. The polynucleotide can be composed of any polyribonucleotide or polydeoxyribonucleotide, which may be unmodified RNA or DNA or modified RNA or DNA. For example, polynucleotides can be composed of single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, the polynucleotides can be composed of triple-stranded regions comprising RNA or DNA or both RNA and DNA. Polynucleotides may also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

The term "nucleic acid" refers to any one or more nucleic acid segments, e.g., DNA or RNA fragments, present in a polynucleotide. By "isolated" nucleic acid or polynucleotide is intended a nucleic acid molecule, DNA or RNA, which has been removed from its native environment. For example, a recombinant polynucleotide encoding a $PrP^c$ antagonist polypeptide or polypeptide fragment of the invention contained in a vector is considered isolated for the purposes of the present invention. Further examples of an isolated polynucleotide include recombinant polynucleotides maintained in heterologous host cells or purified (partially or substantially) polynucleotides in solution. Isolated RNA molecules include in vivo or in vitro RNA transcripts of polynucleotides of the present invention. Isolated polynucleotides or nucleic acids according to the present invention further include such molecules produced synthetically. In addition, polynucleotide or a nucleic acid may be or may include a regulatory element such as a promoter, ribosome binding site, or a transcription terminator.

As used herein, a "coding region" is a portion of nucleic acid which consists of codons translated into amino acids. Although a "stop codon" (TAG, TGA, or TAA) is not translated into an amino acid, it may be considered to be part of a coding region, but any flanking sequences, for example promoters, ribosome binding sites, transcriptional terminators, introns, and the like, are not part of a coding region. Two or more coding regions of the present invention can be present in a single polynucleotide construct, e.g., on a single vector, or in separate polynucleotide constructs, e.g., on separate (different) vectors. Furthermore, any vector may contain a single coding region, or may comprise two or more coding regions, e.g., a single vector may separately encode an immunoglobulin heavy chain variable region and an immunoglobulin light chain variable region. In addition, a vector, polynucleotide, or nucleic acid of the invention may encode heterologous coding regions, either fused or unfused to a nucleic acid encoding a $PrP^c$ antagonist polypeptide or polypeptide fragment of the present invention. Heterologous coding regions include without limitation specialized elements or motifs, such as a secretory signal peptide or a heterologous functional domain.

In certain embodiments, the polynucleotide or nucleic acid is DNA. In the case of DNA, a polynucleotide comprising a nucleic acid which encodes a polypeptide normally may include a promoter and/or other transcription or translation control elements operably associated with one or more coding regions. An operable association is when a coding region for a gene product, e.g., a polypeptide, is associated with one or more regulatory sequences in such a way as to place expression of the gene product under the influence or control of the regulatory sequence(s). Two DNA fragments (such as a polypeptide coding region and a promoter associated therewith) are "operably associated" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operably associated with a nucleic acid encoding a polypeptide if the promoter was capable of effecting transcription of that nucleic acid. The promoter may be a cell-specific promoter that directs substantial transcription of the DNA only in predetermined cells. Other transcription control elements, besides a promoter, for example enhancers, operators, repressors, and transcription termination signals, can be operably associated with the polynucleotide to direct cell-specific transcription. Suitable promoters and other transcription control regions are disclosed herein.

A variety of transcription control regions are known to those skilled in the art. These include, without limitation, transcription control regions which function in vertebrate cells, such as, but not limited to, promoter and enhancer segments from cytomegaloviruses (the immediate early promoter, in conjunction with intron-A), simian virus 40 (the early promoter), and retroviruses (such as Rous sarcoma virus). Other transcription control regions include those derived from vertebrate genes such as actin, heat shock protein, bovine growth hormone and rabbit β-globin, as well as other sequences capable of controlling gene expression in eukaryotic cells. Additional suitable transcription control regions include tissue-specific promoters and enhancers as well as lymphokine-inducible promoters (e.g., promoters inducible by interferons or interleukins).

Similarly, a variety of translation control elements are known to those of ordinary skill in the art. These include, but are not limited to ribosome binding sites, translation initiation and termination codons, and elements derived from picornaviruses (particularly an internal ribosome entry site, or IRES, also referred to as a CITE sequence).

In other embodiments, a polynucleotide of the present invention is RNA, for example, in the form of messenger RNA (mRNA).

Polynucleotide and nucleic acid coding regions of the present invention may be associated with additional coding regions which encode secretory or signal peptides, which direct the secretion of a polypeptide encoded by a polynucleotide of the present invention. According to the signal hypothesis, proteins secreted by mammalian cells have a signal peptide or secretory leader sequence which is cleaved from the mature protein once export of the growing protein chain across the rough endoplasmic reticulum has been initiated. Those of ordinary skill in the art are aware that polypeptides secreted by vertebrate cells generally have a signal peptide fused to the N-terminus of the polypeptide, which is cleaved from the complete or "full length" polypeptide to produce a secreted or "mature" form of the polypeptide. In certain embodiments, the native signal peptide, e.g., an immunoglobulin heavy chain or light chain signal peptide is used, or a functional derivative of that sequence that retains the ability to direct the secretion of the polypeptide that is operably associated with it. Alternatively, a heterologous mammalian signal peptide, or a functional derivative thereof, may be used. For example, the wild-type leader sequence may be substituted with the leader sequence of human tissue plasminogen activator (TPA) or mouse β-glucuronidase.

In certain embodiments, agents for use in the methods disclosed herein are "antibody" or "immunoglobulin" molecules, or immunospecific fragments thereof, e.g., naturally occurring antibody or immunoglobulin molecules or engineered antibody molecules or fragments that bind antigen in a manner similar to antibody molecules. As used herein, the term "antibody" is used in the broadest sense and covers polyclonal as well as monoclonal antibodies, including full length antibodies, multispecific antibodies (e.g., bispecific antibodies), chimeric, humanized and fully human antibodies, and fragments of such antibodies including Fab, Fab', F(ab')2, and Fv fragments, diabodies, linear antibodies, single-chain antibody molecules, and multispecific antibodies formed from antibody fragments, so long as they exhibit the desired antigen-binding activity. A monoclonal antibody indicates the character of the antibody as being a substantially homogeneous population of antibodies, and is not to be construed as requiring production of the antibody by any particular method.

The terms "antibody" and "immunoglobulin" are used interchangeably herein. An antibody or immunoglobulin comprises at least the variable domain of a heavy chain, and normally comprises at least the variable domains of a heavy chain and a light chain. Basic immunoglobulin structures in vertebrate systems are relatively well understood. See, e.g., Harlow et al., Antibodies: A Laboratory Manual, (Cold Spring Harbor Laboratory Press, 2nd ed. 1988).

As will be discussed in more detail below, the term "immunoglobulin" comprises various broad classes of polypeptides that can be distinguished biochemically. Those skilled in the art will appreciate that heavy chains are classified as gamma, mu, alpha, delta, or epsilon, (γ, μ, α, δ, ε) with some subclasses among them (e.g., γ1-γ4). It is the nature of this chain that determines the "class" of the antibody as IgG, IgM, IgA IgG, or IgE, respectively. The immunoglobulin subclasses (isotypes) e.g., IgG1, IgG2, IgG3, IgG4, IgA1, etc. are well characterized and are known to confer functional specialization. Modified versions of each of these classes and isotypes are readily discernable to the skilled artisan in view of the instant disclosure and, accordingly, are within the scope of the instant invention. All immunoglobulin classes are clearly within the scope of the present invention, the following discussion will generally be directed to the IgG class of immunoglobulin molecules. With regard to IgG, a standard immunoglobulin molecule comprises two identical light chain polypeptides of molecular weight approximately 23,000 Daltons, and two identical heavy chain polypeptides of molecular weight 53,000-70,000. The four chains are typically joined by disulfide bonds in a "Y" configuration wherein the light chains bracket the heavy chains starting at the mouth of the "Y" and continuing through the variable region.

Both the light and heavy chains are divided into regions of structural and functional homology. The terms "constant" and "variable" are used functionally. In this regard, it will be appreciated that the variable domains of both the light (VL) and heavy (VH) chain portions determine antigen recognition and specificity. Conversely, the constant domains of the light chain (CL) and the heavy chain (CH1, CH2 or CH3) confer important biological properties such as secretion, transplacental mobility, Fc receptor binding, complement binding, and the like. By convention the numbering of the constant region domains increases as they become more distal from the antigen binding site or amino-terminus of the antibody. The N-terminal portion is a variable region and at the C-terminal portion is a constant region; the CH3 and CL domains actually comprise the carboxy-terminus of the heavy and light chain, respectively.

Light chains are classified as either kappa or lambda (κ, λ). Each heavy chain class may be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain. Those skilled in the art will appreciate that heavy chains are classified as gamma, mu, alpha, delta, or epsilon, (γ, μ, α, δ, ε) with some subclasses among them (e.g., γ1-γ4). It is the nature of this chain that determines the "class" of the antibody as IgG, IgM, IgA IgG, or IgE, respectively. The immunoglobulin subclasses (isotypes) e.g., IgG1, IgG2, IgG3, IgG4, IgA1, etc. are well characterized and are known to confer functional specialization. Modified versions of each of these classes and isotypes are readily discernable to the skilled artisan in view of the instant disclosure and, accordingly, are within the scope of the instant invention.

As indicated above, the variable region allows the antibody to selectively recognize and specifically bind epitopes on antigens. That is, the VL domain and VH domain of an antibody combine to form the variable region that defines a three dimensional antigen binding site. This quaternary antibody structure forms the antigen binding site present at the end of each arm of the Y. More specifically, the antigen binding site is defined by three complementary determining regions (CDRs) on each of the VH and VL chains. In some instances, e.g., certain immunoglobulin molecules derived from camelid species or engineered based on camelid immunoglobulins, a complete immunoglobulin molecule may consist of heavy chains only, with no light chains. See, e.g., Hamers Casterman et al., *Nature* 363:446 448 (1993).

In one embodiment, an antigen binding molecule of the invention comprises at least one heavy or light chain CDR of an antibody molecule. In another embodiment, an antigen binding molecule of the invention comprises at least two CDRs from one or more antibody molecules. In another embodiment, an antigen binding molecule of the invention comprises at least three CDRs from one or more antibody molecules. In another embodiment, an antigen binding molecule of the invention comprises at least four CDRs from one or more antibody molecules. In another embodiment, an antigen binding molecule of the invention comprises at least five CDRs from one or more antibody molecules. In another embodiment, an antigen binding molecule of the invention comprises at least six CDRs from one or more antibody molecules. Exemplary antibody molecules comprising at least one CDR that can be included in the subject antigen binding molecules are known in the art and exemplary molecules are described herein.

Antibodies or immunospecific fragments thereof for use in the methods of the invention include, but are not limited to, polyclonal, monoclonal, multispecific, human, humanized, primatized, or chimeric antibodies, single chain antibodies, epitope-binding fragments, e.g., Fab, Fab' and F(ab')2, Fd, Fvs, single-chain Fvs (scFv), single-chain antibodies, disulfide-linked Fvs (sdFv), fragments comprising either a VL or VH domain, fragments produced by a Fab expression library, and anti-idiotypic (anti-Id) antibodies (including, e.g., anti-Id antibodies to binding molecules disclosed herein). ScFv molecules are known in the art and are described, e.g., in U.S. Pat. No. 5,892,019. Immunoglobulin or antibody molecules of the invention can be of any type (e.g., IgG, IgE, IgM, IgD, IgA, and IgY), class (e.g., IgG1, IgG2, IgG3, IgG4, IgA1 and IgA2) or subclass of immunoglobulin molecule.

The term "antibody" as used herein is also intended to encompass antibodies, digestion fragments, specified portions and variants thereof, including antibody mimetics or comprising portions of antibodies that mimic the structure and/or function of an antibody or specified fragment or portion thereof, including single chain antibodies and fragments thereof; each containing at least one CDR. See Qiu et al., *Nature Biotechnology* 25:921-929 (2007). Functional fragments include antigen binding fragments that bind to a PrP$^c$ antigen. For example, antibody fragments capable of binding to PrP$^c$ or a portion thereof, including, but not limited to Fab (e.g., by papain digestion), facb (e.g., by plasmin digestion), pFc' (e.g., by pepsin or plasmin digestion), Fd (e.g., by pepsin digestion, partial reduction and reaggregation), Fv or scFv (e.g., by molecular biology techniques) fragments, are encompassed by the present invention. Antibody fragments are also intended to include, e.g., domain deleted antibodies, diabodies, linear antibodies, single-chain antibody molecules, and multispecific antibodies formed from antibody fragments.

Antibody fragments, including single-chain antibodies, may comprise the variable region(s) alone or in combination with the entirety or a portion of the following: hinge region, CH1, CH2, and CH3 domains. Also included in the invention are antigen-binding fragments also comprising any combination of variable region(s) with a hinge region, CH1, CH2, and CH3 domains. Antibodies or immunospecific fragments thereof for use in the diagnostic and therapeutic methods disclosed herein may be from any animal origin including birds and mammals. Preferably, the antibodies are human, murine, donkey, rabbit, goat, guinea pig, camel, llama, horse, or chicken antibodies. In another embodiment, the variable region may be condricthoid in origin (e.g., from sharks). As used herein, "human" antibodies include antibodies having the amino acid sequence of a human immunoglobulin and include antibodies isolated from human immunoglobulin libraries or from animals transgenic for one or more human immunoglobulins and that do not express endogenous immunoglobulins, as described infra and, for example in, U.S. Pat. No. 5,939,598 by Kucherlapati et al.

As used herein, the term "heavy chain portion" includes amino acid sequences derived from an immunoglobulin heavy chain. A polypeptide comprising a heavy chain portion comprises at least one of: a CH1 domain, a hinge (e.g., upper, middle, and/or lower hinge region) domain, a CH2 domain, a CH3 domain, or a variant or fragment thereof. For example, a binding polypeptide for use in the invention may comprise a polypeptide chain comprising a CH1 domain; a polypeptide chain comprising a CH1 domain, at least a portion of a hinge domain, and a CH2 domain; a polypeptide chain comprising a CH1 domain and a CH3 domain; a polypeptide chain comprising a CH1 domain, at least a portion of a hinge domain, and a CH3 domain, or a polypeptide chain comprising a CH1 domain, at least a portion of a hinge domain, a CH2 domain, and a CH3 domain. In another embodiment, a polypeptide of the invention comprises a polypeptide chain comprising a CH3 domain. Further, a binding polypeptide for use in the invention may lack at least a portion of a CH2 domain (e.g., all or part of a CH2 domain). As set forth above, it will be understood by one of ordinary skill in the art that these domains (e.g., the heavy chain portions) may be modified such that they vary in amino acid sequence from the naturally occurring immunoglobulin molecule.

In certain PrP$^c$ antagonist antibodies or immunospecific fragments thereof for use in the treatment methods disclosed herein, the heavy chain portions of one polypeptide chain of a multimer are identical to those on a second polypeptide chain of the multimer. Alternatively, heavy chain portion-containing monomers for use in the methods of the invention are not identical. For example, each monomer may comprise a different target binding site, forming, for example, a bispecific antibody.

The heavy chain portions of a binding polypeptide for use in the methods disclosed herein may be derived from different immunoglobulin molecules. For example, a heavy chain portion of a polypeptide may comprise a CH1 domain derived from an IgG1 molecule and a hinge region derived from an IgG3 molecule. In another example, a heavy chain portion can comprise a hinge region derived, in part, from an IgG1 molecule and, in part, from an IgG3 molecule. In another example, a heavy chain portion can comprise a chimeric hinge derived, in part, from an IgG1 molecule and, in part, from an IgG4 molecule.

As used herein, the term "light chain portion" includes amino acid sequences derived from an immunoglobulin light chain. Preferably, the light chain portion comprises at least one of a VL or CL domain.

Antibodies or immunospecific fragments thereof for use in the treatment methods disclosed herein act as antagonists of PrP$^c$ as described herein. For example, an antibody for use in the methods of the present invention may function as an antagonist, blocking or inhibiting the suppressive activity of PrP$^c$.

An isolated nucleic acid molecule encoding a non-natural variant of a polypeptide derived from an immunoglobulin (e.g., an immunoglobulin heavy chain portion or light chain portion) can be created by introducing one or more nucleotide substitutions, additions or deletions into the nucleotide sequence of the immunoglobulin such that one or more amino acid substitutions, additions or deletions are introduced into the encoded protein. Mutations may be introduced by standard techniques, such as site-directed mutagenesis and PCR-mediated mutagenesis. Preferably, conservative amino acid substitutions are made at one or more non-essential amino acid residues.

Anti-PrP$^c$ antagonist antibodies, or antigen-binding fragments, variants, or derivatives thereof disclosed herein may be described or specified in terms of the epitope(s) or portion(s) of an antigen, e.g., a target polypeptide (PrP$^c$) that they recognize or specifically bind. The portion of a target polypeptide which specifically interacts with the antigen binding domain of an antibody is an "epitope," or an "antigenic determinant." A target polypeptide may comprise a single epitope, but typically comprises at least two epitopes, and can include any number of epitopes, depending on the size, conformation, and type of antigen. Furthermore, it should be noted that an "epitope" on a target polypeptide may be or include non-polypeptide elements, e.g., an "epitope may include a carbohydrate side chain.

The minimum size of a peptide or polypeptide epitope for an antibody is thought to be about four to five amino acids. Peptide or polypeptide epitopes preferably contain at least seven, more preferably at least nine and most preferably between at least about 15 to about 30 amino acids. Since a CDR can recognize an antigenic peptide or polypeptide in its tertiary form, the amino acids comprising an epitope need not be contiguous, and in some cases, may not even be on the same peptide chain. In the present invention, peptide or polypeptide epitope recognized by anti-$PrP^c$ receptor complex molecule antagonist antibodies of the present invention contains a sequence of at least 4, at least 5, at least 6, at least 7, more preferably at least 8, at least 9, at least 10, at least 15, at least 20, at least 25, or between about 15 to about 30 contiguous or non-contiguous amino acids of $PrP^c$, e.g., SEQ ID NO:2.

By "specifically binds," it is generally meant that an antibody binds to an epitope via its antigen binding domain, and that the binding entails some complementarity between the antigen binding domain and the epitope. According to this definition, an antibody is said to "specifically bind" to an epitope when it binds to that epitope, via its antigen binding domain more readily than it would bind to a random, unrelated epitope. The term "specificity" is used herein to qualify the relative affinity by which a certain antibody binds to a certain epitope. For example, antibody "A" may be deemed to have a higher specificity for a given epitope than antibody "B," or antibody "A" may be said to bind to epitope "C" with a higher specificity than it has for related epitope "D."

By "preferentially binds," it is meant that the antibody specifically binds to an epitope more readily than it would bind to a related, similar, homologous, or analogous epitope. Thus, an antibody which "preferentially binds" to a given epitope would more likely bind to that epitope than to a related epitope, even though such an antibody may cross-react with the related epitope.

By way of non-limiting example, an antibody may be considered to bind a first epitope preferentially if it binds said first epitope with a dissociation constant ($K_D$) that is less than the antibody's $K_D$ for the second epitope. In another non-limiting example, an antibody may be considered to bind a first antigen preferentially if it binds the first epitope with an affinity that is at least one order of magnitude less than the antibody's $K_D$ for the second epitope. In another non-limiting example, an antibody may be considered to bind a first epitope preferentially if it binds the first epitope with an affinity that is at least two orders of magnitude less than the antibody's $K_D$ for the second epitope.

In another non-limiting example, an antibody may be considered to bind a first epitope preferentially if it binds the first epitope with an off rate (k(off)) that is less than the antibody's k(off) for the second epitope. In another non-limiting example, an antibody may be considered to bind a first epitope preferentially if it binds the first epitope with an affinity that is at least one order of magnitude less than the antibody's k(off) for the second epitope. In another non-limiting example, an antibody may be considered to bind a first epitope preferentially if it binds the first epitope with an affinity that is at least two orders of magnitude less than the antibody's k(off) for the second epitope.

An antibody or or antigen-binding fragment, variant, or derivative disclosed herein may be said to bind a target polypeptide disclosed herein or a fragment or variant thereof with an off rate (k(off)) of less than or equal to $5\times10^{-2}$ $sec^{-1}$, $10^{-2}$ $sec^{-1}$, $5\times10^{-3}$ $sec^{-1}$ or $10^{-3}$ $sec^{-1}$. More preferably, an antibody of the invention may be said to bind a target polypeptide disclosed herein or a fragment or variant thereof with an off rate (k(off)) less than or equal to $5\times10^{-4}$ $sec^{-1}$, $10^{-4}$ $sec^{-1}$, $5\times10^{-5}$ $sec^{-1}$, or $10^{-5}$ $sec^{-1}$ $5\times10^{-6}$ $sec^{-1}$, $10^{-6}$ $sec^{-1}$, $5\times10^{-7}$ $sec^{-1}$ or $10^{-7}$ $sec^{-1}$.

An antibody or or antigen-binding fragment, variant, or derivative disclosed herein may be said to bind a target polypeptide disclosed herein or a fragment or variant thereof with an on rate (k(on)) of greater than or equal to $10^3$ $M^{-1}$ $sec^{-1}$, $5 \times 10^3$ $M^{-1}$ $sec^{-1}$, $10^4$ $M^{-1}$ $sec^{-1}$ or $5 \times 10^4$ $M^{-1}$ $sec^{-1}$. More preferably, an antibody of the invention may be said to bind a target polypeptide disclosed herein or a fragment or variant thereof with an on rate (k(on)) greater than or equal to $10^5$ $M^{-1}$ $sec^{-1}$, $5 \times 10^5$ $M^{-1}$ $sec^{-1}$, $10^6$ $M^{-1}$ $sec^{-1}$, or $5 \times 10^6$ $M^{-1}$ $sec^{-1}$ or $10^7$ $M^{-1}$ $sec^{-1}$.

An antibody is said to competitively inhibit binding of a reference antibody to a given epitope if it preferentially binds to that epitope to the extent that it blocks, to some degree, binding of the reference antibody to the epitope. Competitive inhibition may be determined by any method known in the art, for example, competition ELISA assays. An antibody may be said to competitively inhibit binding of the reference antibody to a given epitope by at least 90%, at least 80%, at least 70%, at least 60%, or at least 50%.

As used herein, the term "affinity" refers to a measure of the strength of the binding of an individual epitope with the CDR of an immunoglobulin molecule. See, e.g., Harlow et al., Antibodies: A Laboratory Manual, (Cold Spring Harbor Laboratory Press, 2nd ed. 1988) at pages 27-28. As used herein, the term "avidity" refers to the overall stability of the complex between a population of immunoglobulins and an antigen, that is, the functional combining strength of an immunoglobulin mixture with the antigen. See, e.g., Harlow at pages 29-34. Avidity is related to both the affinity of individual immunoglobulin molecules in the population with specific epitopes, and also the valencies of the immunoglobulins and the antigen. For example, the interaction between a bivalent monoclonal antibody and an antigen with a highly repeating epitope structure, such as a polymer, would be one of high avidity.

Anti-$PrP^c$ antagonist antibodies or antigen-binding fragments, variants or derivatives thereof of the invention may also be described or specified in terms of their cross-reactivity. As used herein, the term "cross-reactivity" refers to the ability of an antibody, specific for one antigen, to react with a second antigen; a measure of relatedness between two different antigenic substances. Thus, an antibody is cross reactive if it binds to an epitope other than the one that induced its formation. The cross reactive epitope generally contains many of the same complementary structural features as the inducing epitope, and in some cases, may actually fit better than the original.

For example, certain antibodies have some degree of cross-reactivity, in that they bind related, but non-identical epitopes, e.g., epitopes with at least 95%, at least 90%, at least 85%, at least 80%, at least 75%, at least 70%, at least 65%, at least 60%, at least 55%, and at least 50% identity (as calculated using methods known in the art and described herein) to a reference epitope. An antibody may be said to have little or no cross-reactivity if it does not bind epitopes with less than 95%, less than 90%, less than 85%, less than 80%, less than 75%, less than 70%, less than 65%, less than 60%, less than 55%, and less than 50% identity (as calculated using methods known in the art and described herein) to a reference epitope. An antibody may be deemed "highly specific" for a certain epitope, if it does not bind any other analog, ortholog, or homolog of that epitope.

Antibodies or immunospecific fragments thereof for use in the treatment methods disclosed herein may also be described or specified in terms of their binding affinity to a polypeptide of the invention. Preferred binding affinities include those with a dissociation constant or Kd less than $5 \times 10^{-2}$ M, $10^{-2}$ M, $5 \times 10^{-3}$ M, $10^{-3}$ M, $5 \times 10^{-4}$ M, $10^{-4}$ M, $5 \times 10^{-5}$ M, $10^{-5}$ M, $5 \times 10^{-6}$ M, $10^{-6}$ M, $5 \times 10^{-7}$ M, $10^{-7}$ M, $5 \times 10^{-8}$ M, $10^{-8}$ M, $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M, $5 \times 10^{-13}$ M, $10^{-13}$ M, $5 \times 10^{-14}$ M, $10^{-14}$ M, $5 \times 10^{-15}$ M, or $10^{-15}$ M.

Anti-$PrP^c$ antagonist antibodies or antigen-binding fragments, variants or derivatives thereof of the invention may be "multispecific," e.g., bispecific, trispecific or of greater multispecificity, meaning that it recognizes and binds to two or more different epitopes present on one or more different antigens (e.g., proteins) at the same time. Thus, whether an anti-$PrP^c$ antagonist antibody is "monospecfic" or "multispecific," e.g., "bispecific," refers to the number of different epitopes with which a binding polypeptide reacts. Multispecific antibodies may be specific for different epitopes of a target polypeptide described herein or may be specific for a target polypeptide as well as for a heterologous epitope, such as a heterologous polypeptide or solid support material.

As used herein the term "valency" refers to the number of potential binding domains, e.g., antigen binding domains, present in an anti-$PrP^c$ antagonist antibody, binding polypeptide or antibody. Each binding domain specifically binds one epitope. When an anti-$PrP^c$ antagonist antibody or binding polypeptide comprises more than one binding domain, each binding domain may specifically bind the same epitope, for an antibody with two binding domains, termed "bivalent monospecific," or to different epitopes, for an antibody with two binding domains, termed "bivalent bispecific." An antibody may also be bispecific and bivalent for each specificity (termed "bispecific tetravalent antibodies"). In another embodiment, tetravalent minibodies or domain deleted antibodies can be made.

Bispecific bivalent antibodies, and methods of making them, are described, for instance in U.S. Pat. Nos. 5,731,168; 5,807,706; 5,821,333; and U.S. Appl. Publ. Nos. 2003/020734 and 2002/0155537, the disclosures of all of which are incoporated by reference herein. Bispecific tetravalent antibodies, and methods of making them are described, for instance, in WO 02/096948 and WO 00/44788, the disclosures of both of which are incorporated by reference herein. See generally, PCT publications WO 93/17715; WO 92/08802; WO 91/00360; WO 92/05793; Tutt et al., J. Immunol. 147:60-69 (1991); U.S. Pat. Nos. 4,474,893; 4,714,681; 4,925,648; 5,573,920; 5,601,819; Kostelny et al., J. Immunol. 148:1547-1553 (1992).

As previously indicated, the subunit structures and three dimensional configuration of the constant regions of the various immunoglobulin classes are well known. As used herein, the term "$V_H$ domain" includes the amino terminal variable domain of an immunoglobulin heavy chain and the term "$C_H1$ domain" includes the first (most amino terminal) constant region domain of an immunoglobulin heavy chain. The $C_H1$ domain is adjacent to the $V_H$ domain and is amino terminal to the hinge region of an immunoglobulin heavy chain molecule.

As used herein the term "$C_H2$ domain" includes the portion of a heavy chain molecule that extends, e.g., from about residue 244 to residue 360 of an antibody using conventional numbering schemes (residues 244 to 360, Kabat numbering system; and residues 231-340, EU numbering system; see Kabat E A et al. op. cit. The $C_H2$ domain is unique in that it is not closely paired with another domain. Rather, two N-linked branched carbohydrate chains are interposed between the two $C_H2$ domains of an intact native IgG molecule. It is also well documented that the $C_H3$ domain extends from the $C_H2$ domain to the C-terminal of the IgG molecule and comprises approximately 108 residues.

As used herein, the term "hinge region" includes the portion of a heavy chain molecule that joins the $C_H1$ domain to the $C_H2$ domain. This hinge region comprises approximately 25 residues and is flexible, thus allowing the two N-terminal antigen binding regions to move independently. Hinge regions can be subdivided into three distinct domains: upper, middle, and lower hinge domains (Roux et al., *J. Immunol.* 161:4083 (1998)).

As used herein the term "disulfide bond" includes the covalent bond formed between two sulfur atoms. The amino acid cysteine comprises a thiol group that can form a disulfide bond or bridge with a second thiol group. In most naturally occurring IgG molecules, the $C_H1$ and $C_L$ regions are linked by a disulfide bond and the two heavy chains are linked by two disulfide bonds at positions corresponding to 239 and 242 using the Kabat numbering system (position 226 or 229, EU numbering system).

As used herein, the term "chimeric antibody" will be held to mean any antibody wherein the immunoreactive region or site is obtained or derived from a first species and the constant region (which may be intact, partial or modified in accordance with the instant invention) is obtained from a second species. In preferred embodiments the target binding region or site will be from a non-human source (e.g. mouse or primate) and the constant region is human.

As used herein, the term "engineered antibody" refers to an antibody in which the variable domain in either the heavy and light chain or both is altered by at least partial replacement of one or more CDRs from an antibody of known specificity and, if necessary, by partial framework region replacement and sequence changing. Although the CDRs may be derived from an antibody of the same class or even subclass as the antibody from which the framework regions are derived, it is envisaged that the CDRs will be derived from an antibody of different class and preferably from an antibody from a different species. An engineered antibody in which one or more "donor" CDRs from a non-human antibody of known specificity is grafted into a human heavy or light chain framework region is referred to herein as a "humanized antibody." It may not be necessary to replace all of the CDRs with the complete CDRs from the donor variable region to transfer the antigen binding capacity of one variable domain to another. Rather, it may only be necessary to transfer those residues that are necessary to maintain the activity of the target binding site. Given the explanations set forth in, e.g., U.S. Pat. Nos. 5,585,089, 5,693,761, 5,693,762, and 6,180,370, it will be well within the competence of those skilled in the art, either by carrying out routine experimentation or by trial and error testing to obtain a functional engineered or humanized antibody.

As used herein, the terms "linked," "fused" or "fusion" are used interchangeably. These terms refer to the joining together of two more elements or components, by whatever means including chemical conjugation or recombinant means. An "in-frame fusion" refers to the joining of two or more open reading frames (ORFs) to form a continuous longer ORF, in a manner that maintains the correct reading frame of the original ORFs. Thus, the resulting recombinant fusion protein is a single protein containing two or more segments that correspond to polypeptides encoded by the original ORFs (which segments are not normally so joined in nature.) Although the reading frame is thus made continuous throughout the fused segments, the segments may be physically or spatially separated by, for example, in-frame linker sequence.

A "linker" sequence is a series of one or more amino acids separating two polypeptide coding regions in a fusion protein. A typical linker comprises, e.g., at least 5 amino acids. Additional linkers comprise at least 10 or at least 15 amino acids. In certain embodiments, the amino acids of a peptide linker are selected so that the linker is hydrophilic. The linker (Gly-Gly-Gly-Gly-Ser)$_3$ (SEQ ID NO: 7) is a preferred linker that is widely applicable to many antibodies as it provides sufficient flexibility. Other linkers include (Gly-Gly-Gly-Gly-Ser)$_2$ (SEQ ID NO:8), Glu Ser Gly Arg Ser Gly Gly Gly Gly Ser Gly Gly Gly Gly Ser (SEQ ID NO: 9), Glu Gly Lys Ser Ser Gly Ser Gly Ser Glu Ser Lys Ser Thr (SEQ ID NO: 10), Glu Gly Lys Ser Ser Gly Ser Gly Ser Glu Ser Lys Ser Thr Gln (SEQ ID NO: 11), Glu Gly Lys Ser Ser Gly Ser Gly Ser Glu Ser Lys Val Asp (SEQ ID NO: 12), Gly Ser Thr Ser Gly Ser Gly Lys Ser Ser Glu Gly Lys Gly (SEQ ID NO: 13), Lys Glu Ser Gly Ser Val Ser Ser Glu Gln Leu Ala Gln Phe Arg Ser Leu Asp (SEQ ID NO: 14), and Glu Ser Gly Ser Val Ser Ser Glu Glu Leu Ala Phe Arg Ser Leu Asp (SEQ ID NO: 15). Examples of shorter linkers include fragments of the above linkers, and examples of longer linkers include combinations of the linkers above, combinations of fragments of the linkers above, and combinations of the linkers above with fragments of the linkers above.

As used herein the term "properly folded polypeptide" includes polypeptides (e.g., Anti-PrP$^c$ antagonist antibodies) in which all of the functional domains comprising the polypeptide are distinctly active. As used herein, the term "improperly folded polypeptide" includes polypeptides in which at least one of the functional domains of the polypeptide is not active. In one embodiment, a properly folded polypeptide comprises polypeptide chains linked by at least one disulfide bond and, conversely, an improperly folded polypeptide comprises polypeptide chains not linked by at least one disulfide bond.

As used herein the term "engineered" includes manipulation of nucleic acid or polypeptide molecules by synthetic means (e.g. by recombinant techniques, in vitro peptide synthesis, by enzymatic or chemical coupling of peptides or some combination of these techniques).

The term "expression" as used herein refers to a process by which a gene produces a biochemical, for example, an RNA or polypeptide. The process includes any manifestation of the functional presence of the gene within the cell including, without limitation, gene knockdown as well as both transient expression and stable expression. It includes without limitation transcription of the gene into messenger RNA (mRNA), transfer RNA (tRNA), small hairpin RNA (shRNA), small interfering RNA (siRNA) or any other RNA product and the translation of such mRNA into polypeptide(s). If the final desired product is biochemical, expression includes the creation of that biochemical and any precursors.

The term "RNA interference" or "RNAi" refers to the silencing or decreasing of gene expression by siRNAs. It is the process of sequence-specific, post-transcriptional gene silencing in animals and plants, initiated by siRNA that is homologous in its duplex region to the sequence of the silenced gene. The gene may be endogenous or exogenous to the organism, present integrated into a chromosome or present in a transfection vector that is not integrated into the genome. The expression of the gene is either completely or partially inhibited. RNAi may also be considered to inhibit the function of a target RNA; the function of the target RNA may be complete or partial.

As used herein, the terms "treat" or "treatment" refer to both therapeutic treatment and prophylactic or preventative measures, wherein the object is to prevent or slow down (lessen) an undesired physiological change or disorder, such as the progression of Alzheimer's disease. Beneficial or desired clinical results may include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. Any particular treatment regimen may provide one or more such clinical results in one or more patients, and need not provide all such clinical results. "Treatment" can also mean prolonging survival as compared to expected survival if not receiving treatment. Those in need of treatment include those already with the condition or disorder as well as those prone to have the condition or disorder or those in which the condition or disorder is to be prevented.

By "subject" or "individual" or "animal" or "patient" or "mammal," is meant any subject, particularly a mammalian subject, for whom diagnosis, prognosis, or therapy is desired. Mammalian subjects include, but are not limited to, humans, domestic animals, farm animals, zoo animals, sport animals, pet animals such as dogs, cats, guinea pigs, hamsters, rabbits, rats, mice, horses, cattle, cows; primates such as apes, monkeys, orangutans, and chimpanzees; canids such as dogs and wolves; felids such as cats, lions, and tigers; equids such as horses, donkeys, and zebras; food animals such as cows, pigs, and sheep; ungulates such as deer and giraffes; and so on. In certain embodiments, the mammal is a human subject.

As used herein, phrases such as "a subject that would benefit from administration of a $PrP^c$ antagonist polypeptide or polypeptide fragment of the present invention" and "an animal in need of treatment" includes subjects, such as mammalian subjects, that would benefit from administration of a $PrP^c$ antagonist polypeptide or polypeptide fragment of the present invention used, e.g., for detection (e.g., for a diagnostic procedure) and/or for treatment, i.e., palliation or prevention of a disease such as Alzheimer's disease, with a $PrP^c$ antagonist polypeptide or polypeptide fragment of the present invention. As described in more detail herein, the polypeptide or polypeptide fragment can be used in unconjugated form or can be conjugated, e.g., to a drug, prodrug, or an isotope.

As used herein, a "therapeutically effective amount" refers to an amount effective, at dosages and for periods of time necessary, to achieve a desired therapeutic result. A therapeutic result may be, e.g., lessening of symptoms, prolonged survival, improved mobility, and the like. A therapeutic result need not be a "cure".

As used herein, a "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

As used herein, a $PrP^c$ antagonist may be any molecule which interferes with ability of the $PrP^c$ to negatively regulate hippocampal long-term potentiation and spatial memory.

Cellular Prion Protein (PrP) Polypeptides

The present invention is directed to the use of certain $PrP^c$ antagonist polypeptides and polypeptide fragments for inhibiting suppression of long term potentiation, improving/increasing acute memory retention improving/increasing spatial memory performance, or treating diseases associated with $PrP^c$ binding, expression and signaling.

Full-length Prion protein (PrP) consists of a signal sequence, a N-terminal octapeptide repeat domain, a central domain which includes a charge cluster and a segment with hydrophobic character, a globular C-terminal domain and a GPI anchor. PrP is also known in the art by the names PrP27-30, PrP33-35C, ASCR, and CD230 antigen.

Different forms of PrP have been identified in the nervous system. The usual cellular form is called $PrP^c$. Another form, $PrP^{Sc}$, has a different 3-dimensional structure and has been associated with inherited, sporadic (non-inherited), and infectious disorders of the brain and nervous system. In a process that is not fully understood, $PrP^c$ can transform into the abnormal $PrP^{Sc}$. This abnormal protein can further promote the transformation of $PrP^c$ into $PrP^{Sc}$, leading to transmissible spongiform encephalopathy.

The nucleic acid sequence of the human PrP mRNA is available under GenBank Accession Number M13899, and is presented herein as SEQ ID NO:1:

```
  1 cggcgccgcg agcttctcct ctcctcacga ccgaggcaga
    gcagtcatta tggcgaacct
 61 tggctgctgg atgctggttc tctttgtggc cacatggagt
    gacctgggcc tctgcaagaa
121 gcgcccgaag cctggaggat ggaacactgg gggcagccga
    tacccggggc agggcagccc
181 tggaggcaac cgctacccac ctcagggcgg tggtggctgg
    gggcagcctc atggtggtgg
241 ctgggggcag cctcatggtg gtggctgggg gcagccccat
    ggtggtggct ggggacagcc
301 tcatggtggt ggctggggtc aaggaggtgg cacccacagt
    cagtggaaca gccgagtaa
361 gccaaaaacc aacatgaagc acatggctgg tgctgcagca
    gctggggcag tggtggggggg
421 ccttggcggc tacatgctgg gaagtgccat gagcaggccc
    atcatacatt tcggcagtga
481 ctatgaggac cgttactatc gtgaaaacat gcaccgttac
    cccaaccaag tgtactacag
541 gcccatggat gagtacagca accagaacaa ctttgtgcac
    gactgcgtca atatcacaat
601 caagcagcac acggtcacca caaccaccaa gggggagaac
    ttcaccgaga ccgacgttaa
661 gatgatggag cgcgtggttg agcagatgtg tatcacccag
    tacgagaggg aatctcaggc
721 ctattaccag agaggatcga gcatggtcct cttctcctct
    ccacctgtga tcctcctgat
781 ctctttcctc atcttcctga tagtgggatg aggaaggtct
    tcctgttttc accatctttc
841 taatcttttt ccagcttgag ggaggcggta tccacctgca
    gccctttag tggtggtgtc
901 tcactctttc ttctctcttt gtcccggata ggctaatcaa
    tacccttggc actgatgggc
961 actggaaaac atagagtaga cctgagatgc tggtcaagcc
    cccttttgatt gagttcatca
```

```
1021 tgagccgttg ctaatgccag gccagtaaaa gtataacagc
     aaataaccat tggttaatct
1081 ggacttattt ttggacttag tgcaacaggt tgaggctaaa
     acaaatctca gaacagtctg
1141 aaatacctt gcctggatac ctctggctcc ttcagcagct
     agagctcagt atactaatgc
1201 cctatcttag tagagatttc atagctattt agagatattt
     tccattttaa gaaaacccga
1261 caacatttct gccaggtttg ttaggaggcc acatgatact
     tattcaaaaa aatcctagag
1321 attcttagct cttgggatgc aggctcagcc cgctggagca
     tgagctctgt gtgtaccgag
1381 aactggggtg atgttttact tttcacagta tgggctacac
     agcagctgtt caacaagagt
1441 aaatattgtc acaacactga acctctggct agaggacata
     ttcacagtga acataactgt
1501 aacatatatg aaaggcttct gggacttgaa atcaaatgtt
     tgggaatggt gcccttggag
1561 gcaacctccc attttagatg tttaaaggac cctatatgtg
     gcattccttt ctttaaacta
1621 taggtaatta aggcagctga aaagtaaatt gccttctaga
     cactgaaggc aaatctcctt
1681 tgtccattta cctggaaacc agaatgattt tgacatacag
     gagagctgca gttgtgaaag
1741 caccatcatc atagaggatg atgtaattaa aaaatggtca
     gtgtgcaaag aaaagaactg
1801 cttgcatttc tttatttctg tctcataatt gtcaaaaacc
     agaattaggt caagttcata
1861 gtttctgtaa ttggcttttg aatcaaagaa tagggagaca
     atctaaaaaa tatcttaggt
1921 tggagatgac agaaatatga ttgatttgaa gtggaaaaag
     aaattctgtt aatgttaatt
1981 aaagtaaaat tattccctga attgtttgat attgtcacct
     agcagatatg tattactttt
2041 ctgcaatgtt attattggct tgcactttgt gagtatctat
     gtaaaaatat atatgtatat
2101 aaaatatata ttgcatagga cagacttagg agttttgttt
     agagcagtta acatctgaag
2161 tgtctaatgc attaactttt gtaaggtact gaatacttaa
     tatgtgggaa accctttgc
2221 gtggtcctta ggcttacaat gtgcactgaa tcgtttcatg
     taagaatcca aagtggacac
2281 cattaacagg tctttgaaat atgcatgtac tttatattt
     ctatatttgt aactttgcat
2341 gttcttgttt tgttatataa aaaaattgta aatgtttaat
     atctgactga aattaaacga
2401 gcgaagatga gcacc
```

In certain embodiments, the nucleotide sequence encoding the PrP polypeptide is altered, e.g., by codon optimization, without altering the amino acid sequence encoded thereby. For instance, the sequence may be altered for improved codon usage in a given species, to remove splice sites, or the remove restriction enzyme sites. Sequence optimizations are well known and routinely carried out by those of ordinary skill in the art.

The following polypeptide sequence was reported as the human PrP polypeptide and has the accession number AAA60182 in Genbank.

Full-Length Human PrP (SEQ ID NO:2):

```
  1 MANLGCWMLV LFVATWSDLG LCKKRPKPGG WNTGGSRYPG
    QGSPGGNRYP PQGGGGWGQP
 61 HGGGWGQPHG GGWGQPHGGG WGQPHGGGWG QGGGTHSQWN
    KPSKPKTNMK HMAGAAAAGA
121 VVGGLGGYML GSAMSRPIIH FGSDYEDRYY RENMHRYPNQ
    VYYRPMDEYS NQNNFVHDCV
181 NITIKQHTVT TTTKGENFTE TDVKMMERVV EQMCITQYER
    ESQAYYQRGS SMVLFSSPPV
241 ILLISFLIFL IVG
```

Variants of the human PrP polypeptide may include but are not limited to the following amino acid substitutions: P102L, P105L, A117V, M129V, G131V, N171S, D178N, V180I, T188K, T188R, E196K, F198S, E200K, D202N, V203I, R208H, V210I, E211Q, Q212P, Q217R, E219K, M232R, and P238S.

The nucleic acid sequence of the rat PrP mRNA is available under GenBank Accession Number BC072692, and is presented herein as SEQ ID NO:3:

```
  1 ttcaaaactg aaccatttca acccaactga agtattctgc
    cttcttagcg gtaccagtcc
 61 ggtttaggag agccaagccg actatcagcc atcatggcga
    accttggcta ctggctgctg
121 gccctctttg tgactacatg tactgatgtt ggcctctgca
    aaaagcggcc aaagcctgga
181 gggtggaaca ctggtggaag ccggtaccct gggcagggaa
    gccctggagg caaccgttac
```

```
 241 ccacctcaga gtggtggtac ctgggggcag ccccatggtg
     gtggctgggg acaacctcat
 301 ggtggtggct ggggacaacc tcatggtggt ggctggggtc
     agccccatgg cgggggctgg
 361 agtcaaggag ggggtaccca taatcagtgg aacaagccca
     gcaagccaaa aaccaacctc
 421 aagcatgtgg caggggctgc cgcagctggg gcagtagtgg
     ggggccttgg tggctacatg
 481 ttggggagtg ccatgagcag gcccatgctc cattttggca
     acgactggga ggaccgctac
 541 taccgagaaa acatgtaccg ttaccctaac caagtgtact
     acaggccggt ggatcagtac
 601 agcaaccaga acaacttcgt gcacgactgt gtcaatatca
     ccatcaagca gcatacagtc
 661 accaccacca ccaaggggga gaacttcacg gagaccgacg
     tgaagatgat ggagcgtgtg
 721 gtggagcaga tgtgcgtcac ccagtatcag aaggagtccc
     aggcctatta cgacgggaga
 781 agatctagcg ccgtgctttt ctcctcccct cctgtgatcc
     tcctcatctc cttcctcatc
 841 ttcctgatcg tgggatgagg aggccttcct gcttgttcct
     tctcattctc gtggtctagg
 901 ctgggggagg ggttacccac ctgtagctct ttcaattgag
     gtggtgtctc attcttgctt
 961 ctctttgtcc cccataggct aataccttg gcagtgatgg
     gtctggggaa atgtacagta
1021 gaccagatgc tattcgcttc agcgtccttt gattgagtcc
     atcatgggcc agggttaaca
1081 ccaggccagt aagaatataa caccaaataa ctgctggcta
     gtcagggctt tgttttggtc
1141 tactgagtaa atactgtgta acccctgaat tgtacccaga
     ggacatggtg acagagacac
1201 acataactta gtataggcaa agggttctat agccaaagaa
     gccactgtgt gggcatggca
1261 ccctggaaaa cagcctcccg cctgggatat ctagagcatc
     cacatgtgga attctttctt
1321 ttctaacata aaccatagct gattgaaggc aacaagaaaa
     agaatcaaat tatcctactg
1381 acattgaaag caaactgtgt tcattcccta ggcgctggaa
     tgattttag ccttggatta
1441 aaccaggaga ttttgactct gaggagaacc agcagtacaa
     aagcatggtc tcctgtgatg
1501 ggagagatgg tgaagggaca aaggcaagac ccctgcgttt
     cttcatttct gtctcataat
1561 tatcaagagc tagaattagg tcgtgcccta agtttctgta
     ctcgtatttg aactggacaa
1621 caaagagaca atctacaaat tctcttgggc tgcagaggag
     agaaataggc tccattccaa
1681 agtggaaaga gaaattctgc tagcattgtc taagtaaggc
     taacttttcc ttaaatcgct
1741 ttgtatttcc cccagcagac atcacaaccc tgtgatcggt
     tcagcctgca ccgcgggtgt
1801 tctgtgtaga atatataaat ataacttcaa gcttaggcct
     tctattttaa agcatctgaa
1861 gtgtggaacg cactggccgt tctgtgcagt actaagtgtg
     acccttgggc tttcaatgtg
1921 cactcggttc cgtatgattc caaagtagag ccctagctgg
     tcttcgaatc tgcatgtact
1981 tcacgttttc tatatttgta acttcgcatg tatttgtttt
     gtcatataaa aagtttataa
2041 atgtttgcta tctgactgac attaaataga agctatgatg
     agcaaaaaaa aaaaaaaaaa
2101 aaaaaaaaaa aaaaa
```

The following polypeptide sequence was reported as the rat PrP polypeptide and has the accession number NP_036763 in Genbank.

Full-Length Rat PrP (SEQ ID NO:4):

```
  1 MANLGYWLLA LFVTTCTDVG LCKKRPKPGG WNTGGSRYPG
    QGSPGGNRYP PQSGGTWGQP
 61 HGGGWGQPHG GGWGQPHGGG WGQPHGGGWS QGGGTHNQWN
    KPSKPKTNLK HVAGAAAAGA
121 VVGGLGGYML GSAMSRPMLH FGNDWEDRYY RENMYRYPNQ
    VYYRPVDQYS NQNNFVHDCV
181 NITIKQHTVT TTTKGENFTE TDVKMMERVV EQMCVTQYQK
    ESQAYYDGRR SSAVLFSSPP
241 VILLISFLIF LIVG
```

The nucleic acid sequence of the mouse PrP mRNA is available under GenBank Accession Number M13685, and is presented herein as SEQ ID NO:5:

```
  1 aattccttca gaactgaacc atttcaaccg agctgaagca
    ttctgccttc ctagtggtac
```

-continued

```
  61 cagtccaatt taggagagcc aagcagacta tcagtcatca
     tggcgaacct tggctactgg
 121 ctgctggccc tctttgtgac tatgtggact gatgtcggcc
     tctgcaaaaa gcggccaaag
 181 cctggagggt ggaacaccgg tggaagccgg tatcccgggc
     agggaagccc tggaggcaac
 241 cgttacccac ctcagggtgg cacctggggg cagccccacg
     gtggtggctg gggacaaccc
 301 catggggca gctggggaca acctcatggt ggtagttggg
     gtcagcccca tggcggtgga
 361 tggggccaag gaggggtac ccataatcag tggaacaagc
     ccagcaaacc aaaaaccaac
 421 ctcaagcatg tggcaggggc tgcggcagct ggggcagtag
     tggggggcct tggtggctac
 481 atgctgggga gcgccgtgag caggcccatg atccattttg
     gcaacgactg ggaggaccgc
 541 tactaccgtg aaaacatgta ccgctaccct aaccaagtgt
     actacaggcc agtggatcag
 601 tacagcaacc agaacaactt cgtgcacgac tgcgtcaata
     tcaccatcaa gcagcacacg
 661 gtcaccacca ccaccaaggg ggagaacttc accgagaccg
     atgtgaagat gatggagcgc
 721 gtggtggagc agatgtgcgt cacccagtac cagaaggagt
     cccaggccta ttacgacggg
 781 agaagatcca gcagcaccgt gctttctcc tcccctcctg
     tcatcctcct catctccttc
 841 ctcatcttcc tgatcgtggg atgagggagg ccttcctgct
     tgttccttcg cattctcgtg
 901 gtctaggctg ggggaggggt tatccacctg tagctctttc
     aattgaggtg gttctcattc
 961 ttgcttctct gtgtccccca taggctaata cccctggcac
     tgatgggccc tgggaaatgt
1021 acagtagacc agttgctctt tgcttcaggt cccctttgatg
     gagtctgtca tcagccagtg
1081 ctaacaccgg gccaataaga atataacacc aaataactgc
     tggctagttg gggctttgtt
1141 ttggtctagt gaataaatac tggtgtatcc cctgacttgt
     acccagagta caaggtgaca
1201 gtgacacatg taacttagca taggcaaagg gttctacaac
     caaagaagcc actgtttggg
1261 gatggcgccc tggaaaacag cctcccacct gggatagcta
     gagcatccac acgtggaatt
1321 ctttctttac taacaaacga tagctgattg aaggcaacaa
     aaaaaaaaaa atcaaattgt
1381 cctactgacg ttgaaagcaa acctttgttc attcccaggg
     cactagaatg atctttagcc
1441 ttgcttggat tgaactagga gatcttgact ctgaggagag
     ccagccctgt aaaaagcttg
1501 gtcctcctgt gacgggaggg atggttaagg tacaaaggct
     agaaacttga gtttcttcat
1561 ttctgtctca caattatcaa aagctagaat tagcttctgc
     cctatgtttc tgtacttcta
1621 tttgaactgg ataacagaga gacaatctaa acattctctt
     aggctgcaga taagagaagt
1681 aggctccatt ccaaagtggg aaagaaattc tgctagcatt
     gtttaaatca ggcaaaattt
1741 gttcctgaag ttgctttta ccccagcaga cataaactgc
     gatagcttca gcttgcactg
1801 tggattttct gtatagaata tataaaacat aacttcaagc
     ttatgtcttc ttttaaaac
1861 atctgaagta tgggacgccc tggccgttcc atccagtact
     aaatgcttac cgtgtgaccc
1921 ttgggctttc agcgtgcact cagttccgta ggattccaaa
     gcagacccct agctggtctt
1981 tgaatctgca tgtacttcac gttttctata tttgtaactt
     tgcatgtatt ttgttttgtc
2041 atataaaaag tttataaatg tttgctatca gactgacatt
     aaatagaagc tatgatg
```

The following polypeptide sequence was reported as the mouse PrP polypeptide and has the accession number NP_035300 in Genbank.

Full-Length Mouse PrP (SEQ ID NO:6):

```
   1 MANLGYWLLA LFVTMWTDVG LCKKRPKPGG WNTGGSRYPG
     QGSPGGNRYP PQGGTWGQPH
  61 GGGWGQPHGG SWGQPHGGSW GQPHGGGWGQ GGGTHNQWNK
     PSKPKTNLKH VAGAAAAGAV
 121 VGGLGGYMLG SAMSRPMIHF GNDWEDRYYR ENMYRYPNQV
     YYRPVDQYSN QNNFVHDCVN
 181 ITIKQHTVTT TTKGENFTET DVKMMERVVE QMCVTQYQKE
     SQAYYDGRRS SSTVLFSSPP
 241 VILLISFLIF LIVG
```

Variants of the human PrP polypeptide may include but are not limited to the following amino acid substitutions: L108F and T189V.

Different domains of $PrP^c$ are associated with various activities in vitro and in vivo. For example, the N-terminal octapeptide repeat domain (aa 60-95) mediates extracellular copper ion binding. Viles, et al., *Proc Natl Acad Sci USA* 96: 2042-2047 (1999). The unstructured central domain (aa 95-134) includes a charge cluster (aa 95-110) and a segment with hydrophobic character (aa 112-134). This central domain has been implicated in masking a neurodegenerative activity of $PrP^c$. Baumann, et al., *Embo J* 26: 538-547 (2007) and Li, et al., *Embo J* 26: 548-558 (2007). The C-terminal domain is globular (aa 134-231) (Riek, et al., *Nature* 382: 180-182 (1996)) and the protein is GPI anchored to the plasma membrane. As one of skill in the art will appreciate, the beginning and ending residues of the domains listed above may vary depending upon the computer modeling program used or the method used for determining the domain.

Treatment Methods Using Antagonists of $PrP^c$

One embodiment of the present invention provides methods for inhibiting suppression of long term potentiation in a mammal, the method comprising, consisting essentially of, or consisting of administering to the mammal an effective amount of a $PrP^c$ antagonist for example, (i) soluble $PrP^c$ polypeptides, (ii) anti-$PrP^c$ antibodies or fragments thereof, (iii) $PrP^c$ polynucleotide antagonists, (iv) $PrP^c$ aptamers or (v) a combination of two or more of said antagonists.

Additionally, the invention is directed to a method of improving/increasing acute memory retention in a mammal, the method comprising, consisting essentially of, or consisting of administering to the mammal an effective amount of a $PrP^c$ antagonist for example, (i) soluble $PrP^c$ polypeptides, (ii) anti-$PrP^c$ antibodies or fragments thereof, (iii) $PrP^c$ polynucleotide antagonists, (iv) $PrP^c$ aptamers or (v) a combination of two or more of said antagonists.

Also included in the present invention is a method of improving/increasing spatial memory performance in a mammal, the method comprising, consisting essentially of, or consisting of administering to the mammal an effective amount of a $PrP^c$ antagonist for example, (i) soluble $PrP^c$ polypeptides, (ii) anti-$PrP^c$ antibodies or fragments thereof, (iii) $PrP^c$ polynucleotide antagonists, (iv) $PrP^c$ aptamers or (v) a combination of two or more of said antagonists.

Further, the invention is directed to a method of treating Alzheimer's disease in a mammal, the method comprising, consisting essentially of, or consisting of administering to the mammal an effective amount of a $PrP^c$ antagonist for example, (i) soluble $PrP^c$ polypeptides, (ii) anti-$PrP^c$ antibodies or fragments thereof, (iii) $PrP^c$ polynucleotide antagonists, (iv) $PrP^c$ aptamers or (v) a combination of two or more of said antagonists.

Examples of $PrP^c$ antagonists for use in the present invention include but are not limited to a soluble $PrP^c$ polypeptide, an anti-$PrP^c$ antibody, $PrP^c$ antagonist polynucleotides or $PrP^c$ aptamers. Such $PrP^c$ antagonists further include functional fragments, variants, or derivatives of any of the above antagonist molecules.

A $PrP^c$ antagonist, e.g., soluble $PrP^c$ polypeptides, anti-$PrP^c$ antibodies and a $PrP^c$ antagonist polynucleotide or aptamer or fragments, variants, or derivatives of such molecules to be used in treatment methods disclosed herein, can be prepared and used as a therapeutic agent that stops, reduces, prevents, or inhibits the ability of $PrP^c$ to negatively regulate synaptic function.

In the methods of the present invention, the $PrP^c$ antagonist can be formulated for administration by a route selected from the group consisting of parenteral administration, subcutaneous administration, intravenous administration, intramuscular administration, intraperitoneal administration, transdermal administration, inhalational administration, buccal administration, oral administration, microinfusion administration, intrathecal administration, intracranial administration, intracerebroventricular administration, systemic administration, and peripheral administration. A $PrP^c$ antagonist can be administered directly into the central nervous system. $PrP^c$ antagonists can be administered systemically and/or peripherally.

In methods of the present invention, a $PrP^c$ antagonist can be administered via direct administration of a soluble $PrP^c$ polypeptide, an anti-$PrP^c$ antibody, a $PrP^c$ antagonist polynucleotide or aptamer to the patient. Alternatively, the $PrP^c$ antagonist can be administered via an expression vector, which expresses the specific $PrP^c$ antagonist, either in vivo or ex vivo. A $PrP^c$ antagonist can be administered e.g., directly into the central nervous system.

Diseases or disorders which may be treated or ameliorated by the methods of the present invention include diseases, disorders or injuries which relate to synaptic dysfunction, e.g., Alzheimer's disease.

$PrP^c$ Antagonists

A $PrP^c$ antagonist is an agent which blocks or inhibits the ability of Aβ-oligomers to bind to $PrP^c$; prevents or reduces the expression of $PrP^c$; or reduces or inhibits $PrP^c$ signaling, thereby inhibiting the ability of $PrP^c$ to negatively regulate synaptic function. As a result, $PrP^c$ antagonist increases, induces, or promotes synaptic function, hippocampal long-term potentiation, spatial memory and acute memory retention. $PrP^c$ antagonists for use in the methods disclosed herein include, but are not limited to a soluble $PrP^c$ polypeptide or fragment, variant, or derivative thereof; an anti-$PrP^c$ antibody or an antigen-binding fragment, variant, or derivative thereof; and $PrP^c$ antagonist polynucleotide, e.g., an antisense or RNAi polynucleotide or aptamer. $PrP^c$ antagonists further include polynucleotides which encode any of the $PrP^c$ antagonists listed above. $PrP^c$ antagonist can be administered alone or in combination with another $PrP^c$ antagonist listed herein, or with any other treatment which modulates synaptic function or is capable of treating Alzheimer's disease.

Soluble $PrP^c$ Polypeptides

A soluble $PrP^c$ polypeptide lacks a signal sequence and a functional GPI anchor (i.e., no GPI anchor or a GPI anchor that lacks the ability to efficiently associate to a cell membrane).

By "a $PrP^c$ reference amino acid sequence(s)," or "reference amino acid sequence(s)" is meant the specified sequence without the introduction of any amino acid substitutions. As one of ordinary skill in the art would understand, if there are no substitutions, the "isolated polypeptide" of the invention comprises an amino acid sequence which is identical to the reference amino acid sequence.

Soluble $PrP^c$ polypeptides for use in the methods of the present invention include but are not limited to the following reference amino acid sequences: (a) amino acid residues X to Y of SEQ ID NOs: 2, 4 or 6 wherein X is any integer from 20-25 and Y is any integer from 225-235; (b) amino acid residues $X_1$ to $Y_1$ of SEQ ID NOs: 2, 4 or 6, wherein $X_1$ is any integer from 90-100 and $Y_1$ is any integer from 105-115; (c) amino acid residues $X_2$ to $Y_2$ of SEQ ID NOs: 2, 4 or 6, wherein $X_2$ is any integer from 25-40 and $Y_1$ is any integer from 100-112; and (d) amino acid residues $X_2$ to $Y_3$ of SEQ ID NOs: 2, 4 or 6, wherein $Y_3$ is any integer from 120-130.

Soluble $PrP^c$ polypeptides for use in the methods of the present invention include but are not limited to the following reference amino acid sequences: amino acids 23 to 230 of SEQ ID NOs:2, 4 or 6; amino acids 95-110 of SEQ ID NOs:2, 4 or 6; amino acids 32-106 of SEQ ID NOs:2, 4 or 6; and amino acids 32-121 of SEQ ID NOs:2, 4 or 6. Corresponding fragments of soluble PrP$^c$ polypeptides at least 70%, 75%, 80%, 85%, 90%, or 95% identical to the soluble PrP$^c$ polypeptides described herein are also contemplated.

In some embodiments, amino acid substitutions can be made in the PrP$^c$ polypeptides. Which different amino acid is used depends on a number of criteria, for example, the effect of the substitution on the conformation of the polypeptide fragment, the charge of the polypeptide fragment, or the hydrophilicity of the polypeptide fragment. Making such substitutions through engineering of a polynucleotide encoding the polypeptide fragment is well within the routine expertise of one of ordinary skill in the art.

A soluble PrP$^c$ polypeptide can comprise a fragment of at least six, e.g., ten, fifteen, twenty, twenty-five, thirty, forty, fifty, sixty, seventy, one hundred, or more amino acids of SEQ ID NO:2, SEQ ID NO:4, SEQ ID NO:6, respectively. In addition, a soluble PrP$^c$ polypeptide may comprise at least one, e.g., five, ten, fifteen or twenty conservative amino acid substitutions.

As known in the art, "sequence identity" between two polypeptides is determined by comparing the amino acid sequence of one polypeptide to the sequence of a second polypeptide. When discussed herein, whether any particular polypeptide is at least about 70%, 75%, 80%, 85%, 90% or 95% identical to another polypeptide can be determined using methods and computer programs/software known in the art such as, but not limited to, the BESTFIT program (Wisconsin Sequence Analysis Package, Version 8 for Unix, Genetics Computer Group, University Research Park, 575 Science Drive, Madison, Wis. 53711). BESTFIT uses the local homology algorithm of Smith and Waterman, Advances in Applied Mathematics 2:482-489 (1981), to find the best segment of homology between two sequences. When using BESTFIT or any other sequence alignment program to determine whether a particular sequence is, for example, 95% identical to a reference sequence according to the present invention, the parameters are set, of course, such that the percentage of identity is calculated over the full length of the reference polypeptide sequence and that gaps in homology of up to 5% of the total number of amino acids in the reference sequence are allowed.

Soluble PrP$^c$ polypeptides for use in the methods of the present invention may include any combination of two or more soluble PrP$^c$ polypeptides. Accordingly, soluble PrP$^c$ polypeptide dimers, either homodimers or heterodimers, are contemplated. Two or more soluble PrP$^c$ polypeptides as described herein may be directly connected, or may be connected via a suitable peptide linker. Such peptide linkers are described elsewhere herein.

Accordingly, methods described herein that use PrP$^c$ polypeptides, and in particular human PrP$^c$, are not limited to the use of SEQ ID NOs:2, 4 or 6. Such polypeptides can be readily assayed for biological activity, e.g., for the ability to affect synaptic function.

Soluble PrP$^c$ polypeptides for use in the methods of the present invention described herein may be cyclic. Cyclization of the soluble PrP$^c$ polypeptides reduces the conformational freedom of linear peptides and results in a more structurally constrained molecule. Many methods of peptide cyclization are known in the art. For example, "backbone to backbone" cyclization by the formation of an amide bond between the N-terminal and the C-terminal amino acid residues of the peptide. The "backbone to backbone" cyclization method includes the formation of disulfide bridges between two omega-thio amino acid residues (e.g. cysteine, homocysteine). Certain soluble PrP$^c$ peptides of the present invention include modifications on the N- and C-terminus of the peptide to form a cyclic PrP$^c$ polypeptide. Such modifications include, but are not limited to, cysteine residues, acetylated cysteine residues cysteine residues with a NH$_2$ moiety and biotin. Other methods of peptide cyclization are described in Li & Roller. Curr. Top. Med. Chem. 3:325-341 (2002), which is incorporated by reference herein in its entirety.

Fusion Proteins and Conjugates

Some embodiments of the invention involve the use of a PrP$^c$ antagonist polypeptide, wherein the PrP$^c$ antagonist polypeptide moiety is fused to a heterologous polypeptide moiety at the N- or C-terminus to form a fusion protein. Such fusion proteins can be used to accomplish various objectives, e.g., increased serum half-life, improved bioavailability, in vivo targeting to a specific organ or tissue type, improved recombinant expression efficiency, improved host cell secretion, ease of purification, and higher avidity. Depending on the objective(s) to be achieved, the heterologous moiety can be inert or biologically active. Also, it can be chosen to be stably fused to the PrP$^c$ antagonist polypeptide, aptamer or antibody or to be cleavable, in vitro or in vivo. Heterologous moieties to accomplish different objectives are known in the art.

In some embodiments, the heterologous polypeptide is an immunoglobulin constant domain. In some embodiments, the immunoglobulin constant domain is a heavy chain constant domain. In some embodiments, the heterologous polypeptide is an Fc fragment. In some embodiments, the Fc is joined to the C-terminal end of the PrP$^c$ antagonist of the invention. In some embodiments, the fusion PrP$^c$ antagonist protein is a dimer. The invention further encompasses variants, analogs, or derivatives of polypeptide fragments as described above.

PrP$^c$ antagonist aptamers and antibodies for use in the treatment methods disclosed herein may also be recombinantly fused to a heterologous polypeptide at the N- or C-terminus or chemically conjugated (including covalent and non-covalent conjugations) to polypeptides or other compositions. For example, PrP$^c$ antagonist aptamers and antibodies may be recombinantly fused or conjugated to molecules useful as labels in detection assays and effector molecules such as heterologous polypeptides, drugs, radionuclides, or toxins. See, e.g., PCT publications WO 92/08495; WO 91/14438; WO 89/12624; U.S. Pat. No. 5,314,995; and EP 396,387.

PrP$^c$ antagonist polypeptides, aptamers, and antibodies for use in the treatment methods disclosed herein include derivatives that are modified, i.e., by the covalent attachment of any type of molecule such that covalent attachment does not prevent the PrP$^c$ antagonist polypeptide, aptamer, or antibody from inhibiting the biological function of the PrP$^c$. For example, but not by way of limitation, the PrP$^c$ antagonist polypeptides, aptamers and antibodies of the present invention may be modified e.g., by glycosylation, acetylation, pegylation, phosphylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

The PrP$^c$ antagonist polypeptides, aptamers and antibodies for use in the treatment methods disclosed herein can be composed of amino acids joined to each other by peptide bonds or modified peptide bonds, i.e., peptide isosteres, and may contain amino acids other than the 20 gene-encoded amino acids. PrP$^c$ antagonist polypeptides, aptamers and antibodies may be modified by natural processes, such as post-translational processing, or by chemical modification techniques which are well known in the art. Such modifications are well described in basic texts and in more detailed monographs, as well as in a voluminous research literature. Modifications can occur anywhere in the PrP$^c$ antagonist polypeptide, aptamer or antibody, including the peptide backbone, the amino acid side-chains and the amino or carboxyl termini, or on moieties such as carbohydrates. It will be appreciated that the same type of modification may be present in the same or varying degrees at several sites in a given PrP$^c$ antagonist polypeptide, aptamer or antibody. Also, a given PrP$^c$ antagonist polypeptide, aptamer or antibody may contain many types of modifications. PrP$^c$ antagonist polypeptides, aptamers or antibodies may be branched, for example, as a result of ubiquitination, and they may be cyclic, with or without branching. Cyclic, branched, and branched cyclic PrP$^c$ antagonist polypeptides, aptamers and antibodies may result from posttranslational natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, *Proteins—Structure And Molecular Properties*, T. E. Creighton, W. H. Freeman and Company, New York 2nd Ed., (1993); *Posttranslational Covalent Modification Of Proteins*, B. C. Johnson, Ed., Academic Press, New York, pgs. 1-12 (1983); Seifter et al., *Meth Enzymol* 182:626-646 (1990); Rattan et al., *Ann NY Acad Sci* 663:48-62 (1992)).

As an alternative to expression of the PrP$^c$ antagonist fusion polypeptide, aptamer or antibody, a chosen heterologous moiety can be preformed and chemically conjugated to the antagonist polypeptide, aptamer or antibody. In most cases, a chosen heterologous moiety will function similarly, whether fused or conjugated to the PrP$^c$ antagonist polypeptide, aptamer or antibody. Therefore, in the following discussion of heterologous amino acid sequences, unless otherwise noted, it is to be understood that the heterologous sequence can be joined to the PrP$^c$ antagonist polypeptide, aptamer or antibody in the form of a fusion protein or as a chemical conjugate.

In certain embodiments, PrP$^c$ antagonist polypeptides, aptamers, antibodies and antibody fragments thereof for use in the methods of the present invention further comprise a targeting moiety. Targeting moieties include a protein or a peptide which directs localization to a certain part of the body, for example, to the brain or compartments therein. In certain embodiments, PrP$^c$ antagonist polypeptides, aptamers, antibodies or antibody fragments thereof for use in the methods of the present invention are attached or fused to a brain targeting moiety. The brain targeting moieties are attached covalently (e.g., direct, translational fusion, or by chemical linkage either directly or through a spacer molecule, which can be optionally cleavable) or non-covalently attached (e.g., through reversible interactions such as avidin:biotin, protein A:IgG, etc.). In other embodiments, the PrP$^c$ antagonist polypeptides, aptamers, antibodies or antibody fragments thereof for use in the methods of the present invention thereof are attached to one more brain targeting moieties. In additional embodiments, the brain targeting moiety is attached to a plurality of PrP$^c$ antagonist polypeptides, aptamers, antibodies or antibody fragments thereof for use in the methods of the present invention.

A brain targeting moiety associated with a PrP$^c$ antagonist polypeptide, aptamer, antibody or antibody fragment thereof enhances brain delivery of such PrP$^c$ antagonist polypeptide, antibody or antibody fragment thereof. A number of polypeptides have been described which, when fused to a protein or therapeutic agent, delivers the protein or therapeutic agent through the blood brain barrier (BBB). Non-limiting examples include the single domain antibody FC5 (Abulrob et al. (2005) *J. Neurochem.* 95, 1201-1214); mAB 83-14, a monoclonal antibody to the human insulin receptor (Pardridge et al. (1995) *Pharmacol. Res.* 12, 807-816); the B2, B6 and B8 peptides binding to the human transferrin receptor (hTfR) (Xia et al. (2000) *J. Virol.* 74, 11359-11366); the OX26 monoclonal antibody to the transferrin receptor (Pardridge et al. (1991) *J. Pharmacol. Exp. Ther.* 259, 66-70); diptheria toxin conjugates (see, for e.g., Gaillard et al., *International Congress Series* 1277:185-198 (2005); and SEQ ID NOs: 1-18 of U.S. Pat. No. 6,306,365. The contents of the above references are incorporated herein by reference in their entirety.

Enhanced brain delivery of a PrP$^c$ composition is determined by a number of means well established in the art. For example, administering to an animal a radioactively, enzymatically or fluorescently labeled PrP$^c$ antagonist polypeptide, aptamer, antibody or antibody fragment thereof linked to a brain targeting moiety; determining brain localization; and comparing localization with an equivalent radioactively, enzymatically or fluorescently labeled PrP$^c$ antagonist polypeptide, aptamer, antibody or antibody fragment thereof that is not associated with a brain targeting moiety. Other means of determining enhanced targeting are described in the above references.

Fc Fusion Proteins

In certain embodiments, a soluble PrP$^c$ antagonist polypeptide is fused to a hinge and Fc region, i.e., the C-terminal portion of an Ig heavy chain constant region. In some embodiments, amino acids in the hinge region may be substituted with different amino acids. Exemplary amino acid substitutions for the hinge region according to these embodiments include substitutions of individual cysteine residues in the hinge region with different amino acids. Any different amino acid may be substituted for a cysteine in the hinge region. Amino acid substitutions for the amino acids of the polypeptides of the invention and the reference amino acid sequence can include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Typical amino acids to substitute for cysteines in the reference amino acid include alanine, serine, threonine, in particular, serine and alanine. Making such substitutions through engineering of a polynucleotide encoding the polypeptide fragment is well within the routine expertise of one of ordinary skill in the art.

Potential advantages of a Fc fusion include solubility, in vivo stability, and multivalency, e.g., dimerization. The Fc region used can be an IgA, IgD, or IgG Fc region (hinge—$C_H2$-$C_H3$). Alternatively, it can be an IgE or IgM Fc region (hinge—$C_H2$-$C_H3$-$C_H4$). An IgG Fc region is generally used, e.g., an IgG1 Fc region or IgG4 Fc region. In one embodiment, a sequence beginning in the hinge region just upstream of the papain cleavage site which defines IgG Fc chemically (i.e. residue 216, taking the first residue of heavy chain constant region to be 114 according to the Kabat system), or analogous sites of other immunoglobulins is used in the fusion. The precise site at which the fusion is made is not critical; particular sites are well known and may be selected in order to optimize the biological activity, secretion, or binding characteristics of the molecule. Materials and methods for constructing and expressing DNA encoding Fc fusions are known in the art and can be applied to obtain soluble protein fusions without undue experimentation. Some embodiments of the invention employ a $PrP^c$ antagonist fusion protein such as those described in Capon et al., U.S. Pat. Nos. 5,428,130 and 5,565,335.

The signal sequence is a polynucleotide that encodes an amino acid sequence that initiates transport of a protein across the membrane of the endoplasmic reticulum. Signal sequences useful for constructing a fusion protein include antibody light chain signal sequences, e.g., antibody 14.18 (Gillies et.al., 1989, *J. Immunol. Meth.,* 125:191-202), antibody heavy chain signal sequences, e.g., the MOPC141 antibody heavy chain signal sequence (Sakano et al., 1980, *Nature* 286:5774). Alternatively, other signal sequences can be used. See, for example, Watson, 1984, *Nucleic Acids Research* 12:5145). The signal peptide is usually cleaved in the lumen of the endoplasmic reticulum by signal peptidases. This results in the secretion of a fusion protein containing the Fc region and the $PrP^c$ antagonist.

In some embodiments the DNA sequence encodes a proteolytic cleavage site between the secretion cassette and $PrP^c$ antagonist. A cleavage site provides for the proteolytic cleavage of the encoded fusion protein, thus separating the Fc domain from the target protein. Useful proteolytic cleavage sites include amino acids sequences recognized by proteolytic enzymes such as trypsin, plasmin, thrombin, factor Xa, or enterokinase K.

The secretion cassette can be incorporated into a replicable expression vector. Useful vectors include linear nucleic acids, plasmids, phagemids, cosmids and the like. An exemplary expression vector is pdC, in which the transcription of the immunofusin DNA is placed under the control of the enhancer and promoter of the human cytomegalovirus. See, e.g., Lo et al., 1991, *Biochim. Biophys. Acta* 1088:712; and Lo et al., 1998, *Protein Engineering* 11:495-500. An appropriate host cell can be transformed or transfected with a DNA that encodes $PrP^c$ antagonist polypeptide, and is used for the expression and secretion of the $PrP^c$ antagonist polypeptide. Preferred host cells include immortal hybridoma cells, myeloma cells, 293 cells, Chinese hamster ovary (CHO) cells, Hela cells, and COS cells.

Certain sites preferably can be deleted from the Fc region during the construction of the secretion cassette. For example, since coexpression with the light chain is unnecessary, the binding site for the heavy chain binding protein, Bip (Hendershot et al., 1987, *Immunol. Today* 8:111-114), can be deleted from the CH2 domain of the Fc region of IgE, such that this site does not interfere with the efficient secretion of the immunofusin. Transmembrane domain sequences, such as those present in IgM, can be deleted.

The IgG1 Fc region is preferred. Alternatively, the Fc region of the other subclasses of immunoglobulin gamma (gamma-2, gamma-3 and gamma-4) can be used in the secretion cassette. The IgG1 Fc region of immunoglobulin gamma-1 is preferably used in the secretion cassette includes the hinge region (at least part), the $C_H2$ region, and all or part of the $C_H3$ region. In some embodiments, the Fc region of immunoglobulin gamma-1 is a $C_H2$-deleted-Fc, which includes part of the hinge region and the $C_H3$ region, but not the $C_H2$ region. A $C_H2$-deleted-Fc has been described by Gillies et al., 1990, *Hum. Antibod. Hybridomas,* 1:47. In some embodiments, the Fc regions of IgA, IgD, IgE, or IgM, are used.

$PrP^c$ antagonist fusion proteins can be constructed in several different configurations. In one configuration the C-terminus of a $PrP^c$ antagonist moiety is fused directly to the N-terminus of the Fc moiety. In a slightly different configuration, a short polypeptide, e.g., 2-10 amino acids, is incorporated into the fusion between the N-terminus of the $PrP^c$ antagonist moiety and the C-terminus of the Fc moiety. In the alternative configuration, the short polypeptide is incorporated into the fusion between the C-terminus of the $PrP^c$ antagonist polypeptide moiety and the N-terminus of the Fc moiety. Such a linker can provide conformational flexibility, which may improve biological activity in some circumstances. If a sufficient portion of the hinge region is retained in the Fc moiety, the $PrP^c$ antagonist-Fc fusion will dimerize, thus forming a divalent molecule. A homogeneous population of monomeric Fc fusions will yield monospecific, bivalent dimers. A mixture of two monomeric Fc fusions each having a different specificity will yield bispecific, bivalent dimers.

Other Fusion Proteins $PrP^c$ antagonist polypeptides can also be fused to heterologous peptides to facilitate purification or identification. For example, a histidine tag can be fused to the polypeptide to facilitate purification using commercially available chromatography media.

In some embodiments of the invention, a fusion construct is used to enhance the production of the $PrP^c$ antagonist moiety in bacteria. In such constructs a bacterial protein normally expressed and/or secreted at a high level is employed as the N-terminal fusion partner of the $PrP^c$ antagonist polypeptide. See, e.g., Smith et al., 1988 *Gene* 67:31; Hopp et al., 1988, *Biotechnology* 6:1204; La Vallie et al., 1993, *Biotechnology* 11:187.

By fusing a $PrP^c$ antagonist moiety at the amino and carboxy termini of a suitable fusion partner, bivalent or tetravalent forms of the $PrP^c$ antagonist polypeptide can be obtained. For example, a $PrP^c$ antagonist moiety can be fused to the amino and carboxy termini of an Ig moiety to produce a bivalent monomeric polypeptide containing two $PrP^c$ antagonist moieties. Upon dimerization of two of these monomers, by virtue of the Ig moiety, a tetravalent form of a $PrP^c$ antagonist protein is obtained. Such multivalent forms can be used to achieve increased binding affinity for the target. Multivalent forms of $PrP^c$ antagonists also can be obtained by placing $PrP^c$ antagonist moieties in tandem to form concatamers, which can be employed alone or fused to a fusion partner such as Ig or HSA.

Conjugated Polymers

Any of a number of cross-linkers that contain a corresponding amino reactive group and thiol reactive group can be used to link a $PrP^c$ antagonist to a second protein, such as serum albumin. Examples of suitable linkers include amine reactive cross linkers that insert a thiol reactive-maleimide, e.g., SMCC, AMAS, BMPS, MBS, EMCS, SMPB, SMPH, KMUS, and GMBS. Other suitable linkers insert a thiol reactive-haloacetate group, e.g., SBAP, SIA, STAB. Linkers that provide a protected or non-protected thiol for reaction with sulfhydryl groups to product a reducible linkage include SPDP, SMPT, SATA, and SATP. Such reagents are commercially available (e.g., Pierce Chemicals).

Conjugation does not have to involve the N-terminus of the PrP$^c$ antagonist or the thiol moiety on serum albumin. For example, the PrP$^c$ antagonist-albumin fusions can be obtained using genetic engineering techniques, wherein the PrP$^c$ antagonist moiety is fused to the serum albumin gene at its N-terminus, C-terminus, or both.

As an alternative to expression of a PrP$^c$ antagonist fusion protein, a chosen heterologous moiety can be preformed and chemically conjugated to the PrP$^c$ antagonist moiety. In most cases, a chosen heterologous moiety will function similarly, whether fused or conjugated to the PrP$^c$ antagonist moiety. Therefore, in the following discussion of heterologous amino acid sequences, unless otherwise noted, it is to be understood that the heterologous sequence can be joined to the PrP$^c$ antagonist moiety in the form of a fusion protein or as a chemical conjugate.

Pharmacologically active polypeptides such as a PrP$^c$ antagonist polypeptide often exhibit rapid in vivo clearance, necessitating large doses to achieve therapeutically effective concentrations in the body. In addition, polypeptides smaller than about 60 kDa potentially undergo glomerular filtration, which sometimes leads to nephrotoxicity. Fusion or conjugation of relatively small polypeptides such as PrP$^c$ antagonist fragments can be employed to reduce or avoid the risk of such nephrotoxicity. Various heterologous amino acid sequences, i.e., polypeptide moieties or "carriers," for increasing the in vivo stability, i.e., serum half-life, of therapeutic polypeptides are known. Examples include serum albumins such as, e.g., bovine serum albumin (BSA) and human serum albumin (HSA).

Due to its long half-life, wide in vivo distribution, and lack of enzymatic or immunological function, essentially full-length human serum albumin (HSA), or an HSA fragment, is a preferred heterologous moiety. Through application of methods and materials such as those taught in Yeh et al., 1992, *Proc. Natl. Acad. Sci. USA*, 89:1904-1908 and Syed et al., 1997, *Blood* 89:3243-3252, HSA can be used to form a PrP$^c$ antagonist fusion protein or conjugate that displays pharmacological activity by virtue of the PrP$^c$ antagonist moiety while displaying significantly increased, e.g., 10-fold to 100-fold higher, in vivo stability. Preferably, the C-terminus of the HSA is fused to the N-terminus of the PrP$^c$ antagonist moiety. Since HSA is a naturally secreted protein, the HSA signal sequence can be exploited to obtain secretion of the PrP$^c$ antagonist fusion protein into the cell culture medium, when the fusion protein is produced in a eukaryotic, e.g., mammalian, expression system.

Some embodiments of the invention involve a PrP$^c$ antagonist or polypeptide wherein one or more polymers are conjugated (covalently linked) to the PrP$^c$ antagonist polypeptide. Examples of polymers suitable for such conjugation include polypeptides (discussed above), sugar polymers and polyalkylene glycol chains. Typically, but not necessarily, a polymer is conjugated to the PrP$^c$ antagonist polypeptide for the purpose of improving one or more of the following: solubility, stability, or bioavailability. For example, PrP$^c$ antagonist polypeptides or antibodies may be recombinantly fused or conjugated to molecules useful as labels in detection assays and effector molecules such as heterologous polypeptides, drugs, radionuclides, or toxins. See, e.g., PCT publications WO 92/08495; WO 91/14438; WO 89/12624; U.S. Pat. No. 5,314,995; and EP 396,387.

A preferred class of polymer for conjugation to a PrP$^c$ antagonist polypeptide is a polyalkylene glycol. Polyethylene glycol (PEG) is particularly preferred. PEG moieties, e.g., 1, 2, 3, 4 or 5 PEG polymers, can be conjugated to each PrP$^c$ antagonist polypeptide to increase serum half life, as compared to the PrP$^c$ antagonist polypeptide alone. PEG moieties are non-antigenic and essentially biologically inert. PEG moieties used in the practice of the invention may be branched or unbranched.

The number of PEG moieties attached to the PrP$^c$ antagonist polypeptide and the molecular weight of the individual PEG chains can vary. In general, the higher the molecular weight of the polymer, the fewer polymer chains attached to the polypeptide. A PEG moiety can be linked to the PrP$^c$ antagonist polypeptide through any suitable, exposed reactive group on the polypeptide. The exposed reactive group(s) can be, for example, an N-terminal amino group or the epsilon amino group of an internal lysine residue, or both. An activated polymer can react and covalently link at any free amino group on the PrP$^c$ antagonist polypeptide. Free carboxylic groups, suitably activated carbonyl groups, hydroxyl, guanidyl, imidazole, oxidized carbohydrate moieties and mercapto groups of the PrP$^c$ antagonist (if available) also can be used as reactive groups for polymer attachment.

Preferably, in a conjugation reaction, from about 1.0 to about 10 moles of activated polymer per mole of polypeptide, depending on polypeptide concentration, is employed. Usually, the ratio chosen represents a balance between maximizing the reaction while minimizing side reactions (often non-specific) that can impair the desired pharmacological activity of the PrP$^c$ antagonist moiety. Preferably, at least 50% of the biological activity (as demonstrated, e.g., in any of the assays described herein or known in the art) of the PrP$^c$ antagonist polypeptide is retained, and most preferably nearly 100% is retained.

The polymer can be conjugated to the PrP$^c$ antagonist polypeptide using conventional chemistry. For example, a polyalkylene glycol moiety can be coupled to a lysine epsilon amino group of the PrP$^c$ antagonist polypeptide. Linkage to the lysine side chain can be performed with an N-hydroxylsuccinimide (NHS) active ester such as PEG succinimidyl succinate (SS-PEG) and succinimidyl propionate (SPA-PEG). Suitable polyalkylene glycol moieties include, e.g., carboxymethyl-NHS, norleucine-NHS, SC-PEG, tresylate, aldehyde, epoxide, carbonylimidazole, and PNP carbonate. These reagents are commercially available. Additional amine reactive PEG linkers can be substituted for the succinimidyl moiety. These include, e.g., isothiocyanates, nitrophenylcarbonates, epoxides, and benzotriazole carbonates. Conditions preferably are chosen to maximize the selectivity and extent or reaction. Such optimization of reaction conditions is within ordinary skill in the art.

PEGylation can be carried out by any of the PEGylation reactions known in the art. See, e.g., Focus on Growth Factors, 3: 4-10, 1992; published European patent applications EP 0 154 316 and EP 0 401 384. PEGylation may be carried out using an acylation reaction or an alkylation reaction with a reactive polyethylene glycol molecule (or an analogous reactive water-soluble polymer).

PEGylation by acylation generally involves reacting an active ester derivative of polyethylene glycol. Any reactive PEG molecule can be employed in the PEGylation. A preferred activated PEG ester is PEG esterified to N-hydroxysuccinimide (NHS). As used herein, "acylation" includes without limitation the following types of linkages between the therapeutic protein and a water soluble polymer such as PEG: amide, carbamate, urethane, and the like. See, *Bioconjugate*

*Chem.* 5: 133-140, 1994. Reaction parameters should be chosen to avoid temperature, solvent, and pH conditions that would damage or inactivate the PrP$^c$ antagonist polypeptide.

Preferably, the connecting linkage is an amide. Preferably, at least 95% of the resulting product is mono, di- or tri-PEGylated. However, some species with higher degrees of PEGylation may be formed in amounts depending on the specific reaction conditions used. Optionally, purified PEGylated species are separated from the mixture, particularly unreacted species, by conventional purification methods, including, e.g., dialysis, salting-out, ultrafiltration, ion-exchange chromatography, gel filtration chromatography, and electrophoresis.

PEGylation by alkylation generally involves reacting a terminal aldehyde derivative of PEG with a PrP$^c$ antagonist in the presence of a reducing agent. In addition, one can manipulate the reaction conditions to favor PEGylation substantially only at the N-terminal amino group of a PrP$^c$ antagonist (i.e., a mono-PEGylated protein). In either case of mono-PEGylation or poly-PEGylation, the PEG groups are preferably attached to the protein via a —C$_H$2-NH— group. With particular reference to the —CH2- group, this type of linkage is known as an "alkyl" linkage.

Derivatization via reductive alkylation to produce a mono-PEGylated product exploits differential reactivity of different types of primary amino groups (lysine versus the N-terminal) available for derivatization. The reaction is performed at a pH that allows one to take advantage of the pKa differences between the epsilon-amino groups of the lysine residues and that of the N-terminal amino group of the protein. By such selective derivatization, attachment of a water soluble polymer that contains a reactive group such as an aldehyde, to a protein is controlled: the conjugation with the polymer takes place predominantly at the N-terminus of the protein and no significant modification of other reactive groups, such as the lysine side chain amino groups, occurs.

The polymer molecules used in both the acylation and alkylation approaches are selected from among water soluble polymers. The polymer selected should be modified to have a single reactive group, such as an active ester for acylation or an aldehyde for alkylation, preferably, so that the degree of polymerization may be controlled as provided for in the present methods. An exemplary reactive PEG aldehyde is polyethylene glycol propionaldehyde, which is water stable, or mono C1-C10 alkoxy or aryloxy derivatives thereof (see, U.S. Pat. No. 5,252,714). The polymer may be branched or unbranched. For the acylation reactions, the polymer(s) selected should have a single reactive ester group. For reductive alkylation, the polymer(s) selected should have a single reactive aldehyde group. Generally, the water soluble polymer will not be selected from naturally-occurring glycosyl residues since these are usually made more conveniently by mammalian recombinant expression systems.

Methods for preparing a PEGylated PrP$^c$ antagonist generally includes the steps of (a) reacting a PrP$^c$ antagonist protein or polypeptide with polyethylene glycol (such as a reactive ester or aldehyde derivative of PEG) under conditions whereby the molecule becomes attached to one or more PEG groups, and (b) obtaining the reaction product(s). In general, the optimal reaction conditions for the acylation reactions will be determined case by case based on known parameters and the desired result. For example, the larger the ratio of PEG:protein, the greater the percentage of poly-PEGylated product.

Reductive alkylation to produce a substantially homogeneous population of mono-polymer/PrP$^c$ antagonist generally includes the steps of: (a) reacting a PrP$^c$ antagonist protein or polypeptide with a reactive PEG molecule under reductive alkylation conditions, at a pH suitable to permit selective modification of the N-terminal amino group of the PrP$^c$ antagonist; and (b) obtaining the reaction product(s).

For a substantially homogeneous population of mono-polymer/PrP$^c$ antagonist, the reductive alkylation reaction conditions are those that permit the selective attachment of the water soluble polymer moiety to the N-terminus of the PrP$^c$ antagonist. Such reaction conditions generally provide for pKa differences between the lysine side chain amino groups and the N-terminal amino group. For purposes of the present invention, the preferred pH is in the range of 3-9, preferably 3-6.

PrP$^c$ antagonist polypeptides can include a tag, e.g., a moiety that can be subsequently released by proteolysis. Thus, the lysine moiety can be selectively modified by first reacting a His-tag modified with a low molecular weight linker such as Traut's reagent (Pierce) which will react with both the lysine and N-terminus, and then releasing the his tag. The polypeptide will then contain a free SH group that can be selectively modified with a PEG containing a thiol reactive head group such as a maleimide group, a vinylsulfone group, a haloacetate group, or a free or protected SH.

Traut's reagent can be replaced with any linker that will set up a specific site for PEG attachment. For example, Traut's reagent can be replaced with SPDP, SMPT, SATA, or SATP (Pierce). Similarly one could react the protein with an amine reactive linker that inserts a maleimide (for example SMCC, AMAS, BMPS, MBS, EMCS, SMPB, SMPH, KMUS, or GMBS), a haloacetate group (SBAP, SIA, STAB), or a vinylsulfone group and react the resulting product with a PEG that contains a free SH.

In some embodiments, the polyalkylene glycol moiety is coupled to a cysteine group of the PrP$^c$ antagonist polypeptide. Coupling can be effected using, e.g., a maleimide group, a vinylsulfone group, a haloacetate group, or a thiol group.

Optionally, the PrP$^c$ antagonist polypeptide is conjugated to the polyethylene glycol moiety through a labile bond. The labile bond can be cleaved in, e.g., biochemical hydrolysis, proteolysis, or sulfhydryl cleavage. For example, the bond can be cleaved under in vivo (physiological) conditions.

The reactions may take place by any suitable method used for reacting biologically active materials with inert polymers, preferably at about pH 5-8, e.g., pH 5, 6, 7, or 8, if the reactive groups are on the alpha amino group at the N-terminus. Generally, the process involves preparing an activated polymer and thereafter reacting the protein with the activated polymer to produce the soluble protein suitable for formulation.

Antibodies or Antigen-Binding Fragments Thereof

PrP$^c$ antagonists for use in the methods of the present invention also include PrP$^c$ antagonist-specific antibodies or antigen-binding fragments, variants, or derivatives which are antagonists of PrP$^c$ activity. For example, binding of PrP$^c$ antibodies to PrP$^c$, as expressed on adult neurons, inhibits suppression of long term potentiation in a mammal, thereby improving/increasing acute memory retention and spatial memory performance, as well as treating diseases associated with these conditions.

As used herein, the term "antigen binding domain" includes a site that specifically binds an epitope on an antigen (e.g., an epitope of PrP$^c$). The antigen binding domain of an antibody typically includes at least a portion of an immunoglobulin heavy chain variable region and at least a portion of an immunoglobulin light chain variable region. The binding site formed by these variable regions determines the specificity of the antibody.

Certain antagonist antibodies for use in the methods described herein specifically or preferentially binds to a particular PrP$^c$ polypeptide fragment or domain. Such PrP$^c$ polypeptide fragments include, but are not limited to, a PrP$^c$ polypeptide comprising, consisting essentially of, or consisting of amino acid fragments of: about amino acid 95 to about amino acid 110 of SEQ ID NOs:2, 4 or 6, about amino acid 23 to about amino acid 230 of SEQ ID NOs:2, 4 or 6, about amino acid 32 to about amino acid 106 of SEQ ID NOs:2, 4 or 6, and about amino acid 32 to about amino acid 121 of SEQ ID NO:6, or a PrP$^c$ variant polypeptide at least 70%, 75%, 80%, 85%, 90%, or 95% identical to amino acid fragments of about amino acid 95 to about amino acid 110 of SEQ ID NOs:2, 4 or 6, about amino acid 23 to about amino acid 230 of SEQ ID NOs:2, 4 or 6, about amino acid 32 to about amino acid 106 of SEQ ID NOs:2, 4 or 6, and about amino acid 32 to about amino acid 121 of SEQ ID NOs:2, 4 or 6. Examples of preferred antibodies include but are not limited to 6D11 and 8G8. Pankiewicz et al., *Eur. J. Neurosci.* 23:2635-2647 (2006) and Krasemann S. et al. Induction of antibodies against human prion proteins (PrP) by DNA-mediated immunization of PrP 0/0 mice. *Journal of Immunological Methods* 199: 109-118 (1996). See also SPIbio product information sheet for anti-prion protein mAB 8G8 available at spibio.com.

In other embodiments, the present invention includes an antibody, or antigen-binding fragment, variant, or derivative thereof which specifically or preferentially binds to at least one epitope of PrP$^c$, where the epitope comprises, consists essentially of, or consists of at least about four to five amino acids of SEQ ID NOs:2, 4 or 6, at least seven, at least nine, or between at least about 15 to about 30 amino acids of SEQ ID NOs:2, 4 or 6. The amino acids of a given epitope of SEQ ID NOs:2, 4 or 6 as described may be, but need not be contiguous or linear. In certain embodiments, the at least one epitope of PrP$^c$ comprises, consists essentially of, or consists of a non-linear epitope formed by the extracellular domain of PrP$^c$ as expressed on the surface of a cell or as a soluble fragment, e.g., fused to an IgG Fc region. Thus, in certain embodiments the at least one epitope of PrP$^c$ comprises, consists essentially of, or consists of at least 4, at least 5, at least 6, at least 7, at least 8, at least 9, at least 10, at least 15, at least 20, at least 25, between about 15 to about 30, or at least 10, 15, 20, 25, 30, 35, 40, 45, 50, 55, 60, 65, 70, 75, 80, 85, 90, 95, or 100 contiguous or non-contiguous amino acids of SEQ ID NOs:2, 4 or 6, where non-contiguous amino acids form an epitope through protein folding.

In other embodiments, the present invention includes an antibody, or antigen-binding fragment, variant, or derivative thereof which specifically or preferentially binds to at least one epitope of PrP$^c$, where the epitope comprises, consists essentially of, or consists of, in addition to one, two, three, four, five, six or more contiguous or non-contiguous amino acids of SEQ ID NOs:2, 4 or 6 as described above, and an additional moiety which modifies the protein, e.g., a carbohydrate moiety may be included such that the PrP$^c$ antibody binds with higher affinity to modified target protein than it does to an unmodified version of the protein. Alternatively, the PrP$^c$ antibody does not bind the unmodified version of the target protein at all.

Any of the polynucleotides described above may further include additional nucleic acids, encoding, e.g., a signal peptide to direct secretion of the encoded polypeptide, antibody constant regions as described herein, or other heterologous polypeptides as described herein.

TABLE 13

| CDR Definitions[1] | | |
|---|---|---|
| | Kabat | Chothia |
| $V_H$ CDR1 | 31-35 | 26-32 |
| $V_H$ CDR2 | 50-65 | 52-58 |
| $V_H$ CDR3 | 95-102 | 95-102 |
| $V_L$ CDR1 | 24-34 | 26-32 |
| $V_L$ CDR2 | 50-56 | 50-52 |
| $V_L$ CDR3 | 89-97 | 91-96 |

[1]Numbering of all CDR definitions in Table 13 is according to the numbering conventions set forth by Kabat et al. (see below).

Kabat et al. also defined a numbering system for variable domain sequences that is applicable to any antibody. One of ordinary skill in the art can unambigously assign this system of "Kabat numbering" to any variable domain sequence, without reliance on any experimental data beyond the sequence itself. As used herein, "Kabat numbering" refers to the numbering system set forth by Kabat et al., U.S. Dept. of Health and Human Services, "Sequence of Proteins of Immunological Interest" (1983). Unless otherwise specified, references to the numbering of specific amino acid residue positions in an $PrP^c$ antibody or antigen-binding fragment, variant, or derivative thereof of the present invention are according to the Kabat numbering system.

In certain embodiments, an antibody, or antigen-binding fragment, variant, or derivative thereof of the invention binds specifically to at least one epitope of $PrP^c$ or fragment or variant described above, i.e., binds to such an epitope more readily than it would bind to an unrelated, or random epitope; binds preferentially to at least one epitope of $PrP^c$ or fragment, variant, or derivative described above, i.e., binds to such an epitope more readily than it would bind to a related, similar, homologous, or analogous epitope; competitively inhibits binding of a reference antibody which itself binds specifically or preferentially to a certain epitope of $PrP^c$ or fragment or variant described above; or binds to at least one epitope of $PrP^c$ or fragment or variant described above with an affinity characterized by a dissociation constant $K_D$ of less than about $5\times10^{-2}$ M, about $10^{-2}$ M, about $5\times10^{-3}$ M, about $10^{-3}$ M, about $5\times10^{-4}$ M, about $10^{-4}$ M, about $5\times10^{-5}$ M, about $10^{-5}$ M, about $5\times10^{-6}$ M, about $10^{-6}$ M, about $5\times10^{-7}$ M, about $10^{-7}$ M, about $5\times10^{-8}$ M, about $10^{-8}$ M, about $5\times10^{-9}$ M, about $10^{-9}$ M, about $5\times10^{-10}$ M, about $10^{-10}$ M, about $5\times10^{-11}$ M, about $10^{-11}$ M, about $5\times10^{-12}$ M, about $10^{-12}$ M, about $5\times10^{-13}$ M, about $10^{-13}$ M, about $5\times10^{-14}$ M, about $10^{-14}$ M, about $5\times10^{-15}$ M, or about $10^{-15}$ M. In a particular aspect, the antibody or fragment thereof preferentially binds to a human $PrP^c$ polypeptide or fragment thereof, relative to a murine $PrP^c$ polypeptide or fragment thereof.

As used in the context of antibody binding dissociation constants, the term "about" allows for the degree of variation inherent in the methods utilized for measuring antibody affinity. For example, depending on the level of precision of the instrumentation used, standard error based on the number of samples measured, and rounding error, the term "about $10^{-2}$ M" might include, for example, from 0.05 M to 0.005 M.

In specific embodiments, an antibody, or antigen-binding fragment, variant, or derivative thereof of the invention binds $PrP^c$ polypeptides or fragments or variants thereof with an off rate (k(off)) of less than or equal to $5\times10^{-2}$ $sec^{-1}$, $10^{-2}$ $sec^{-1}$, $5\times10^{-3}$ $sec^{-1}$ or $10^{-3}$ $sec^{-1}$. Alternatively, an antibody, or antigen-binding fragment, variant, or derivative thereof of the invention binds $PrP^c$ polypeptides or fragments or variants thereof with an off rate (k(off)) of less than or equal to $5\times10^{-4}$ $sec^{-1}$, $10^{-4}$ $sec^{-1}$, $5\times10^{-5}$ $sec^{-1}$, or $10^{-5}$ $sec^{-1}$ $5\times10^{-6}$ $sec^{-1}$, $10^{-6}$ $sec^{-1}$, $5\times10^{-7}$ $sec^{-1}$ or $10^{-7}$ $sec^{-1}$.

In other embodiments, an antibody, or antigen-binding fragment, variant, or derivative thereof of the invention binds $PrP^c$ polypeptides or fragments or variants thereof with an on rate (k(on)) of greater than or equal to $10^3$ $M^{-1}$ $sec^{-1}$, $5\times10^3$ $M^{-1}$ $sec^{-1}$, $10^4$ $M^{-1}$ $sec^{-1}$ or $5\times10^4$ $M^{-1}$ $sec^{-1}$. Alternatively, an antibody, or antigen-binding fragment, variant, or derivative thereof of the invention binds $PrP^c$ polypeptides or fragments or variants thereof with an on rate (k(on)) greater than or equal to $10^5$ $M^{-1}$ $sec^{-1}$, $5\times10^5$ $M^{-1}$ $sec^{-1}$, $10^6$ $M^{-1}$ $sec^{-1}$, or $5\times10^6$ $M^{-1}$ $sec^{-1}$.

In one embodiment, a $PrP^c$ antagonist for use in the methods of the invention is an antibody molecule, or immunospecific fragment thereof. Unless it is specifically noted, as used herein a "fragment thereof" in reference to an antibody refers to an immunospecific fragment, i.e., an antigen-specific fragment. In one embodiment, an antibody of the invention is a bispecific binding molecule, binding polypeptide, or antibody, e.g., a bispecific antibody, minibody, domain deleted antibody, or fusion protein having binding specificity for more than one epitope, e.g., more than one antigen or more than one epitope on the same antigen. In one embodiment, a bispecific antibody has at least one binding domain specific for at least one epitope on $PrP^c$. A bispecific antibody may be a tetravalent antibody that has two target binding domains specific for an epitope of $PrP^c$ and two target binding domains specific for a second target. Thus, a tetravalent bispecific antibody may be bivalent for each specificity.

In certain embodiments of the present invention comprise administration of a $PrP^c$ antagonist antibody, or immunospecific fragment thereof, in which at least a fraction of one or more of the constant region domains has been deleted or otherwise altered so as to provide desired biochemical characteristics such as reduced effector functions, the ability to non-covalently dimerize, increased ability to localize at the site of a neuron, reduced serum half-life, or increased serum half-life when compared with a whole, unaltered antibody of approximately the same immunogenicity. For example, certain antibodies for use in the treatment methods described herein are domain deleted antibodies which comprise a polypeptide chain similar to an immunoglobulin heavy chain, but which lack at least a portion of one or more heavy chain domains. For instance, in certain antibodies, one entire domain of the constant region of the modified antibody will be deleted, for example, all or part of the $C_H2$ domain will be deleted.

In certain $PrP^c$ antagonist antibodies or immunospecific fragments thereof for use in the therapeutic methods described herein, the Fc portion may be mutated to decrease effector function using techniques known in the art. For example, the deletion or inactivation (through point mutations or other means) of a constant region domain may reduce Fc receptor binding of the circulating modified antibody thereby increasing CNS localization, especially in neurons. In other cases it may be that constant region modifications consistent with the instant invention moderate complement binding and thus reduce the serum half life and nonspecific association of a conjugated cytotoxin. Yet other modifications of the constant region may be used to modify disulfide linkages or oligosaccharide moieties that allow for enhanced localization due to increased antigen specificity or antibody flexibility. The resulting physiological profile, bioavailability and other biochemical effects of the modifications, such as CNS localization, biodistribution and serum half-life, may easily be measured and quantified using well know immunological techniques without undue experimentation.

Modified forms of antibodies or immunospecific fragments thereof for use in the diagnostic and therapeutic methods disclosed herein can be made from whole precursor or parent antibodies using techniques known in the art. Exemplary techniques are discussed in more detail herein.

In certain embodiments both the variable and constant regions of the $PrP^c$ antagonist antibodies or immunospecific fragments thereof for use in the treatment methods disclosed herein are fully human. Fully human antibodies can be made using techniques that are known in the art and as described herein. For example, fully human antibodies against a specific antigen can be prepared by administering the antigen to a transgenic animal which has been modified to produce such antibodies in response to antigenic challenge, but whose endogenous loci have been disabled. Exemplary techniques that can be used to make such antibodies are described in U.S. Pat. Nos. 6,150,584; 6,458,592; 6,420,140. Other techniques are known in the art. Fully human antibodies can likewise be produced by various display technologies, e.g., phage display or other viral display systems, as described in more detail elsewhere herein.

$PrP^c$ antagonist antibodies or immunospecific fragments thereof for use in the methods disclosed herein can be made or manufactured using techniques that are known in the art. In certain embodiments, antibody molecules or fragments thereof are "recombinantly produced," i.e., are produced using recombinant DNA technology. Exemplary techniques for making antibody molecules or fragments thereof are discussed in more detail elsewhere herein.

In preferred embodiments, the $PrP^c$ antagonist antibody or immunospecific fragment thereof for use in the methods disclosed herein will not elicit a deleterious immune response in the animal to be treated, e.g., in a human. In one embodiment, the $PrP^c$ antagonist antibodies or immunospecific fragments thereof for use in the treatment methods disclosed herein may be modified to reduce their immunogenicity using art-recognized techniques. For example, antibodies can be humanized, primatized, deimmunized, or chimeric antibodies can be made. These types of antibodies are derived from a non-human antibody, typically a murine or primate antibody, that retains or substantially retains the antigen-binding properties of the parent antibody, but which is less immunogenic in humans. This may be achieved by various methods, including (a) grafting the entire non-human variable domains onto human constant regions to generate chimeric antibodies; (b) grafting at least a part of one or more of the non-human complementarity determining regions (CDRs) into a human framework and constant regions with or without retention of critical framework residues; or (c) transplanting the entire non-human variable domains, but "cloaking" them with a human-like section by replacement of surface residues. Such methods are disclosed in Morrison et al., *Proc. Natl. Acad. Sci.* 81:6851-6855 (1984); Morrison et al., *Adv. Immunol.* 44:65-92 (1988); Verhoeyen et al., *Science* 239:1534-1536 (1988); Padlan, *Molec. Immun.* 28:489-498 (1991); Padlan, *Molec. Immun.* 31:169-217 (1994), and U.S. Pat. Nos. 5,585,089, 5,693,761, 5,693,762, and 6,190,370, all of which are hereby incorporated by reference in their entirety.

De-immunization can also be used to decrease the immunogenicity of an antibody. As used herein, the term "de-immunization" includes alteration of an antibody to modify T cell epitopes (see, e.g., WO9852976A1, WO0034317A2). For example, $V_H$ and $V_L$ sequences from the starting antibody are analyzed and a human T cell epitope "map" from each V region showing the location of epitopes in relation to complementarity-determining regions (CDRs) and other key residues within the sequence. Individual T cell epitopes from the T cell epitope map are analyzed in order to identify alternative amino acid substitutions with a low risk of altering activity of the final antibody. A range of alternative $V_H$ and $V_L$ sequences are designed comprising combinations of amino acid substitutions and these sequences are subsequently incorporated into a range of binding polypeptides, e.g., $PrP^c$ antagonist antibodies or immunospecific fragments thereof for use in the methods disclosed herein, which are then tested for function. Typically, between 12 and 24 variant antibodies are generated and tested. Complete heavy and light chain genes comprising modified V and human C regions are then cloned into expression vectors and the subsequent plasmids introduced into cell lines for the production of whole antibody. The antibodies are then compared in appropriate biochemical and biological assays, and the optimal variant is identified.

$PrP^c$ antagonist antibodies or fragments thereof for use in the methods of the present invention may be generated by any suitable method known in the art. Polyclonal antibodies can be produced by various procedures well known in the art. For example, a $PrP^c$ polypeptide fragment can be administered to various host animals including, but not limited to, rabbits, mice, rats, etc. to induce the production of sera containing polyclonal antibodies specific for the antigen. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*. Such adjuvants are also well known in the art.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., *Antibodies: A Laboratory Manual*, Cold Spring Harbor Laboratory Press, 2nd ed. (1988); Hammerling et al., in: *Monoclonal Antibodies and T-Cell Hybridomas* Elsevier, N.Y., 563-681 (1981) (said references incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced. Thus, the term "monoclonal antibody" is not limited to antibodies produced through hybridoma technology. Monoclonal antibodies can be prepared using a wide variety of techniques known in the art including the use of hybridoma and recombinant and phage display technology.

Using art recognized protocols, in one example, antibodies are raised in mammals by multiple subcutaneous or intraperitoneal injections of the relevant antigen (e.g., purified $PrP^c$ antagonist antigens or cells or cellular extracts comprising such antigens) and an adjuvant. This immunization typically elicits an immune response that comprises production of antigen-reactive antibodies from activated splenocytes or lymphocytes. While the resulting antibodies may be harvested from the serum of the animal to provide polyclonal preparations, it is often desirable to isolate individual lymphocytes from the spleen, lymph nodes or peripheral blood to provide homogenous preparations of monoclonal antibodies (mAbs). Preferably, the lymphocytes are obtained from the spleen.

In this well known process (Kohler et al., *Nature* 256:495 (1975)) the relatively short-lived, or mortal, lymphocytes from a mammal which has been injected with antigen are fused with an immortal tumor cell line (e.g. a myeloma cell line), thus, producing hybrid cells or "hybridomas" which are both immortal and capable of producing the genetically coded antibody of the B cell. The resulting hybrids are segregated into single genetic strains by selection, dilution, and regrowth with each individual strain comprising specific genes for the formation of a single antibody. They produce antibodies which are homogeneous against a desired antigen and, in reference to their pure genetic parentage, are termed "monoclonal."

Hybridoma cells thus prepared are seeded and grown in a suitable culture medium that preferably contains one or more substances that inhibit the growth or survival of the unfused, parental myeloma cells. Those skilled in the art will appreciate that reagents, cell lines and media for the formation, selection and growth of hybridomas are commercially available from a number of sources and standardized protocols are well established. Generally, culture medium in which the hybridoma cells are growing is assayed for production of monoclonal antibodies against the desired antigen. Preferably, the binding specificity of the monoclonal antibodies produced by hybridoma cells is determined by in vitro assays such as immunoprecipitation, radioimmunoassay (RIA) or enzyme-linked immunoabsorbent assay (ELISA). After hybridoma cells are identified that produce antibodies of the desired specificity, affinity and/or activity, the clones may be subcloned by limiting dilution procedures and grown by standard methods (Goding, *Monoclonal Antibodies: Principles and Practice*, Academic Press, pp 59-103 (1986)). It will further be appreciated that the monoclonal antibodies secreted by the subclones may be separated from culture medium, ascites fluid or serum by conventional purification procedures such as, for example, protein-A, hydroxylapatite chromatography, gel electrophoresis, dialysis or affinity chromatography.

Antibody fragments that recognize specific epitopes may be generated by known techniques. For example, Fab and F(ab')2 fragments may be produced by proteolytic cleavage of immunoglobulin molecules, using enzymes such as papain (to produce Fab fragments) or pepsin (to produce F(ab')2 fragments). F(ab')2 fragments contain the variable region, the light chain constant region and the $C_H1$ domain of the heavy chain.

Those skilled in the art will also appreciate that DNA encoding antibodies or antibody fragments (e.g., antigen binding sites) may also be derived from antibody phage libraries. In a particular, such phage can be utilized to display antigen-binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Exemplary methods are set forth, for example, in EP 368 684 B1; U.S. Pat. No. 5,969, 108, Hoogenboom, H. R. and Chames, *Immunol. Today* 21:371 (2000); Nagy et al. *Nat. Med.* 8:801 (2002); Huie et al., *Proc. Natl. Acad. Sci. USA* 98:2682 (2001); Lui et al., *J. Mol. Biol.* 315:1063 (2002), each of which is incorporated herein by reference. Several publications (e.g., Marks et al., *Bio/Technology* 10:779-783 (1992)) have described the production of high affinity human antibodies by chain shuffling, as well as combinatorial infection and in vivo recombination as a strategy for constructing large phage libraries. In another embodiment, Ribosomal display can be used to replace bacteriophage as the display platform (see, e.g., Hanes et al., *Nat. Biotechnol.* 18:1287 (2000); Wilson et al., *Proc. Natl. Acad. Sci. USA* 98:3750 (2001); or Irving et al., *J. Immunol. Methods* 248:31 (2001)). In yet another embodiment, cell surface libraries can be screened for antibodies (Boder et al., *Proc. Natl. Acad. Sci. USA* 97:10701 (2000); Daugherty et al., *J. Immunol. Methods* 243:211 (2000)). Such procedures provide alternatives to traditional hybridoma techniques for the isolation and subsequent cloning of monoclonal antibodies.

In phage display methods, functional antibody domains are displayed on the surface of phage particles which carry the polynucleotide sequences encoding them. In particular, DNA sequences encoding $V_H$ and $V_L$ regions are amplified from animal cDNA libraries (e.g., human or murine cDNA libraries of lymphoid tissues) or synthetic cDNA libraries. In certain embodiments, the DNA encoding the $V_H$ and $V_L$ regions are joined together by an scFv linker by PCR and cloned into a phagemid vector (e.g., p CANTAB 6 or pComb 3 HSS). The vector is electroporated in *E. coli* and the *E. coli* is infected with helper phage. Phage used in these methods are typically filamentous phage including fd and M13 and the $V_H$ or $V_L$ regions are usually recombinantly fused to either the phage gene III or gene VIII. Phage expressing an antigen binding domain that binds to an antigen of interest (i.e., a $PrP^c$ polypeptide or a fragment thereof) can be selected or identified with antigen, e.g., using labeled antigen or antigen bound or captured to a solid surface or bead.

Additional examples of phage display methods that can be used to make the antibodies include those disclosed in Brinkman et al., *J. Immunol. Methods* 182:41-50 (1995); Ames et al., *J. Immunol. Methods* 184:177-186 (1995); Kettleborough et al., *Eur. J. Immunol.* 24:952-958 (1994); Persic et al., *Gene* 187:9-18 (1997); Burton et al., *Advances in Immunology* 57:191-280 (1994); PCT Application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria. For example, techniques to recombinantly produce Fab, Fab' and F(ab')2 fragments can also be employed using methods known in the art such as those disclosed in PCT publication WO 92/22324; Mullinax et al., *BioTechniques* 12(6):864-869 (1992); and Sawai et al., *AJRI* 34:26-34 (1995); and Better et al., *Science* 240:1041-1043 (1988) (said references incorporated by reference in their entireties).

Examples of techniques which can be used to produce single-chain Fvs and antibodies include those described in U.S. Pat. Nos. 4,946,778 and 5,258,498; Huston et al., *Methods in Enzymology* 203:46-88 (1991); Shu et al., *Proc. Natl. Acad. Sci. USA* 90:7995-7999 (1993); and Skerra et al., *Science* 240:1038-1040 (1988). For some uses, including in vivo use of antibodies in humans and in vitro detection assays, it may be preferable to use chimeric, humanized, or human antibodies. A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. See, e.g., Morrison, *Science* 229:1202 (1985); Oi et al., *BioTechniques* 4:214 (1986); Gillies et al., *J. Immunol. Methods* 125:191-202 (1989); U.S. Pat. Nos. 5,807,715; 4,816,567; and 4,816397, which are incorporated herein by reference in their entireties. Humanized antibodies are antibody molecules from non-human species antibody that binds the desired antigen having one or more complementarity determining regions (CDRs) from the non-human species and framework regions from a human immunoglobulin molecule. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., *Nature* 332:323 (1988), which are incorporated herein by reference in their entireties.) Antibodies can be humanized using a variety of techniques known in the art including, for example, CDR-grafting (EP 239,400; PCT publication WO 91/09967; U.S. Pat. Nos. 5,225,539; 5,530,101; and 5,585,089), veneering or resurfacing (EP 592,106; EP 519,596; Padlan, *Molecular Immunology* 28(4/5):489-498 (1991); Studnicka et al., *Protein Engineering* 7(6):805-814 (1994); Roguska. et al., *Proc. Natl. Acad. Sci. USA* 91:969-973 (1994)), and chain shuffling (U.S. Pat. No. 5,565,332).

Completely human antibodies are particularly desirable for therapeutic treatment of human patients. Human antibodies can be made by a variety of methods known in the art including phage display methods described above using antibody libraries derived from human immunoglobulin sequences. See also, U.S. Pat. Nos. 4,444,887 and 4,716,111; and PCT publications WO 98/46645, WO 98/50433, WO 98/24893, WO 98/16654, WO 96/34096, WO 96/33735, and WO 91/10741; each of which is incorporated herein by reference in its entirety.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring that express human antibodies. The transgenic mice are immunized in the normal fashion with a selected antigen, e.g., all or a portion of a desired target polypeptide. Monoclonal antibodies directed against the antigen can be obtained from the immunized, transgenic mice using conventional hybridoma technology. The human immunoglobulin transgenes harbored by the transgenic mice rearrange during B-cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar *Int. Rev. Immunol.* 13:65-93 (1995). For a detailed discussion of this technology for producing human antibodies and human monoclonal antibodies and protocols for producing such antibodies, see, e.g., PCT publications WO 98/24893; WO 96/34096; WO 96/33735; U.S. Pat. Nos. 5,413,923; 5,625,126; 5,633,425; 5,569,825; 5,661,016; 5,545,806; 5,814,318; and 5,939,598, which are incorporated by reference herein in their entirety. In addition, companies such as Abgenix, Inc. (Freemont, Calif.) and GenPharm (San Jose, Calif.) can be engaged to provide human antibodies directed against a selected antigen using technology similar to that described above.

Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al., *Bio/Technology* 12:899-903 (1988)). See also, U.S. Pat. No. 5,565,332.

In another embodiment, DNA encoding desired monoclonal antibodies may be readily isolated and sequenced using conventional procedures (e.g., by using oligonucleotide probes that are capable of binding specifically to genes encoding the heavy and light chains of murine antibodies). The isolated and subcloned hybridoma cells serve as a preferred source of such DNA. Once isolated, the DNA may be placed into expression vectors, which are then transfected into prokaryotic or eukaryotic host cells such as *E. coli* cells, simian COS cells, Chinese Hamster Ovary (CHO) cells or myeloma cells that do not otherwise produce immunoglobulins. More particularly, the isolated DNA (which may be synthetic as described herein) may be used to clone constant and variable region sequences for the manufacture antibodies as described in Newman et al., U.S. Pat. No. 5,658,570, filed Jan. 25, 1995, which is incorporated by reference herein. Essentially, this entails extraction of RNA from the selected cells, conversion to cDNA, and amplification by PCR using Ig specific primers. Suitable primers for this purpose are also described in U.S. Pat. No. 5,658,570. As will be discussed in more detail below, transformed cells expressing the desired antibody may be grown up in relatively large quantities to provide clinical and commercial supplies of the immunoglobulin.

In a specific embodiment, the amino acid sequence of the heavy and/or light chain variable domains may be inspected to identify the sequences of the complementarity determining regions (CDRs) by methods that are well know in the art, e.g., by comparison to known amino acid sequences of other heavy and light chain variable regions to determine the regions of sequence hypervariability. Using routine recombinant DNA techniques, one or more of the CDRs may be inserted within framework regions, e.g., into human framework regions to humanize a non-human antibody. The framework regions may be naturally occurring or consensus framework regions, and preferably human framework regions (see, e.g., Chothia et al., *J. Mol. Biol.* 278:457-479 (1998) for a listing of human framework regions). Preferably, the polynucleotide generated by the combination of the framework regions and CDRs encodes an antibody that specifically binds to at least one epitope of a desired polypeptide, e.g., a $PrP^c$ antagonist. Preferably, one or more amino acid substitutions may be made within the framework regions, and, preferably, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present invention and within the skill of the art.

In addition, techniques developed for the production of "chimeric antibodies" (Morrison et al., *Proc. Natl. Acad. Sci. USA* 81:851-855 (1984); Neuberger et al., *Nature* 312:604-608 (1984); Takeda et al., *Nature* 314:452-454 (1985)) by splicing genes from a mouse antibody molecule of appropriate antigen specificity together with genes from a human antibody molecule of appropriate biological activity can be used. As used herein, a chimeric antibody is a molecule in which different portions are derived from different animal species, such as those having a variable region derived from a murine monoclonal antibody and a human immunoglobulin constant region, e.g., humanized antibodies.

Alternatively, techniques described for the production of single chain antibodies (U.S. Pat. No. 4,694,778; Bird, *Science* 242:423-442 (1988); Huston et al., *Proc. Natl. Acad. Sci. USA* 85:5879-5883 (1988); and Ward et al., *Nature* 334:544-554 (1989)) can be adapted to produce single chain antibodies. Single chain antibodies are formed by linking the heavy and light chain fragments of the Fv region via an amino acid bridge, resulting in a single chain antibody. Techniques for the assembly of functional Fv fragments in *E coli* may also be used (Skerra et al., *Science* 242:1038-1041 (1988)).

$PrP^c$ antagonist antibodies may also be human or substantially human antibodies generated in transgenic animals (e.g., mice) that are incapable of endogenous immunoglobulin production (see e.g., U.S. Pat. Nos. 6,075,181, 5,939,598, 5,591,669 and 5,589,369 each of which is incorporated herein by reference). For example, it has been described that the homozygous deletion of the antibody heavy-chain joining region in chimeric and germ-line mutant mice results in complete inhibition of endogenous antibody production. Transfer of a human immunoglobulin gene array to such germ line mutant mice will result in the production of human antibodies upon antigen challenge. Another preferred means of generating human antibodies using SCID mice is disclosed in U.S. Pat. No. 5,811,524 which is incorporated herein by reference. It will be appreciated that the genetic material associated with these human antibodies may also be isolated and manipulated as described herein.

Yet another highly efficient means for generating recombinant antibodies is disclosed by Newman, *Biotechnology* 10:1455-1460 (1992). Specifically, this technique results in the generation of primatized antibodies that contain monkey variable domains and human constant sequences. This reference is incorporated by reference in its entirety herein. Moreover, this technique is also described in commonly assigned U.S. Pat. Nos. 5,658,570, 5,693,780 and 5,756,096 each of which is incorporated herein by reference.

In another embodiment, lymphocytes can be selected by micromanipulation and the variable genes isolated. For example, peripheral blood mononuclear cells can be isolated from an immunized mammal and cultured for about 7 days in vitro. The cultures can be screened for specific IgGs that meet the screening criteria. Cells from positive wells can be isolated. Individual Ig-producing B cells can be isolated by FACS or by identifying them in a complement-mediated hemolytic plaque assay. Ig-producing B cells can be micromanipulated into a tube and the $V_H$ and $V_L$ genes can be amplified using, e.g., RT-PCR. The $V_H$ and $V_L$ genes can be cloned into an antibody expression vector and transfected into cells (e.g., eukaryotic or prokaryotic cells) for expression.

Alternatively, antibody-producing cell lines may be selected and cultured using techniques well known to the skilled artisan. Such techniques are described in a variety of laboratory manuals and primary publications. In this respect, techniques suitable for use in the invention as described below are described in *Current Protocols in Immunology*, Coligan et al., Eds., Green Publishing Associates and Wiley-Interscience, John Wiley and Sons, New York (1991) which is herein incorporated by reference in its entirety, including supplements.

Antibodies for use in the therapeutic methods disclosed herein can be produced by any method known in the art for the synthesis of antibodies, in particular, by chemical synthesis or preferably, by recombinant expression techniques as described herein.

It will further be appreciated that the scope of this invention further encompasses all alleles, variants and mutations of antigen binding DNA sequences.

As is well known, RNA may be isolated from the original hybridoma cells or from other transformed cells by standard techniques, such as guanidinium isothiocyanate extraction and precipitation followed by centrifugation or chromatography. Where desirable, mRNA may be isolated from total RNA by standard techniques such as chromatography on oligo dT cellulose. Suitable techniques are familiar in the art.

In one embodiment, cDNAs that encode the light and the heavy chains of the antibody may be made, either simultaneously or separately, using reverse transcriptase and DNA polymerase in accordance with well known methods. PCR may be initiated by consensus constant region primers or by more specific primers based on the published heavy and light chain DNA and amino acid sequences. As discussed above, PCR also may be used to isolate DNA clones encoding the antibody light and heavy chains. In this case the libraries may be screened by consensus primers or larger homologous probes, such as mouse constant region probes.

DNA, typically plasmid DNA, may be isolated from the cells using techniques known in the art, restriction mapped and sequenced in accordance with standard, well known techniques set forth in detail, e.g., in the foregoing references relating to recombinant DNA techniques. Of course, the DNA may be synthetic according to the present invention at any point during the isolation process or subsequent analysis.

Recombinant expression of an antibody, or fragment, derivative or analog thereof, e.g., a heavy or light chain of an antibody which is $PrP^c$ antagonist, requires construction of an expression vector containing a polynucleotide that encodes the antibody. Once a polynucleotide encoding an antibody molecule or a heavy or light chain of an antibody, or portion thereof (preferably containing the heavy or light chain variable domain), of the invention has been obtained, the vector for the production of the antibody molecule may be produced by recombinant DNA technology using techniques well known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention, or a heavy or light chain thereof, or a heavy or light chain variable domain, operably linked to a promoter. Such vectors may include the nucleotide sequence encoding the constant region of the antibody molecule (see, e.g., PCT Publication WO 86/05807; PCT Publication WO 89/01036; and U.S. Pat. No. 5,122,464) and the variable domain of the antibody may be cloned into such a vector for expression of the entire heavy or light chain.

The expression vector is transferred to a host cell by conventional techniques and the transfected cells are then cultured by conventional techniques to produce an antibody for use in the methods described herein. Thus, the invention includes host cells containing a polynucleotide encoding an antibody of the invention, or a heavy or light chain thereof, operably linked to a heterologous promoter. In preferred embodiments for the expression of double-chained antibodies, vectors encoding both the heavy and light chains may be co-expressed in the host cell for expression of the entire immunoglobulin molecule, as detailed below.

A variety of host-expression vector systems may be utilized to express antibody molecules for use in the methods described herein. Such host-expression systems represent vehicles by which the coding sequences of interest may be produced and subsequently purified, but also represent cells which may, when transformed or transfected with the appropriate nucleotide coding sequences, express an antibody molecule of the invention in situ. These include but are not limited to microorganisms such as bacteria (e.g., *E. coli, B. subtilis*) transformed with recombinant bacteriophage DNA, plasmid DNA or cosmid DNA expression vectors containing antibody coding sequences; yeast (e.g., *Saccharomyces, Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BLK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *Escherichia coli*, and more preferably, eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., *Gene* 45:101 (1986); Cockett et al., *Bio/Technology* 8:2 (1990)).

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited, to the *E. coli* expression vector pUR278 (Ruther et al., *EMBO J*. 2:1791 (1983)), in which the antibody coding sequence may be ligated individually into the vector in frame with the lacZ coding region so that a fusion protein is produced; pIN vectors (Inouye & Inouye, *Nucleic Acids Res.* 13:3101-3109 (1985); Van Heeke & Schuster, *J. Biol. Chem.* 24:5503-5509 (1989)); and the like. pGEX vectors may also be used to express foreign polypeptides as fusion proteins with glutathione S-transferase (GST). In general, such fusion proteins are soluble and can easily be purified from lysed cells by adsorption and binding to a matrix glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is typically used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter).

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts. (e.g., see Logan & Shenk, *Proc. Natl. Acad. Sci. USA* 81:355-359 (1984)). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., *Methods in Enzymol.* 153:51-544 (1987)).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, HeLa, COS, MDCK, 293, 3T3, WI38, and in particular, breast cancer cell lines such as, for example, BT483, Hs578T, HTB2, BT20 and T47D, and normal mammary gland cell line such as, for example, CRL7030 and Hs578Bst.

For long-term, high-yield production of recombinant proteins, stable expression is preferred. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which stably express the antibody molecule.

A number of selection systems may be used, including but not limited to the herpes simplex virus thymidine kinase (Wigler et al., *Cell* 11:223 (1977)), hypoxanthine-guanine phosphoribosyltransferase (Szybalska & Szybalski, *Proc. Natl. Acad. Sci. USA* 48:202 (1992)), and adenine phosphoribosyltransferase (Lowy et al., *Cell* 22:817 1980) genes can be employed in tk-, hgprt- or aprt-cells, respectively. Also, antimetabolite resistance can be used as the basis of selection for the following genes: dhfr, which confers resistance to methotrexate (Wigler et al., *Natl. Acad. Sci. USA* 77:357 (1980); O'Hare et al., *Proc. Natl. Acad. Sci. USA* 78:1527 (1981)); gpt, which confers resistance to mycophenolic acid (Mulligan & Berg, *Proc. Natl. Acad. Sci. USA* 78:2072 (1981)); neo, which confers resistance to the aminoglycoside G-418 *Clinical Pharmacy* 12:488-505; Wu and Wu, *Biotherapy* 3:87-95 (1991); Tolstoshev, *Ann. Rev. Pharmacol. Toxicol.* 32:573-596 (1993); Mulligan, *Science* 260:926-932 (1993); and Morgan and Anderson, *Ann. Rev. Biochem.* 62:191-217 (1993); *TIB TECH* 11(5):155-215 (May, 1993); and hygro, which confers resistance to hygromycin (Santerre et al., *Gene* 30:147 (1984). Methods commonly known in the art of recombinant DNA technology which can be used are described in Ausubel et al. (eds.), *Current Protocols in Molecular Biology*, John Wiley & Sons, NY (1993); Kriegler, *Gene Transfer and Expression*, A Laboratory Manual, Stockton Press, NY (1990); and in Chapters 12 and 13, Dracopoli et al. (eds), *Current Prolocols in Human Genetics*, John Wiley & Sons, NY (1994); Colberre-Garapin et al., *J. Mol. Biol.* 150:1 (1981), which are incorporated by reference herein in their entireties.

The expression levels of an antibody molecule can be increased by vector amplification (for a review, see Bebbington and Hentschel, *The use of vectors based on gene amplification for the expression of cloned genes in mammalian cells in DNA cloning*, Academic Press, New York, Vol. 3. (1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., *Mol. Cell. Biol.* 3:257 (1983)).

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes both heavy and light chain polypeptides. In such situations, the light chain is advantageously placed before the heavy chain to avoid an excess of toxic free heavy chain (Proudfoot, *Nature* 322:52 (1986); Kohler, *Proc. Natl. Acad. Sci. USA* 77:2197 (1980)). The coding sequences for the heavy and light chains may comprise cDNA or genomic DNA.

Once an antibody molecule of the invention has been recombinantly expressed, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. Alternatively, a preferred method for increasing the affinity of antibodies of the invention is disclosed in US 2002 0123057 A1.

In one embodiment, a binding molecule or antigen binding molecule for use in the methods of the invention comprises a synthetic constant region wherein one or more domains are partially or entirely deleted ("domain-deleted antibodies"). In certain embodiments compatible modified antibodies will comprise domain deleted constructs or variants wherein the entire $C_H2$ domain has been removed ($\Delta C_H2$ constructs). For other embodiments a short connecting peptide may be substituted for the deleted domain to provide flexibility and freedom of movement for the variable region. Those skilled in the art will appreciate that such constructs are particularly preferred due to the regulatory properties of the $C_H2$ domain on the catabolic rate of the antibody.

In certain embodiments, modified antibodies for use in the methods disclosed herein are minibodies. Minibodies can be made using methods described in the art (see, e.g., see e.g., U.S. Pat. No. 5,837,821 or WO 94/09817A1).

In another embodiment, modified antibodies for use in the methods disclosed herein are $C_H2$ domain deleted antibodies which are known in the art. Domain deleted constructs can be derived using a vector encoding an IgG1 human constant domain (see, e.g., WO 02/060955A2 and WO02/096948A2). This exemplary vector was engineered to delete the $C_H2$ domain and provide a synthetic vector expressing a domain deleted IgG1 constant region.

In one embodiment, the $PrP^c$ antagonist antibody or fragment thereof for use in the treatment methods disclosed herein comprises an immunoglobulin heavy chain having deletion or substitution of a few or even a single amino acid as long as it permits association between the monomeric subunits. For example, the mutation of a single amino acid in selected areas of the $C_H2$ domain may be enough to substantially reduce Fc binding and thereby increase tumor localization. Similarly, it may be desirable to simply delete that part of one or more constant region domains that control the effector function (e.g. complement binding) to be modulated. Such partial deletions of the constant regions may improve selected characteristics of the antibody (serum half-life) while leaving other desirable functions associated with the subject constant region domain intact. Moreover, as alluded to above, the constant regions of the disclosed antibodies may be synthetic through the mutation or substitution of one or more amino acids that enhances the profile of the resulting construct. In this respect it may be possible to disrupt the activity provided by a conserved binding site (e.g. Fc binding) while substantially maintaining the configuration and immunogenic profile of the modified antibody. Yet other embodiments comprise the addition of one or more amino acids to the constant region to enhance desirable characteristics such as effector function or provide for more cytotoxin or carbohydrate attachment. In such embodiments it may be desirable to insert or replicate specific sequences derived from selected constant region domains.

The present invention also provides the use of antibodies that comprise, consist essentially of, or consist of, variants (including derivatives) of antibody molecules (e.g., the $V_H$ regions and/or $V_L$ regions) described herein, which antibodies or fragments thereof immunospecifically bind to a $PrP^c$ polypeptide. Standard techniques known to those of skill in the art can be used to introduce mutations in the nucleotide sequence encoding a binding molecule, including, but not limited to, site-directed mutagenesis and PCR-mediated mutagenesis which result in amino acid substitutions. Preferably, the variants (including derivatives) encode less than 50 amino acid substitutions, less than 40 amino acid substitutions, less than 30 amino acid substitutions, less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the reference $V_H$ region, $V_H$CDR1, $V_H$CDR2, $V_H$CDR3, $V_L$ region, $V_L$CDR1, $V_L$CDR2, or $V_L$CDR3. A "conservative amino acid substitution" is one in which the amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity.

For example, it is possible to introduce mutations only in framework regions or only in CDR regions of an antibody molecule. Introduced mutations may be silent or neutral missense mutations, i.e., have no, or little, effect on an antibody's ability to bind antigen. These types of mutations may be useful to optimize codon usage, or improve a hybridoma's antibody production. Alternatively, non-neutral missense mutations may alter an antibody's ability to bind antigen. The location of most silent and neutral missense mutations is likely to be in the framework regions, while the location of most non-neutral missense mutations is likely to be in CDR, though this is not an absolute requirement. One of skill in the art would be able to design and test mutant molecules with desired properties such as no alteration in antigen binding activity or alteration in binding activity (e.g., improvements in antigen binding activity or change in antibody specificity). Following mutagenesis, the encoded protein may routinely be expressed and the functional and/or biological activity of the encoded protein can be determined using techniques described herein or by routinely modifying techniques known in the art.

Antibodies used in the methods described herein include polyclonal as well as monoclonal antibodies, including full length antibodies, and antibody homologues, such as multispecific antibodies (e.g., bispecific antibodies), chimeric, humanized and fully human antibodies, and fragments of any of the foregoing, including Fab, Fab', F(ab')2, and Fv fragments, diabodies, linear antibodies, single-chain antibody molecules, and multispecific antibodies formed from antibody fragments, so long as they exhibit the desired biological activity. A monoclonal antibody indicates the character of the antibody as being a substantially homogeneous population of antibodies, and is not to be construed as requiring production of the antibody by any particular method.

For example, monoclonal antibodies include those antibodies made by the hybridoma method first described by Kohler et al., Nature 256:495 (1975), or may be made by recombinant DNA methods (see, e.g., U.S. Pat. No. 4,816, 567). Monoclonal antibodies may also be isolated from phage antibody libraries using, e.g., the techniques described in Clackson et al., *Nature* 352:624-628 (1991) and Marks et al., *J. Mol. Biol.* 222:581-597 (1991). Monoclonal antibodies also include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., *Proc. Natl. Acad. Sci. USA* 81:6851-6855 (1984)).

Also included are humanized monoclonal antibodies. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies may include residues which are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will include at least a portion of an immunoglobulin constant region (Fc), typically that of a human immunoglobulin. For further details, see Jones et al., *Nature* 321:522-525 (1986); Riechmann et al., *Nature* 332: 323-329 (1988); and Presta, *Curr. Op. Struct. Biol.* 2:593-596 (1992).

"Single-chain Fv" or "sFv" antibody fragments comprise the $V_H$ and $V_L$ domains of antibody, wherein these domains are present in a single polypeptide chain. Generally, the Fv polypeptide further comprises a polypeptide linker between the $V_H$ and $V_L$ domains which enables the sFv to form the desired structure for antigen binding. For a review of sFv see Pluckthun in The Pharmacology of Monoclonal Antibodies, vol. 113, Rosenburg and Moore eds. Springer-Verlag, New York, pp. 269-315 (1994).

The term "diabodies" refers to small antibody fragments with two antigen-binding sites, which fragments comprise a heavy chain variable domain ($V_H$) connected to a light chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA* 90:6444-6448 (1993).

The expression "linear antibodies" when used throughout this application refers to the antibodies described in Zapata et al. *Protein Eng.* 8(10):1057-1062 (1995). Briefly, these antibodies comprise a pair of tandem Fd segments ($V_H$-$C_{H1}$-$V_H$-$C_{H1}$) which form a pair of antigen binding regions. Linear antibodies can be bispecific or monospecific.

To express the antibodies or antibody fragments, DNAs encoding partial or full-length light and heavy chains are inserted into expression vectors such as plasmids, retroviruses, cosmids, YACs, EBV-derived episomes, and the like. The expression vector and expression control sequences are chosen to be compatible with the expression host cell used. The antibody light chain gene and the antibody heavy chain gene can be inserted into separate vector. In some embodiments, both genes are inserted into the same expression vector.

A convenient vector is one that encodes a functionally complete human $C_H$ or $C_L$ immunoglobulin sequence. Preferably, restriction sites engineered so that any $V_H$ or $V_L$ sequence can be easily inserted and expressed. In such vectors, splicing usually occurs between the splice donor site in the inserted J region and the splice acceptor site preceding the human C region, and also at the splice regions that occur within the human $C_H$ exons. Polyadenylation and transcription termination occur at native chromosomal sites downstream of the coding regions. The recombinant expression vector can also encode a signal peptide that facilitates secretion of the antibody chain from a host cell.

Techniques for making and using antibodies and antibody fragments and homologues can be found, e.g., in Zola, *Monoclonal Antibodies: Preparation and Use of Monoclonal Antibodies and Engineered Antibody Derivatives* (Basics: From Background to Bench), 1st edition, 2000, BIOS Scientific Publishers; and Osbourn (2003) *Drug Discov Today* 8(18): 845-51.

$PrP^c$ Antagonist Polynucleotides

Specific embodiments comprise a method of inhibiting suppression of long term potentiation, a method of improving/increasing acute memory retention, a method of improving/increasing spatial memory performance, and a method of treating Alzheimer's disease comprising administering an effective amount of a $PrP^c$ antagonist polynucleotide which comprises a nucleic acid molecule which specifically binds to a polynucleotide which encodes $PrP^c$. The $PrP^c$ polynucleotide antagonist acts, e.g., by preventing expression of $PrP^c$ (knockdown). $PrP^c$ polynucleotide antagonists include, but are not limied to, antisense molecules, ribozymes, siRNA, shRNA and RNAi. Typically, such binding molecules are separately administered to the animal (see, for example, O'Connor, *J. Neurochem.* 56:560 (1991)), but such binding molecules may also be expressed in vivo from polynucleotides taken up by a host cell and expressed in vivo. See also *Oligodeoxynucleotides as Antisense Inhibitors of Gene Expression*, CRC Press, Boca Raton, Fla. (1988).

RNAi refers to the expression of an RNA which interferes with the expression of the targeted mRNA. Specifically, the RNAi silences a targeted gene via interacting with the specific mRNA through a siRNA (short interfering RNA). The ds RNA complex is then targeted for degradation by the cell. Additional RNAi molecules include Short hairpin RNA (shRNA); also short interfering hairpin. The shRNA molecule contains sense and antisense sequences from a target gene connected by a loop. The shRNA is transported from the nucleus into the cytoplasm, it is degraded along with the mRNA. Pol III or U6 promoters can be used to express RNAs for RNAi.

RNAi is mediated by double stranded RNA (dsRNA) molecules that have sequence-specific homology to their "target" mRNAs (Caplen et al., *Proc Natl Acad Sci USA* 98:9742-9747, 2001). Biochemical studies in *Drosophila* cell-free lysates indicates that the mediators of RNA-dependent gene silencing are 21-25 nucleotide "small interfering" RNA duplexes (siRNAs). Accordingly, siRNA molecules are advantageously used in the methods of the present invention. The siRNAs are derived from the processing of dsRNA by an RNase known as DICER (Bernstein et al., *Nature* 409:363-366, 2001). It appears that siRNA duplex products are recruited into a multi-protein siRNA complex termed RISC (RNA Induced Silencing Complex). Without wishing to be bound by any particular theory, it is believed that a RISC is guided to a target mRNA, where the siRNA duplex interacts sequence-specifically to mediate cleavage in a catalytic fashion (Bernstein et al., *Nature* 409:363-366, 2001; Boutla et al., *Curr Biol* 11:1776-1780, 2001).

RNAi has been used to analyze gene function and to identify essential genes in mammalian cells (Elbashir et al., *Methods* 26:199-213, 2002; Harborth et al., *J Cell Sci* 114:4557-4565, 2001), including by way of non-limiting example neurons (Krichevsky et al., *Proc Natl Acad Sci USA* 99:11926-11929, 2002). RNAi is also being evaluated for therapeutic modalities, such as inhibiting or blocking the infection, replication and/or growth of viruses, including without limitation poliovirus (Gitlin et al., *Nature* 418:379-380, 2002) and HIV (Capodici et al., *J Immunol* 169:5196-5201, 2002), and reducing expression of oncogenes (e.g., the bcr-abl gene; Scherr et al., *Blood September* 26 epub ahead of print, 2002). RNAi has been used to modulate gene expression in mammalian (mouse) and amphibian (*Xenopus*) embryos (respectively, Calegari et al., *Proc Natl Acad Sci USA* 99:14236-14240, 2002; and Zhou, et al., *Nucleic Acids Res* 30:1664-1669, 2002), and in postnatal mice (Lewis et al., *Nat Genet* 32:107-108, 2002), and to reduce trangsene expression in adult transgenic mice (McCaffrey et al., *Nature* 418:38-39, 2002). Methods have been described for determining the efficacy and specificity of siRNAs in cell culture and in vivo (see, e.g., Bertrand et al., *Biochem Biophys Res Commun* 296:1000-1004, 2002; Lassus et al., *Sci STKE* 2002 (147):PL13, 2002; and Leirdal et al., *Biochem Biophys Res Commun* 295:744-748, 2002).

Molecules that mediate RNAi, including without limitation siRNA, can be produced in vitro by chemical synthesis (Hohjoh, *FEBS Lett* 521:195-199, 2002), hydrolysis of dsRNA (Yang et al., *Proc Natl Acad Sci USA* 99:9942-9947, 2002), by in vitro transcription with T7 RNA polymerase (Donzeet et al., *Nucleic Acids Res* 30:e46, 2002; Yu et al., *Proc Natl Acad Sci USA* 99:6047-6052, 2002), and by hydrolysis of double-stranded RNA using a nuclease such as *E. coli* RNase III (Yang et al., *Proc Natl Acad Sci USA* 99:9942-9947, 2002).

siRNA molecules may also be formed by annealing two oligonucleotides to each other, typically have the following general structure, which includes both double-stranded and single-stranded portions:

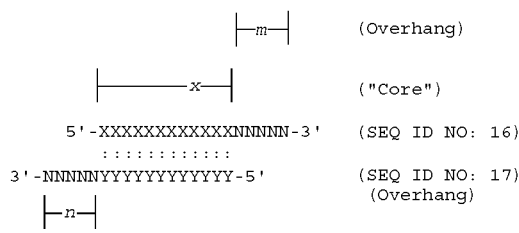

Wherein N, X and Y are nucleotides; X hydrogen bonds to Y; ":" signifies a hydrogen bond between two bases; x is a natural integer having a value between 1 and about 100; and m and n are whole integers having, independently, values between 0 and about 100. In some embodiments, N, X and Y are independently A, G, C and T or U. Non-naturally occurring bases and nucleotides can be present, particularly in the case of synthetic siRNA (i.e., the product of annealing two oligonucleotides). The double-stranded central section is called the "core" and has base pairs (bp) as units of measurement; the single-stranded portions are overhangs, having nucleotides (nt) as units of measurement. The overhangs shown are 3' overhangs, but molecules with 5' overhangs are also within the scope of the invention. Also within the scope of the invention are siRNA molecules with no overhangs (i.e., m=0 and n=0), and those having an overhang on one side of the core but not the other (e.g., m=0 and n>1, or vice-versa).

Initially, RNAi technology did not appear to be readily applicable to mammalian systems. This is because, in mammals, dsRNA activates dsRNA-activated protein kinase (PKR) resulting in an apoptotic cascade and cell death (Der et al, *Proc. Natl. Acad. Sci. USA* 94:3279-3283, 1997). In addition, it has long been known that dsRNA activates the interferon cascade in mammalian cells, which can also lead to altered cell physiology (Colby et al., *Annu. Rev. Microbiol.* 25:333, 1971; Kleinschmidt et al., *Annu. Rev. Biochem.* 41:517, 1972; Lampson et al., *Proc. Natl. Acad. Sci. USA* 58L782, 1967; Lomniczi et al., *J. Gen. Virol.* 8:55, 1970; and Younger et al., *J. Bacteriol.* 92:862, 1966). However, dsRNA-mediated activation of the PKR and interferon cascades requires dsRNA longer than about 30 base pairs. In contrast, dsRNA less than 30 base pairs in length has been demonstrated to cause RNAi in mammalian cells (Caplen et al., *Proc. Natl. Acad. Sci. USA* 98:9742-9747, 2001). Thus, it is expected that undesirable, non-specific effects associated with longer dsRNA molecules can be avoided by preparing short RNA that is substantially free from longer dsRNAs.

References regarding siRNA: Bernstein et al., *Nature* 409: 363-366, 2001; Boutla et al., *Curr Biol* 11:1776-1780, 2001; Cullen, *Nat Immunol.* 3:597-599, 2002; Caplen et al., *Proc Natl Acad Sci USA* 98:9742-9747, 2001; Hamilton et al., *Science* 286:950-952, 1999; Nagase et al., *DNA Res.* 6:63-70, 1999; Napoli et al., *Plant Cell* 2:279-289, 1990; Nicholson et al., *Mamm. Genome* 13:67-73, 2002; Parrish et al., *Mol Cell* 6:1077-1087, 2000; Romano et al., *Mol Microbiol* 6:3343-3353, 1992; Tabara et al., *Cell* 99:123-132, 1999; and Tuschl, *Chembiochem.* 2:239-245, 2001.

Paddison et al. (*Genes & Dev.* 16:948-958, 2002) have used small RNA molecules folded into hairpins as a means to effect RNAi. Accordingly, such short hairpin RNA (shRNA) molecules are also advantageously used in the methods of the invention. The length of the stem and loop of functional shRNAs varies; stem lengths can range anywhere from about 25 to about 30 nt, and loop size can range between 4 to about 25 nt without affecting silencing activity. While not wishing to be bound by any particular theory, it is believed that these shRNAs resemble the dsRNA products of the DICER RNase and, in any event, have the same capacity for inhibiting expression of a specific gene.

Expression of PrP$^c$ gene can, in some embodiments, also be inhibited using RNA interference ("RNAi"). RNAi is a phenomenon in which the introduction of double-stranded RNA (dsRNA) into a cell causes degradation of the homologous mRNA. First discovered in the nematode *Caenorhabditis elegans*, RNAi has since been found to operate in a wide range of organisms. An "RNAi nucleic acid" as used herein is a nucleic acid sequence generally shorter than 50 nucleotides in length, that causes gene silencing at the mRNA level. RNAi nucleic acids include gene-specific short interfering RNAs (siRNA), and double-stranded RNAs (dsRNA).

For example, in mammalian cells, introduction of long dsRNA (>30 nucleotides) can initiate a potent antiviral response, exemplified by nonspecific inhibition of protein synthesis and RNA degradation. RNA interference provides a mechanism of gene silencing at the mRNA level. In recent years, RNAi has become an endogenous and potent gene-specific silencing technique that uses double-stranded RNAs (dsRNA) to mark a particular transcript for degradation in vivo. It also offers an efficient and broadly applicable approach for gene knock-out. In addition, RNAi technology can be used for therapeutic purposes. For example, RNAi targeting Fas-mediated apoptosis has been shown to protect mice from fulminant hepatitis. RNAi technology has been disclosed in numerous publications, such as U.S. Pat. Nos. 5,919,619, 6,506,559 and PCT Publication Nos. WO99/14346, WO01/70949, WO01/36646, WO00/63364, WO00/44895, WO01/75164, WO01/92513, WO01/68836 and WO01/29058.

A sequence capable of inhibiting gene expression by RNA interference can have any length. For instance, the sequence can have at least 10, 15, 20, 25, 30, 35, 40, 45, 50, 100 or more consecutive nucleotides. The sequence can be dsRNA or any other type of polynucleotide, provided that the sequence can form a functional silencing complex to degrade the target mRNA transcript.

In one embodiment, the sequence comprises or consists of a short interfering RNAs (siRNA). The siRNA can be dsRNA having 19-25 nucleotides. siRNAs can be produced endogenously by degradation of longer dsRNA molecules by an RNase III-related nuclease called Dicer. siRNAs can also be introduced into a cell exogenously, or by transcription of an expression construct. Once formed, the siRNAs assemble with protein components into endoribonuclease-containing complexes known as RNA-induced silencing complexes (RISCs). An ATP-generated unwinding of the siRNA activates the RISCs, which in turn target the complementary mRNA transcript by Watson-Crick base-pairing, thereby cleaving and destroying the mRNA. Cleavage of the mRNA takes place near the middle of the region bound by the siRNA strand. This sequence specific mRNA degradation results in gene silencing.

At least two ways can be employed to achieve siRNA-mediated gene silencing. First, siRNAs can be synthesized in vitro and introduced into cells to transiently suppress gene expression. Synthetic siRNA provides an easy and efficient way to achieve RNAi. siRNA are duplexes of short mixed oligonucleotides which can include, for example, 19 RNAs nucleotides with symmetric dinucleotide 3' overhangs. Using synthetic 21 by siRNA duplexes (e.g., 19 RNA bases followed by a UU or dTdT 3' overhang), sequence specific gene silencing can be achieved in mammalian cells. These siRNAs can specifically suppress targeted gene translation in mammalian cells without activation of DNA-dependent protein kinase (PKR) by longer dsRNA, which may result in non-specific repression of translation of many proteins. Second, siRNAs can be expressed in vivo from vectors.

In some embodiments of the invention, the shRNA is expressed from a lentiviral vector, e.g., pLL3.7.

Antisense technology can be used to control gene expression through antisense DNA or RNA, or through triple-helix formation. Antisense techniques are discussed for example, in Okano, *J. Neurochem.* 56:560 (1991); Oligodeoxynucleotides as Antisense Inhibitors of Gene Expression, CRC Press, Boca Raton, Fla. (1988). Triple helix formation is discussed in, for instance, Lee et al., *Nucleic Acids Research* 6:3073 (1979); Cooney et al., *Science* 241:456 (1988); and Dervan et al., *Science* 251:1300 (1991). The methods are based on binding of a polynucleotide to a complementary DNA or RNA.

For example, the 5' non-coding portion of a polynucleotide that encodes $PrP^c$ may be used to design an antisense RNA oligonucleotide of from about 10 to 40 base pairs in length. A DNA oligonucleotide is designed to be complementary to a region of the gene involved in transcription thereby preventing transcription and the production of the target protein. The antisense RNA oligonucleotide hybridizes to the mRNA in vivo and blocks translation of the mRNA molecule into the target polypeptide.

In one embodiment, antisense nucleic acids specific for a $PrP^c$ gene are produced intracellularly by transcription from an exogenous sequence. For example, a vector or a portion thereof, is transcribed, producing an antisense nucleic acid (RNA). Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in vertebrate cells. Expression of the antisense molecule, can be by any promoter known in the art to act in vertebrate, preferably human cells, such as those described elsewhere herein.

Absolute complementarity of an antisense molecule, although preferred, is not required. A sequence complementary to at least a portion of an RNA encoding $PrP^c$ means a sequence having sufficient complementarity to be able to hybridize with the RNA, forming a stable duplex; or triplex formation may be assayed. The ability to hybridize will depend on both the degree of complementarity and the length of the antisense nucleic acid. Generally, the larger the hybridizing nucleic acid, the more base mismatches it may contain and still form a stable duplex (or triplex as the case may be). One skilled in the art can ascertain a tolerable degree of mismatch by use of standard procedures to determine the melting point of the hybridized complex.

Oligonucleotides that are complementary to the 5' end of a messenger RNA, e.g., the 5' untranslated sequence up to and including the AUG initiation codon, should work most efficiently at inhibiting translation. However, sequences complementary to the 3' untranslated sequences of mRNAs have been shown to be effective at inhibiting translation of mRNAs as well. See generally, Wagner, R., *Nature* 372:333-335 (1994). Thus, oligonucleotides complementary to either the 5'- or 3'-non-translated, non-coding regions could be used in an antisense approach to inhibit translation of $PrP^c$. Oligonucleotides complementary to the 5' untranslated region of the mRNA should include the complement of the AUG start codon. Antisense oligonucleotides complementary to mRNA coding regions are less efficient inhibitors of translation but could be used in accordance with the invention. Antisense nucleic acids should be at least six nucleotides in length, and are preferably oligonucleotides ranging from 6 to about 50 nucleotides in length. In specific aspects the oligonucleotide is at least 10 nucleotides, at least 17 nucleotides, at least 25 nucleotides or at least 50 nucleotides.

Polynucleotides for use the therapeutic methods disclosed herein can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, e.g., Letsinger et al., *Proc. Natl. Acad. Sci. USA*. 86:6553-6556 (1989); Lemaitre et al., *Proc. Natl. Acad. Sci. USA* 84:648-652 (1987)); PCT Publication No. WO88/09810, published Dec. 15, 1988) or the blood-brain barrier (see, e.g., PCT Publication No. WO89/10134, published Apr. 25, 1988), hybridization-triggered cleavage agents. (See, e.g., Krol et al., *BioTechniques* 6:958-976 (1988)) or intercalating agents. (See, e.g., Zon, *Pharm. Res.* 5:539-549(1988)). To this end, the oligonucleotide may be conjugated to another molecule, e.g., a peptide, hybridization triggered cross-linking agent, transport agent, hybridization-triggered cleavage agent, etc.

An antisense oligonucleotide for use in the therapeutic methods disclosed herein may comprise at least one modified base moiety which is selected from the group including, but not limited to, 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N-6-isopentenyladenine, 1-methylguanine, 1-methylinosine, 2,2-dimethylguanine, 2-methyladenine, 2-methylguanine, 3-methylcytosine, 5-methylcytosine, N-6-adenine, 7-methylguanine, 5-methylaminomethyluracil, 5-methoxyaminomethyl-2-thiouracil, beta-D-mannosylqueosine, 5'methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3(3-amino-3-N2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest.

An antisense oligonucleotide for use in the therapeutic methods disclosed herein may also comprise at least one modified sugar moiety selected from the group including, but not limited to, arabinose, 2-fluoroarabinose, xylulose, and hexose.

In yet another embodiment, an antisense oligonucleotide for use in the therapeutic methods disclosed herein comprises at least one modified phosphate backbone selected from the group including, but not limited to, a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, an antisense oligonucleotide for use in the therapeutic methods disclosed herein is an α-anomeric oligonucleotide. An α-anomeric oligonucleotide forms specific double-stranded hybrids with complementary RNA in which, contrary to the usual situation, the strands run parallel to each other (Gautier et al., *Nucl. Acids Res.* 15:6625-6641(1987)). The oligonucleotide is a 2'-0-methylribonucleotide (Inoue et al., *Nucl. Acids Res.* 15:6131-6148 (1987)), or a chimeric RNA-DNA analogue (Inoue et al., *FEBS Lett.* 215:327-330(1987)).

Polynucleotides of the invention, including aptamers, may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al., *Nucl. Acids Res.* 16:3209 (1988), methylphosphonate oligonucleotides can be prepared by use of controlled pore glass polymer supports (Sarin et al., *Proc. Natl. Acad. Sci. USA.* 85:7448-7451 (1988)), etc.

Polynucleotide compositions for use in the therapeutic methods disclosed herein further include catalytic RNA, or a ribozyme (See, e.g., PCT International Publication WO 90/11364, published Oct. 4, 1990; Sarver et al., *Science* 247: 1222-1225 (1990). The use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, *Nature* 334:585-591 (1988). Preferably, the ribozyme is engineered so that the cleavage recognition site is located near the 5' end of the target mRNA; i.e., to increase efficiency and minimize the intracellular accumulation of non-functional mRNA transcripts.

As in the antisense approach, ribozymes for use in the diagnostic and therapeutic methods disclosed herein can be composed of modified oligonucleotides (e.g. for improved stability, targeting, etc.) and may be delivered to cells which express $PrP^c$ in vivo. DNA constructs encoding the ribozyme may be introduced into the cell in the same manner as described above for the introduction of antisense encoding DNA. A preferred method of delivery involves using a DNA construct "encoding" the ribozyme under the control of a strong constitutive promoter, such as, for example, pol III or pol II promoter, so that transfected cells will produce sufficient quantities of the ribozyme to destroy endogenous $PrP^c$ messages and inhibit translation. Since ribozymes unlike antisense molecules, are catalytic, a lower intracellular concentration is required for efficiency.

In some embodiments, $PrP^c$ expression can be inhibited by using antisense nucleic acids to directly block the translation of mRNA by hybridizing to targeted mRNA and preventing protein translation.

An "antisense" nucleic acid includes a nucleotide sequence which is complementary to a "sense" nucleic acid encoding the component, e.g., complementary to the coding strand of a double-stranded cDNA molecule or complementary to an mRNA sequence. Accordingly, an antisense nucleic acid can form hydrogen bonds with a sense nucleic acid. The antisense nucleic acid can be complementary to an entire coding strand, or to only a portion thereof. For example, an antisense nucleic acid molecule which antisense to the "coding region" of the coding strand of a nucleotide sequence encoding the component can be used.

The coding strand sequence encoding $PrP^c$s are known. Thus, a skilled person can design antisense nucleic acids according to the rules of Watson and Crick base pairing. The antisense nucleic acid molecule can be complementary to the entire coding region of mRNA, but more preferably is an oligonucleotide which is antisense to only a portion of the coding or noncoding region of mRNA. For example, the antisense oligonucleotide can be complementary to the region surrounding the translation start site of the mRNA. An antisense oligonucleotide can be, for example, about 5, 10, 15, 20, 25, 30, 35, 40, 45 or 50 nucleotides in length. An antisense nucleic acid can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used.

Ribozymes are enzymatic RNA molecules capable of catalyzing the specific cleavage of RNA. Ribozymes act by sequence-specific hybridization to the complementary target RNA, followed by endonucleolytic cleavage. Specific ribozyme cleavage sites within a potential RNA target can be identified by known techniques. For further details see, e.g., Rossi, Current Biology 4, 469-471 (1994), and PCT publication No. WO 97/3355.

A review of antisense therapeutics as it related to CNS disease is provided in Jaeger, 2004, *Front Biosci.* 9:1720-7.

Aptamers

In another embodiment, the $PrP^c$ antagonist for use in the methods of the present invention is an aptamer. An aptamer can be a nucleotide or a polypeptide which has a unique sequence, has the property of binding specifically to a desired target (e.g., a polypeptide), and is a specific ligand of a given target. Nucleotide aptamers of the invention include double stranded DNA and single stranded RNA molecules that bind to $PrP^c$.

Nucleic acid aptamers are selected using methods known in the art, for example via the Systematic Evolution of Ligands by Exponential Enrichment (SELEX) process. SELEX is a method for the in vitro evolution of nucleic acid molecules with highly specific binding to target molecules as described in e.g., U.S. Pat. Nos. 5,475,096, 5,580,737, 5,567,588, 5,707,796, 5,763,177, 6,011,577, and 6,699,843, incorporated herein by reference in their entirety. Another screening method to identify aptamers is described in U.S. Pat. No. 5,270,163 (also incorporated herein by reference). The SELEX process is based on the capacity of nucleic acids for forming a variety of two- and three-dimensional structures, as well as the chemical versatility available within the nucleotide monomers to act as ligands (form specific binding pairs) with virtually any chemical compound, whether monomeric or polymeric, including other nucleic acid molecules and polypeptides. Molecules of any size or composition can serve as targets.

The SELEX method involves selection from a mixture of candidate oligonucleotides and step-wise iterations of binding, partitioning and amplification, using the same general selection scheme, to achieve desired binding affinity and selectivity. Starting from a mixture of nucleic acids, preferably comprising a segment of randomized sequence, the SELEX method includes steps of contacting the mixture with the target under conditions favorable for binding; partitioning unbound nucleic acids from those nucleic acids which have bound specifically to target molecules; dissociating the nucleic acid-target complexes; amplifying the nucleic acids dissociated from the nucleic acid-target complexes to yield a ligand enriched mixture of nucleic acids. The steps of binding, partitioning, dissociating and amplifying are repeated through as many cycles as desired to yield highly specific high affinity nucleic acid ligands to the target molecule.

Nucleotide aptamers may be used, for example, as diagnostic tools or as specific inhibitors to dissect intracellular signaling and transport pathways (James, *Curr. Opin. Pharmacol.* 1:540-546 (2001)). The high affinity and specificity of nucleotide aptamers makes them good candidates for drug discovery. For example, aptamer antagonists to the toxin ricin have been isolated and have 1050 values in the nanomolar range (Hesselberth J R et al., *J Biol Chem* 275:4937-4942 (2000)). Nucleotide aptamers may also be used against infectious disease, malignancy and viral surface proteins to reduce cellular infectivity.

Nucleotide aptamers for use in the methods of the present invention may be modified (e.g., by modifying the backbone or bases or conjugated to peptides) as described herein for other polynucleotides.

Using the protein structure of $PrP^c$, screening for aptamers that act on $PrP^c$ using the SELEX process would allow for the identification of aptamers that inhibit $PrP^c$-mediated processes (e.g., $PrP^c$-mediated synaptic dysfunction).

Polypeptide aptamers for use in the methods of the present invention are random peptides selected for their ability to bind to and thereby block the action of $PrP^c$. Polypeptide aptamers may include a short variable peptide domain attached at both ends to a protein scaffold. This double structural constraint greatly increases the binding affinity of the peptide aptamer to levels comparable to an antibody's (nanomolar range). See, e.g., Hoppe-Seyler F et al., *J Mol Med* 78(8):426-430 (2000)). The length of the short variable peptide is typically about 10 to 20 amino acids, and the scaffold may be any protein which has good solubility and compacity properties. One non-limiting example of a scaffold protein is the bacterial protein Thioredoxin-A. See, e.g., Cohen B A et al., *PNAS* 95(24): 14272-14277 (1998)).

Polypeptide aptamers are peptides or small polypeptides that act as dominant inhibitors of protein function. Peptide aptamers specifically bind to target proteins, blocking their functional ability (Kolonin et al., *Proc. Natl. Acad. Sci.* 95: 14,266-14,271 (1998)). Peptide aptamers that bind with high affinity and specificity to a target protein can be isolated by a variety of techniques known in the art. Peptide aptamers can be isolated from random peptide libraries by yeast two-hybrid screens (Xu, C. W., et al. (1997) *Proc. Natl. Acad. Sci.* 94:12, 473-12,478) or by ribosome display (Hanes et al. (1997) *Proc. Natl. Acad. Sci.* 94:4937-4942). They can also be isolated from phage libraries (Hoogenboom, H. R., et al. (1998) *Immunotechnology* 4:1-20) or chemically generated peptide libraries. Additionally, polypeptide aptamers may be selected using the selection of Ligand Regulated Peptide Aptamers (LiRPAs). See, e.g., Binkowski B F et al., (2005) *Chem & Biol* 12(7): 847-855, incorporated herein by reference. Although the difficult means by which peptide aptamers are synthesized makes their use more complex than polynucleotide aptamers, they have unlimited chemical diversity. Polynucleotide aptamers are limited because they utilize only the four nucleotide bases, while peptide aptamers would have a much-expanded repertoire (i.e., 20 amino acids).

Peptide aptamers for use in the methods of the present invention may be modified (e.g., conjugated to polymers or fused to proteins) as described for other polypeptides elsewhere herein.

Vectors

Vectors comprising nucleic acids encoding $PrP^c$ antagonists may also be used to produce antagonists for use in the methods of the invention. The choice of vector and expression control sequences to which such nucleic acids are operably linked depends on the functional properties desired, e.g., protein expression, and the host cell to be transformed.

In a typical embodiment, a $PrP^c$ antagonist polypeptide useful in the methods described herein is a recombinant protein produced by a cell (e.g., a CHO cell) that carries an exogenous nucleic acid encoding the protein. In other embodiments, the recombinant polypeptide is produced by a process commonly known as gene activation, wherein a cell that carries an exogenous nucleic acid that includes a promoter or enhancer is operably linked to an endogenous nucleic acid that encodes the polypeptide.

Routine techniques for making recombinant polypeptides (e.g., a recombinant $PrP^c$ antagonist or fragments thereof) may be used to construct expression vectors encoding the polypeptides of interest using appropriate transcriptional/translational control signals and the protein coding sequences. (See, for example, Sambrook et al., Molecular Cloning: A Laboratory Manual, 3d Ed. (Cold Spring Harbor Laboratory 2001)). These methods may include in vitro recombinant DNA and synthetic techniques and in vivo recombination, e.g., in vivo homologous recombination.

Expression of a nucleic acid sequence encoding a polypeptide may be regulated by a second nucleic acid sequence that is operably linked to the polypeptide encoding sequence such that the polypeptide is expressed in a host transformed with the recombinant DNA molecule.

Expression control elements useful for regulating the expression of an operably linked coding sequence are known in the art. Examples include, but are not limited to, inducible promoters, constitutive promoters, secretion signals, and other regulatory elements. When an inducible promoter is used, it can be controlled, e.g., by a change in nutrient status, or a change in temperature, in the host cell medium.

Expression vectors capable of being replicated in a bacterial or eukaryotic host comprising a nucleic acid encoding a polypeptide are used to transfect a host and thereby direct expression of such nucleic acid to produce the polypeptide, which may then be isolated. The preferred mammalian expression vectors contain both prokaryotic sequences, to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Routine techniques for transfecting cells with exogenous DNA sequences may be used in the present invention. Transfection methods may include chemical means, e.g., calcium phosphate, DEAE-dextran, or liposome; or physical means, e.g., microinjection or electroporation. The transfected cells are grown up by routine techniques. For examples, see Kuchler et al. (1977) Biochemical Methods in Cell Culture and Virology. The expression products are isolated from the cell medium in those systems where the protein is secreted from the host cell, or from the cell suspension after disruption of the host cell system by, e.g., routine mechanical, chemical, or enzymatic means.

These methods may also be carried out using cells that have been genetically modified by other procedures, including gene targeting and gene activation (see Treco et al. WO 95/31560, herein incorporated by reference; see also Selden et al. WO 93/09222).

The vector can include a prokaryotic replicon, i.e., a DNA sequence having the ability to direct autonomous replication and maintenance of the recombinant DNA molecule extrachromosomally in a bacterial host cell. Such replicons are well known in the art. In addition, vectors that include a prokaryotic replicon may also include a gene whose expression confers a detectable marker such as a drug resistance. Examples of bacterial drug-resistance genes are those that confer resistance to ampicillin or tetracycline.

Vectors that include a prokaryotic replicon can also include a prokaryotic or bacteriophage promoter for directing expression of the coding gene sequences in a bacterial host cell. Promoter sequences compatible with bacterial hosts are typically provided in plasmid vectors containing convenient restriction sites for insertion of a DNA segment to be expressed. Examples of such plasmid vectors are pUC8, pUC9, pBR322 and pBR329 (BioRad), pPL and pKK223 (Pharmacia). Any suitable prokaryotic host can be used to express a recombinant DNA molecule encoding a protein used in the methods of the invention.

For the purposes of this invention, numerous expression vector systems may be employed. For example, one class of vector utilizes DNA elements which are derived from animal viruses such as bovine papilloma virus, polyoma virus, adenovirus, adeno-associated virus, herpes simplex virus-1, vaccinia virus, baculovirus, retroviruses (RSV, MMTV or MOMLV) or SV40 virus. Others involve the use of polycistronic systems with internal ribosome binding sites. Additionally, cells which have integrated the DNA into their chromosomes may be selected by introducing one or more markers which allow selection of transfected host cells. The marker may provide for prototrophy to an auxotrophic host, biocide resistance (e.g., antibiotics) or resistance to heavy metals such as copper. The selectable marker gene can either be directly linked to the DNA sequences to be expressed, or introduced into the same cell by cotransformation. The neomycin phosphotransferase (neo) gene is an example of a selectable marker gene (Southern et al., *J. Mol. Anal. Genet.* 1:327-341 (1982)). Additional elements may also be needed for optimal synthesis of mRNA. These elements may include signal sequences, splice signals, as well as transcriptional promoters, enhancers, and termination signals.

Of course, any expression vector which is capable of eliciting expression in eukaryotic cells may be used in the present invention. Examples of suitable vectors include, but are not limited to plasmids pcDNA3, pHCMV/Zeo, pCR3.1, pEF1/His, pIND/GS, pRc/HCMV2, pSV40/Zeo2, pTRACER-HCMV, pUB6/V5-His, pVAX1, and pZeoSV2 (available from Invitrogen, San Diego, Calif.), and plasmid pCI (available from Promega, Madison, Wis.). Additional eukaryotic cell expression vectors are known in the art and are commercially available. Typically, such vectors contain convenient restriction sites for insertion of the desired DNA segment. Exemplary vectors include pSVL and pKSV-10 (Pharmacia), pBPV-1, pml2d (International Biotechnologies), pTDT1 (ATCC 31255), retroviral expression vector pMIG and pLL3.7, adenovirus shuttle vector pDC315, and AAV vectors. Other exemplary vector systems are disclosed e.g., in U.S. Pat. No. 6,413,777.

In general, screening large numbers of transformed cells for those which express suitably high levels of the antagonist is routine experimentation which can be carried out, for example, by robotic systems.

Frequently used regulatory sequences for mammalian host cell expression include viral elements that direct high levels of protein expression in mammalian cells, such as promoters and enhancers derived from retroviral LTRs, cytomegalovirus (CMV) (such as the CMV promoter/enhancer), Simian Virus 40 (SV40) (such as the SV40 promoter/enhancer), adenovirus, (e.g., the adenovirus major late promoter (Adm1P)), polyoma and strong mammalian promoters such as native immunoglobulin and actin promoters. For further description of viral regulatory elements, and sequences thereof, see e.g., Stinski, U.S. Pat. No. 5,168,062; Bell, U.S. Pat. No. 4,510,245; and Schaffner, U.S. Pat. No. 4,968,615.

The recombinant expression vectors may carry sequences that regulate replication of the vector in host cells (e.g., origins of replication) and selectable marker genes. The selectable marker gene facilitates selection of host cells into which the vector has been introduced (see, e.g., Axel, U.S. Pat. Nos. 4,399,216; 4,634,665 and 5,179,017). For example, typically the selectable marker gene confers resistance to a drug, such as G418, hygromycin or methotrexate, on a host cell into which the vector has been introduced. Frequently used selectable marker genes include the dihydrofolate reductase (DHFR) gene (for use in dhfr-host cells with methotrexate selection/amplification) and the neo gene (for G418 selection).

Vectors encoding $PrP^c$ antagonists can be used for transformation of a suitable host cell. Transformation can be by any suitable method. Methods for introduction of exogenous DNA into mammalian cells are well known in the art and include dextran-mediated transfection, calcium phosphate precipitation, polybrene-mediated transfection, protoplast fusion, electroporation, encapsulation of the polynucleotide(s) in liposomes, and direct microinjection of the DNA into nuclei. In addition, nucleic acid molecules may be introduced into mammalian cells by viral vectors.

Transformation of host cells can be accomplished by conventional methods suited to the vector and host cell employed. For transformation of prokaryotic host cells, electroporation and salt treatment methods can be employed (Cohen et al., *Proc. Natl. Acad. Sci. USA* 69:2110-14 (1972)). For transformation of vertebrate cells, electroporation, cationic lipid or salt treatment methods can be employed. See, e.g., Graham et al., *Virology* 52:456-467 (1973); Wigler et al., *Proc. Natl. Acad. Sci. USA* 76:1373-76 (1979).

Host Cells

Host cells for expression of a $PrP^c$ antagonist for use in a method of the invention may be prokaryotic or eukaryotic. Exemplary eukaryotic host cells include, but are not limited to, yeast and mammalian cells, e.g., Chinese hamster ovary (CHO) cells (ATCC Accession No. CCL61), NIH Swiss mouse embryo cells NIH-3T3 (ATCC Accession No. CRL1658), and baby hamster kidney cells (BHK). Other useful eukaryotic host cells include insect cells and plant cells. Exemplary prokaryotic host cells are *E. coli* and *Streptomyces*.

The host cell line used for protein expression is most preferably of mammalian origin; those skilled in the art are credited with ability to preferentially determine particular host cell lines which are best suited for the desired gene product to be expressed therein. Additional exemplary host cell lines include, but are not limited to NSO, SP2 cells, baby hamster kidney (BHK) cells, monkey kidney cells (COS), human hepatocellular carcinoma cells (e.g., Hep G2), A549 cells DG44 and DUXB11 (Chinese Hamster Ovary lines, DHFR minus), HELA (human cervical carcinoma), CVI (monkey kidney line), COS (a derivative of CVI with SV40 T antigen), R1610 (Chinese hamster fibroblast) BALBC/3T3 (mouse fibroblast), HAK (hamster kidney line), SP2/O (mouse myeloma), P3x63-Ag3.653 (mouse myeloma), BFA-1c1BPT (bovine endothelial cells), RAJI (human lymphocyte) and 293 (human kidney). Host cell lines are typically available from commercial services, the American Tissue Culture Collection or from published literature.

Expression of polypeptides from production cell lines can be enhanced using known techniques. For example, the glutamine synthetase (GS) system is commonly used for enhancing expression under certain conditions. See, e.g., European Patent Nos. 0 216 846, 0 256 055, and 0 323 997 and European Patent Application No. 89303964.4.

A polypeptide produced by a cultured cell as described herein can be recovered from the culture medium as a secreted polypeptide, or, if it is not secreted by the cells, it can be recovered from host cell lysates. As a first step in isolating the polypeptide, the culture medium or lysate is generally centrifuged to remove particulate cell debris. The polypeptide thereafter is isolated, and preferably purified, from contaminating soluble proteins and other cellular components, with the following procedures being exemplary of suitable purification procedures: fractionation on immunoaffinity or ion-exchange columns; ethanol precipitation; reverse phase HPLC; chromatography on silica or on a cation-exchange resin such as DEAE; chromatofocusing; SDS PAGE; ammonium sulfate precipitation; and gel filtration, e.g., with Sephadex™ columns (Amersham Biosciences). Protease inhibitors may be used to inhibit proteolytic degradation during purification. One skilled in the art will appreciate that purification methods suitable for the polypeptide of interest may require modification to account for changes in the character of the polypeptide upon expression in recombinant cell culture.

The purification of polypeptides may require the use of, e.g., affinity chromatography, conventional ion exchange chromatography, sizing chromatography, hydrophobic interaction chromatography, reverse phase chromatography, gel filtration or other conventional protein purification techniques. See, e.g., Deutscher, ed. (1990) "Guide to Protein Purification" in Methods in Enzymology, Vol. 182.

Gene Therapy

A $PrP^c$ antagonist can be produced in vivo in a mammal, e.g., a human patient, using a gene-therapy approach to treatment of a nervous-system disease, disorder or injury, e.g., Alzheimer's disease, in which inhibiting supression of long term potentiation and improving spatial memory performance would be therapeutically beneficial. This involves administration of a suitable PrP c antagonist-encoding nucleic acid operably linked to suitable expression control sequences. Generally, these sequences are incorporated into a viral vector. Suitable viral vectors for such gene therapy include an adenoviral vector, an alphavirus vector, an enterovirus vector, a pestivirus vector, a lentiviral vector, a baculoviral vector, a herpesvirus vector, an Epstein Barr viral vector, a papovaviral vector, a poxvirus vector, a vaccinia viral vector, adeno-associated. viral vector and a herpes simplex viral vector. The viral vector can be a replication-defective viral vector. Adenoviral vectors that have a deletion in its E1 gene or E3 gene are typically used. When an adenoviral vector is used, the vector usually does not have a selectable marker gene.

Expression constructs of $PrP^c$ antagonists may be administered in any biologically effective carrier, e.g. any formulation or composition capable of effectively delivering the $PrP^c$ antagonist gene to cells in vivo. Approaches include insertion of the subject gene in viral vectors including recombinant retroviruses, adenovirus, adeno-associated virus, and herpes simplex virus-1, or recombinant bacterial or eukaryotic plasmids. Viral vectors transfect cells directly; plasmid DNA can be delivered with the help of, for example, cationic liposomes (lipofectin) or derivatized (e.g. antibody conjugated), polylysine conjugates, gramacidin S, artificial viral envelopes or other such intracellular carriers, as well as direct injection of the gene construct or $CaPO_4$ precipitation carried out in vivo.

A preferred approach for in vivo introduction of nucleic acid into a cell is by use of a viral vector containing nucleic acid, e.g. a cDNA, encoding a $PrP^c$ antagonist or $PrP^c$ antisense nucleic acid. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells which have taken up viral vector nucleic acid.

Retrovirus vectors and adeno-associated virus vectors can be used as a recombinant gene delivery system for the transfer of exogenous genes in vivo, particularly into humans. These vectors provide efficient delivery of genes into cells, and the transferred nucleic acids are stably integrated into the chromosomal DNA of the host. The development of specialized cell lines (termed "packaging cells") which produce only replication-defective retroviruses has increased the utility of retroviruses for gene therapy, and defective retroviruses are characterized for use in gene transfer for gene therapy purposes. A replication defective retrovirus can be packaged into virions which can be used to infect a target cell through the use of a helper virus by standard techniques. Protocols for producing recombinant retroviruses and for infecting cells in vitro or in vivo with such viruses can be found in *Current*

*Protocols in Molecular Biology*, Ausubel, F. M. et al. (eds.) Greene Publishing Associates, (1989), Sections 9.10-9.14 and other standard laboratory manuals. Examples of suitable retroviruses include pLJ, pZIP, pWE and pEM which are known to those skilled in the art. Examples of suitable packaging virus lines for preparing both ecotropic and amphotropic retroviral systems include .psi.Crip, .psi.Cre, .psi.2 and .psi.Am. Retroviruses have been used to introduce a variety of genes into many different cell types, including epithelial cells, in vitro and/or in vivo (see for example Eglitis, et al. (1985) *Science* 230:1395-1398; Danos and Mulligan (1988) *Proc. Natl. Acad. Sci. USA* 85:6460-6464; Wilson et al. (1988) *Proc. Natl. Acad. Sci. USA* 85:3014-3018; Armentano et al. (1990) *Proc. Natl. Acad. Sci. USA* 87:6141-6145; Huber et al. (1991) *Proc. Natl. Acad. Sci. USA* 88:8039-8043; Ferry et al. (1991) *Proc. Natl. Acad. Sci. USA* 88:8377-8381; Chowdhury et al. (1991) *Science* 254:1802-1805; van Beusechem et al. (1992) *Proc. Natl. Acad. Sci. USA* 89:7640-7644; Kay et al. (1992) *Human Gene Therapy* 3:641-647; Dai et al. (1992) *Proc. Natl. Acad. Sci. USA* 89:10892-10895; Hwu et al. (1993) *J. Immunol.* 150:4104-4115; U.S. Pat. Nos. 4,868,116; 4,980,286; PCT Application WO 89/07136; PCT Application WO 89/02468; PCT Application WO 89/05345; and PCT Application WO 92/07573).

Another viral gene delivery system useful in the present invention utilizes adenovirus-derived vectors. The genome of an adenovirus can be manipulated such that it encodes and expresses a gene product of interest but is inactivated in terms of its ability to replicate in a normal lytic viral life cycle. See, for example, Berkner et al. (1988) *BioTechniques* 6:616; Rosenfeld et al. (1991) *Science* 252:431-434; and Rosenfeld et al. (1992) *Cell* 68:143-155. Suitable adenoviral vectors derived from the adenovirus strain Ad type 5 d1324 or other strains of adenovirus (e.g., Ad2, Ad3, Ad7 etc.) are known to those skilled in the art. Recombinant adenoviruses can be advantageous in certain circumstances in that they are not capable of infecting nondividing cells and can be used to infect a wide variety of cell types, including epithelial cells (Rosenfeld et al. (1992) cited supra). Furthermore, the virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situ where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al. cited supra; Haj-Ahmand and Graham (1986) *J. Virol.* 57:267).

Yet another viral vector system useful for delivery of the subject gene is the adeno-associated virus (AAV). Reviewed in Ali, 2004, *Novartis Found Symp.* 255:165-78; and Lu, 2004, *Stem Cells Dev.* 13(1):133-45. Adeno-associated virus is a naturally occurring defective virus that requires another virus, such as an adenovirus or a herpes virus, as a helper virus for efficient replication and a productive life cycle. (For a review see Muzyczka et al. (1992) *Curr. Topics in Micro. and Immunol.* 158:97-129). It is also one of the few viruses that may integrate its DNA into non-dividing cells, and exhibits a high frequency of stable integration (see for example Flotte et al. (1992) *Am. J. Respir. Cell. Mol. Biol.* 7:349-356; Samulski et al. (1989) *J. Virol.* 63:3822-3828; and McLaughlin et al. (1989) *J. Virol.* 62:1963-1973). Vectors containing as little as 300 base pairs of AAV can be packaged and can integrate. Space for exogenous DNA is limited to about 4.5 kb. An AAV vector such as that described in Tratschin et al. (1985) *Mol. Cell. Biol.* 5:3251-3260 can be used to introduce DNA into cells. A variety of nucleic acids have been introduced into different cell types using AAV vectors (see for example Hermonat et al. (1984) *Proc. Natl. Acad. Sci. USA* 81:6466-6470; Tratschin et al. (1985) *Mol. Cell. Biol.* 4:2072-2081; Wondisford et al. (1988) *Mol. Endocrinol.* 2:32-39; Tratschin et al. (1984) *J. Virol.* 51:611-619; and Flotte et al. (1993) *J. Biol. Chem.* 268:3781-3790).

In addition to viral transfer methods, such as those illustrated above, non-viral methods can also be employed to cause expression of a $PrP^c$ antagonist polypeptide, fragment, or analog, in the tissue of an animal. Most nonviral methods of gene transfer rely on normal mechanisms used by mammalian cells for the uptake and intracellular transport of macromolecules. In preferred embodiments, non-viral gene delivery systems of the present invention rely on endocytic pathways for the uptake of the subject $PrP^c$ antagonist gene by the targeted cell. Exemplary gene delivery systems of this type include liposomal derived systems, poly-lysine conjugates, and artificial viral envelopes. Other embodiments include plasmid injection systems such as are described in Meuli et al. (2001) *J Invest Dermatol.* 116(1):131-135; Cohen et al. (2000) *Gene Ther* 7(22):1896-905; or Tam et al. (2000) *Gene Ther* 7(21):1867-74.

In a representative embodiment, a gene encoding a $PrP^c$ antagonist polypeptide, active fragment, or analog, can be entrapped in liposomes bearing positive charges on their surface (e.g., lipofectins) and (optionally) which are tagged with antibodies against cell surface antigens of the target tissue (Mizuno et al. (1992) *No Shinkei Geka* 20:547-551; PCT publication WO91/06309; Japanese patent application 1047381; and European patent publication EP-A-43075).

In clinical settings, the gene delivery systems for the therapeutic $PrP^c$ antagonist gene can be introduced into a patient by any of a number of methods, each of which is familiar in the art. For instance, a pharmaceutical preparation of the gene delivery system can be introduced systemically, e.g. by intravenous injection, and specific transduction of the protein in the target cells occurs predominantly from specificity of transfection provided by the gene delivery vehicle, cell-type or tissue-type expression due to the transcriptional regulatory sequences controlling expression of the receptor gene, or a combination thereof. In other embodiments, initial delivery of the recombinant gene is more limited with introduction into the animal being quite localized. For example, the gene delivery vehicle can be introduced by catheter (see U.S. Pat. No. 5,328,470) or by stereotactic injection (e.g. Chen et al. (1994) *Pros. Natl. Acad. Sci. USA* 91: 3054-3057).

The pharmaceutical preparation of the gene therapy construct can consist essentially of the gene delivery system in an acceptable diluent, or can comprise a slow release matrix in which the gene delivery vehicle is imbedded. Alternatively, where the complete gene delivery system can be produced intact from recombinant cells, e.g. retroviral vectors, the pharmaceutical preparation can comprise one or more cells which produce the gene delivery system.

Guidance regarding gene therapy in particular for treating a CNS condition or disorder as described herein can be found, e.g., in U.S. Patent Publication No. 20020193335 (provides methods of delivering a gene therapy vector, or transformed cell, to neurological tissue); U.S. Patent Publication No. 20020187951 (provides methods for treating a neurodegenerative disease using a lentiviral vector to a target cell in the brain or nervous system of a mammal); U.S. Patent Publication No. 20020107213 (discloses a gene therapy vehicle and methods for its use in the treatment and prevention of neurodegenerative disease); U.S. Patent Publication No. 20030099671 (discloses a mutated rabies virus suitable for delivering a gene to the CNS); and U.S. Pat. No. 6,436,708 (discloses a gene delivery system which results in long-term expression throughout the brain); U.S. Pat. No. 6,140,111 (discloses retroviral vectors suitable for human gene therapy in the treatment of a variety of disease); and Kaspar et al., *Mol Ther.* 5:50-56 (2002), Suhr et al., *Arch Neurol.* 56:287-92 (1999); and Wong et al. *Nat Neurosci* 5: 633-639 (2002).

Pharmaceutical Compositions

The $PrP^c$ antagonists used in the methods of the invention, may be formulated into pharmaceutical compositions for administration to mammals, including humans. The pharmaceutical compositions used in the methods of this invention comprise pharmaceutically acceptable carriers, including, e.g., ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions used in the methods of the present invention may be administered by any suitable method, e.g., parenterally, intraventricularly, orally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. As described previously, $PrP^c$ antagonists used in the methods of the invention act in the nervous system to inhibit suppression of long term potentiation, increasing acute memory retention, and improving spatial memory performance.

Accordingly, in certain methods of the invention, the $PrP^c$ antagonists are administered in such a way that they cross the blood-brain barrier. This crossing can result from the physico-chemical properties inherent in the $PrP^c$ antagonist molecule itself, from other components in a pharmaceutical formulation, or from the use of a mechanical device such as a needle, cannula or surgical instruments to breach the blood-brain barrier. Where the $PrP^c$ antagonist is a molecule that does not inherently cross the blood-brain barrier, e.g., a fusion to a moiety that facilitates the crossing, suitable routes of administration are, e.g., intrathecal or intracranial. Where the $PrP^c$ antagonist is a molecule that inherently crosses the blood-brain barrier, the route of administration may be by one or more of the various routes described below.

Sterile injectable forms of the compositions used in the methods of this invention may be aqueous or oleaginous suspension. These suspensions may be formulated according to techniques known in the art using suitable dispersing or wetting agents and suspending agents. The sterile, injectable preparation may also be a sterile, injectable solution or suspension in a non-toxic parenterally acceptable diluent or solvent, for example as a suspension in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as TWEEN®s, (polysorbates) SPAN™s (sorbitans) and other emulsifying agents or bioavailability enhancers which are commonly used in the manufacture of pharmaceutically acceptable solid, liquid, or other dosage forms may also be used for the purposes of formulation.

Compositions containing an agent described herein, e.g., $PrP^c$ antagonists such as soluble $PrP^c$ polypeptides, anti-$PrP^c$ antibodies, antigen binding fragments of anti-$PrP^c$ antibodies and/or a combination therof, $PrP^c$ antagonist polynucleotide and/or a combination thereof may contain suitable pharmaceutically acceptable carriers. For example, they may contain excipients and/or auxiliaries that facilitate processing of the active compounds into preparations designed for delivery to the site of action. Suitable formulations for parenteral administration include aqueous solutions of the active compounds in water-soluble form, for example, water-soluble salts. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances that increase the viscosity of the suspension include, for example, sodium carboxymethyl cellulose, sorbitol and dextran. Optionally, the suspension may also contain stabilizers. Liposomes also can be used to encapsulate the molecules of the invention for delivery into cells or interstitial spaces. Exemplary pharmaceutically acceptable carriers are physiologically compatible solvents, dispersion media, coatings, antibacterial and antifungal agents, isotonic and absorption delaying agents, water, saline, phosphate buffered saline, dextrose, glycerol, ethanol and the like. In some embodiments, the composition comprises isotonic agents, for example, sugars, polyalcohols such as mannitol, sorbitol, or sodium chloride. In some embodiments, the compositions comprise pharmaceutically acceptable substances such as wetting or minor amounts of auxiliary substances such as wetting or emulsifying agents, preservatives or buffers, which enhance the shelf life or effectiveness of the active ingredients.

Parenteral formulations may be a single bolus dose, an infusion or a loading bolus dose followed with a maintenance dose. These compositions may be administered at specific fixed or variable intervals, e.g., once a day, or on an "as needed" basis.

Certain pharmaceutical compositions used in the methods of this invention may be orally administered in an acceptable dosage form including, e.g., capsules, tablets, aqueous suspensions or solutions. Certain pharmaceutical compositions also may be administered by nasal aerosol or inhalation. Such compositions may be prepared as solutions in saline, employing benzyl alcohol or other suitable preservatives, absorption promoters to enhance bioavailability, and/or other conventional solubilizing or dispersing agents.

Compositions of the invention may be in a variety of forms, including, for example, liquid (e.g., injectable and infusible solutions), dispersions, suspensions, semi-solid and solid dosage forms. The preferred form depends on the mode of administration and therapeutic application. For treating tissues in the central nervous system, administration can be, e.g., by injection or infusion into the cerebrospinal fluid (CSF). Administration can also be with one or more agents capable of promoting penetration of a $PrP^c$ antagonist polypeptide across the blood-brain barrier.

The composition can be formulated as a solution, microemulsion, dispersion, liposome, or other ordered structure suitable to high drug concentration. Sterile injectable solutions can be prepared by incorporating the active ingredient in the required amount in an appropriate solvent with one or a combination of ingredients enumerated above, as required, followed by filtered sterilization. Generally, dispersions are prepared by incorporating the active ingredient into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

The active ingredient can be formulated with a controlled-release formulation or device. Examples of such formulations and devices include implants, transdermal patches, and microencapsulated delivery systems. Biodegradable, biocompatible polymers can be used, for example, ethylene vinyl acetate, polyanhydrides, polyglycolic acid, collagen, polyorthoesters, and polylactic acid. Methods for the preparation of such formulations and devices are known in the art. See e.g., *Sustained and Controlled Release Drug Delivery Systems*, J. R. Robinson, ed., Marcel Dekker, Inc., New York, 1978.

Injectable depot formulations can be made by forming microencapsulated matrices of the drug in biodegradable polymers such as polylactide-polyglycolide. Depending on the ratio of drug to polymer, and the nature of the polymer employed, the rate of drug release can be controlled. Other exemplary biodegradable polymers are polyorthoesters and polyanhydrides. Depot injectable formulations also can be prepared by entrapping the drug in liposomes or microemulsions.

Supplementary active compounds can be incorporated into the compositions used in the methods of the invention. In some embodiments, a $PrP^c$ antagonist, e.g., a soluble $PrP^c$ polypeptide, anti-$PrP^c$ antibody or fragment thereof or $PrP^c$ antagonist polynucleotide, is coadministered with another $PrP^c$ antagonist. In addition, a $PrP^c$ antagonist may be coformulated with and/or coadministered with one or more additional therapeutic agents effective to treat, ameliorate or prevent Alzheimer's disease, such as an adrenergic, antiadrenergic, anti-androgen, anti-anginal, anti-anxiety, anticonvulsant, antidepressant, anti-epileptic, antihyperlipidemic, antihyperlipoproteinemic, antihypertensive, anti-inflammatory, antiobessional, antiparkinsonian, antipsychotic, adrenocortical steroid; adrenocortical suppressant; aldosterone antagonist; amino acid; anabolic steroid; analeptic; androgen; blood glucose regulator; cardioprotectant; cardiovascular; cholinergic agonist or antagonist; cholinesterase deactivator or inhibitor, such as galantamine, rivastigmine, tacrine and donepezil; cognition adjuvant or enhancer; dopaminergic; enzyme inhibitor, estrogen, free oxygen radical scavenger; GABA agonist; glutamate antagonist; hormone; hypocholesterolemic; hypolipidemic; hypotensive; immunizing; immunostimulant; monoamine oxidase inhibitor, neuroprotective; N-methyl D-aspartate (NMDA) antagonist, such as memantine; AMPA antagonist, competitive or non-competitive NMDA antagonist; opioid antagonist; potassium channel opener; non-hormonal sterol derivative; post-stroke and post-head trauma treatment; prostaglandin; psychotropic; relaxant; sedative; sedative-hypnotic; selective adenosine antagonist; serotonin antagonist; serotonin inhibitor; selective serotonin uptake inhibitor; serotonin receptor antagonist; sodium and calcium channel blocker; steroid; stimulant; and thyroid hormone and inhibitor agents.

The amount of $PrP^c$ antagonist, e.g., a soluble $PrP^c$ polypeptide, anti-$PrP^c$ antibody or fragment thereof or $PrP^c$ antagonist polynucleotide that may be combined with the carrier materials to produce a single dosage form will vary depending upon the host treated, the type of antagonist used and the particular mode of administration. The composition may be administered as a single dose, multiple doses or over an established period of time in an infusion. Dosage regimens also may be adjusted to provide the optimum desired response (e.g., a therapeutic or prophylactic response).

The methods of the invention use a "therapeutically effective amount" or a "prophylactically effective amount" of a $PrP^c$ antagonist, e.g., a soluble $PrP^c$ polypeptide, anti-$PrP^c$ antibody or fragment thereof or $PrP^c$ antagonist polynucleotide. Such a therapeutically or prophylactically effective amount may vary according to factors such as the disease state, age, sex, and weight of the individual. A therapeutically or prophylactically effective amount is also one in which any toxic or detrimental effects are outweighed by the therapeutically beneficial effects.

A specific dosage and treatment regimen for any particular patient will depend upon a variety of factors, including the particular $PrP^c$ antagonist used, the patient's age, body weight, general health, sex, and diet, and the time of administration, rate of excretion, drug combination, and the severity of the particular disease being treated. Judgment of such factors by medical caregivers is within the ordinary skill in the art. The amount will also depend on the individual patient to be treated, the route of administration, the type of formulation, the characteristics of the compound used, the severity of the disease, and the desired effect. The amount used can be determined by pharmacological and pharmacokinetic principles well known in the art.

Dosage regimens may be adjusted to provide the optimum desired response. For example, a single bolus of a $PrP^c$ antagonist, e.g., a soluble $PrP^c$ polypeptide, anti-$PrP^c$ antibody or fragment thereof or $PrP^c$ antagonist polynucleotide may be administered, several divided doses may be administered over time, or the dose may be proportionally reduced or increased as indicated by the exigencies of the therapeutic situation. It is advantageous to formulate parenteral compositions in dosage unit form for ease of administration and uniformity of dosage. See, e.g., Remington's Pharmaceutical Sciences (Mack Pub. Co., Easton, Pa. 1980).

In addition to the active compound, the liquid dosage form may contain inert ingredients such as water, ethyl alcohol, ethyl carbonate, ethyl acetate, benzyl alcohol, benzyl benzoate, propylene glycol, 1,3-butylene glycol, dimethylformamide, oils, glycerol, tetrahydrofurfuryl alcohol, polyethylene glycols, and fatty acid esters of sorbitan.

Compositions for administration according to the methods of the invention can be formulated so that a dosage of 0.001-10 mg/kg body weight per day of the $PrP^c$ antagonist polypeptide is administered. In some embodiments of the invention, the dosage is 0.01-1.0 mg/kg body weight per day. In some embodiments, the dosage is 0.001-0.5 mg/kg body weight per day.

For treatment with a PrP$^c$ antagonist antibody, the dosage can range, e.g., from about 0.0001 to 100 mg/kg, and more usually 0.01 to 5 mg/kg (e.g., 0.02 mg/kg, 0.25 mg/kg, 0.5 mg/kg, 0.75 mg/kg, 1 mg/kg, 2 mg/kg, etc.), of the host body weight. For example dosages can be 1 mg/kg body weight or 10 mg/kg body weight or within the range of 1-10 mg/kg, preferably at least 1 mg/kg. Doses intermediate in the above ranges are also intended to be within the scope of the invention. Subjects can be administered such doses daily, on alternative days, weekly or according to any other schedule determined by empirical analysis. An exemplary treatment entails administration in multiple dosages over a prolonged period, for example, of at least six months. Additional exemplary treatment regimes entail administration once per every two weeks or once a month or once every 3 to 6 months. Exemplary dosage schedules include 1-10 mg/kg or 15 mg/kg on consecutive days, 30 mg/kg on alternate days or 60 mg/kg weekly. In some methods, two or more monoclonal antibodies with different binding specificities are administered simultaneously, in which case the dosage of each antibody administered falls within the ranges indicated.

In certain embodiments, a subject can be treated with a nucleic acid molecule encoding a PrP$^c$ antagonist polynucleotide. Doses for nucleic acids range from about 10 ng to 1 g, 100 ng to 100 mg, 1 μg to 10 mg, or 30-300 μg DNA per patient. Doses for infectious viral vectors vary from 10-100, or more, virions per dose.

Supplementary active compounds also can be incorporated into the compositions used in the methods of the invention. For example, a soluble PrP$^c$ antagonist polypeptide or a fusion protein may be coformulated with and/or coadministered with one or more additional therapeutic agents.

The invention encompasses any suitable delivery method for the PrP$^c$ antagonist to a selected target tissue, including bolus injection of an aqueous solution or implantation of a controlled-release system. Use of a controlled-release implant reduces the need for repeat injections.

The PrP$^c$ antagonists used in the methods of the invention may be directly infused into the brain. Various implants for direct brain infusion of compounds are known and are effective in the delivery of therapeutic compounds to human patients suffering from neurological disorders. These include chronic infusion into the brain using a pump, stereotactically implanted, temporary interstitial catheters, permanent intracranial catheter implants, and surgically implanted biodegradable implants. See, e.g., Gill et al., supra; Scharfen et al., "High Activity Iodine-125 Interstitial Implant For Gliomas," *Int. J. Radiation Oncology Biol. Phys.* 24(4):583-591 (1992); Gaspar et al., "Permanent. 125I Implants for Recurrent Malignant Gliomas," *Int. J. Radiation Oncology Biol. Phys.* 43(5):977-982 (1999); chapter 66, pages 577-580, Bellezza et al., "Stereotactic Interstitial Brachytherapy," in Gildenberg et al., Textbook of Stereotactic and Functional Neurosurgery, McGraw-Hill (1998); and Brem et al., "The Safety of Interstitial Chemotherapy with BCNU-Loaded Polymer Followed by Radiation Therapy in the Treatment of Newly Diagnosed Malignant Gliomas: Phase I Trial," *J. Neuro-Oncology* 26:111-23 (1995).

The compositions may also comprise PrP$^c$ antagonists dispersed in a biocompatible carrier material that functions as a suitable delivery or support system for the compounds. Suitable examples of sustained release carriers include semipermeable polymer matrices in the form of shaped articles such as suppositories or capsules. Implantable or microcapsular sustained release matrices include polylactides (U.S. Pat. No. 3,773,319; EP 58,481), copolymers of L-glutamic acid and gamma-ethyl-L-glutamate (Sidman et al., *Biopolymers* 22:547-56 (1985)); poly(2-hydroxyethyl-methacrylate), ethylene vinyl acetate (Langer et al., *J. Biomed. Mater. Res.* 15:167-277 (1981); Langer, *Chem. Tech.* 12:98-105 (1982)) or poly-D-(−)-3hydroxybutyric acid (EP 133,988).

In some embodiments of the invention, the PrP$^c$ is administered to a patient by direct infusion into an appropriate region of the brain. See, e.g., Gill et al., "Direct brain infusion of glial cell line-derived neurotrophic factor in Parkinson disease," *Nature Med.* 9: 589-95 (2003). Alternative techniques are available and may be applied to administer the PrP$^c$ antagonists according to the invention. For example, stereotactic placement of a catheter or implant can be accomplished using the Riechert-Mundinger unit and the ZD (Zamorano-Dujovny) multipurpose localizing unit. A contrast-enhanced computerized tomography (CT) scan, injecting 120 ml of omnipaque, 350 mg iodine/ml, with 2 mm slice thickness can allow three-dimensional multiplanar treatment planning (STP, Fischer, Freiburg, Germany). This equipment permits planning on the basis of magnetic resonance imaging studies, merging the CT and MRI target information for clear target confirmation.

The Leksell stereotactic system (Downs Surgical, Inc., Decatur, Ga.) modified for use with a GE CT scanner (General Electric Company, Milwaukee, Wis.) as well as the Brown-Roberts-Wells (BRW) stereotactic system (Radionics, Burlington, Mass.) can be used for this purpose. Thus, on the morning of the implant, the annular base ring of the BRW stereotactic frame can be attached to the patient's skull. Serial CT sections can be obtained at 3 mm intervals though the (target tissue) region with a graphite rod localizer frame clamped to the base plate. A computerized treatment planning program can be run on a VAX 11/780 computer (Digital Equipment Corporation, Maynard, Mass.) using CT coordinates of the graphite rod images to map between CT space and BRW space.

The methods of treatment of diseases and disorders as described herein are typically tested in vitro, and then in vivo in an acceptable animal model, for the desired therapeutic or prophylactic activity, prior to use in humans. Suitable animal models, including transgenic animals, are well known to those of ordinary skill in the art. For example, in vitro assays to demonstrate the differentiation and survival effect of the PrP$^c$ antagonists are described herein. Finally, in vivo tests can be performed by creating transgenic mice which express the PrP$^c$ antagonists or by administering the PrP$^c$ antagonists to transgenic mice, e.g., APPswe/PSEN1ΔE9 transgenic mice. Behavorial testing models, e.g., radial arm water maze (RAWM), can be used to assess spatial memory and learning. See, e.g., Wilcock et al., *J. Neurosci.* 26:5340-5346 (2006).

Pharmaceutical Kits

The present invention also provides kits for use in delivering the PrP$^c$ antagonist (e.g., soluble PrP$^c$ polypeptides, anti-PrP$^c$ antibodies, or PrP$^c$ antagonist polynucleotides) to a mammal. Any suitable container or containers may be used with pharmaceutical kits. Examples of containers include, but are not limited to, glass containers, plastic containers, or strips of plastic or paper.

Each of the pharmaceutical kits may further comprise an administration means. Means for administration include, but are not limited to, syringes and needles, catheters, biolistic injectors, particle accelerators, i.e., "gene guns," pneumatic "needleless" injectors, gelfoam sponge depots, other commercially available depot materials, e.g., hydrogels, osmotic pumps, and decanting, polynucleotide coated sutures, skin patches, or topical applications during surgery.

Each of the pharmaceutical kits can further comprise an instruction sheet for administration of the composition to a mammal. The polynucleotide components of the composition are preferably provided as a liquid solution or they may be provided in lyophilized form as a dried powder or a cake. If the PrP$^c$ antagonist are provided in lyophilized form, the dried powder or cake may also include any salts, auxiliary agents, transfection facilitating agents, and additives of the composition in dried form. Such a kit may further comprise a container with an exact amount of sterile pyrogen-free water, for precise reconstitution of the lyophilized components of the composition.

The container in which the composition is packaged prior to use can comprise a hermetically sealed container enclosing an amount of the lyophilized formulation or a solution containing the formulation suitable for a pharmaceutically effective dose thereof, or multiples of an effective dose. The composition is packaged in a sterile container, and the hermetically sealed container is designed to preserve sterility of the pharmaceutical formulation until use. Optionally, the container can be associated with administration means and/or instruction for use.

EXAMPLES

The invention is further illustrated by the following experimental examples. The examples are provided for illustrative purposes only, and are not to be construed as limiting the scope or content of the invention in any way.

Example 1

Figure 1:
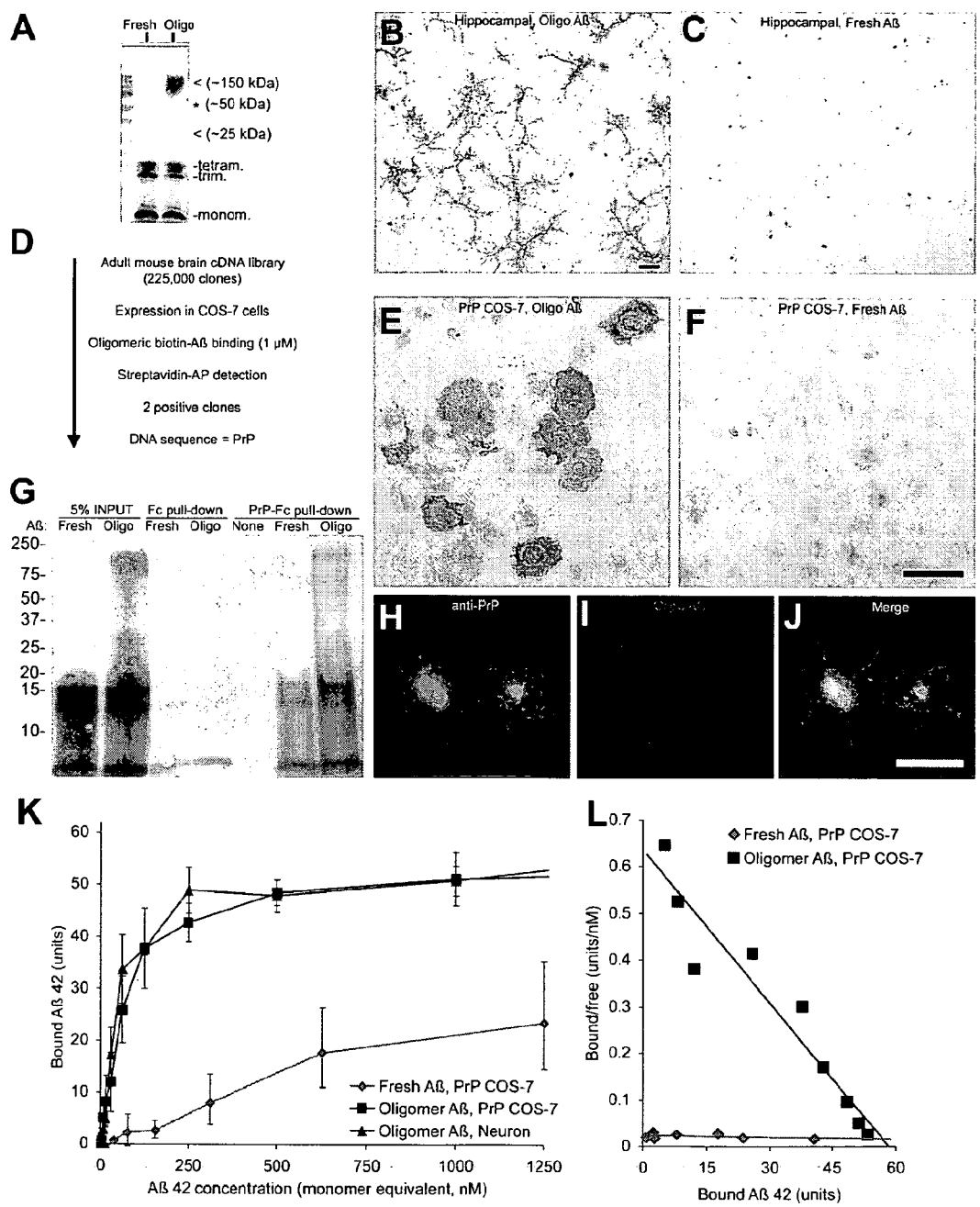
FIG. 1A shows a immunoblot of Aβ42 samples that were incubated for 0 hours (fresh (monomers) or 16 hours (oligomer enriched) in F12 medium and separated by tris-tricine SDS-polyacrylamide gel electrophoresis and probed with 6E10 anti-Aβ antibody.
FIG. 1B-1C shows the binding of oligomeric Aβ42 peptide (40 nM) (B) and monomeric Aβ42 peptide (C) to fully differentiated hippocampal neurons.
FIG. 1D shows the expression cloning strategy.
FIG. 1E-1F shows the binding of 40 nM oligomeric Aβ42 peptide (E) and monomeric Aβ42 peptide (F) to COS-7 expressing $PrP^c$.
FIG. 1G shows an immunoblot of purified Fc-proteins (control Fc and PrP-Fc) that were incubated with fresh or oligomeric Aβ42, separated by tris-tricine SDS-polyacrylamide gel electrophoresis and probed with 6E10 anti-Aβ antibody.
FIG. 1H shows COS-7 cells probed with 7D9 anti-PrP monoclonal antibody.
FIG. 1I shows Aβ42 stained with red fluorescent steptavidin.
FIG. 1J shows the binding of Aβ42 to $PrP^c$-expressing COS-7 cells.
FIG. 1K shows a graph of the binding of fresh and oligomeric Aβ42 to hippocampal neurons and $PrP^c$-expressing COS-7 cells.
FIG. 1L shows a Scatchard analysis of the binding of fresh and oligomeric Aβ42 to $PrP^c$-expressing COS-7 cells.

Expression Cloning Identifies PrP$^c$ as a High Affinity Aβ-Oligomer Binding Site In order to screen for Aβ-oligomer binding sites, we developed an assay with high sensitivity and specificity. We synthesized biotin-tagged amyloid-beta 42-amino acid (Aβ42) peptide (DAEFRHDSGYEVHHQKLVFFAEDVGSNK-GAIIGLMVGGVVIA (SEQ ID NO:18)), denatured the peptide in hexafluoro-2-propanol, allowed oligomers to form in physiological F12 medium for 16 hours, separated them by tris-tricine SDS-polyacrylamide gel electrophoresis and analyzed by immunoblot with 6E10 anti-Aβ antibody. The untagged and N-terminal biotin-tagged Aβ42 peptides were synthesized by the Keck Biotechnology facility at Yale. Oligomer preparations were generated from synthetic peptide following a procedure similar to the ADDL method of Klein. Chromy, et al., *Biochemistry* 42:12749-12760 (2003) (FIG. 1A). Fibrillary Aβ was removed by centrifugation.

Consistent with previous findings for untagged Aβ42-oligomers (Lacor, et al., *J. Neurosci* 27: 796-807 (2007)), biotin-Aβ42-oligomers bind selectively to fully differentiated hippocampal neurons, whereas freshly prepared lower molecular weight biotin-Aβ42 does not (FIGS. 1B and 1C; FIG. 6). Biotin-Aβ42-oligomer binding is enriched in MAP2-positive dendrites, with lower levels in BIII-tubulin positive axons and very low levels in glial cells. The binding to hippocampal neurons is saturable, with an apparent dissociation constant of 50 nM monomer equivalent and no evidence for cooperativity (FIG. 1L). If the Aβ42 species responsible for binding contains 3-10 monomers and represents 10-20% of all biotin-Aβ42 in the preparation, the corrected affinity would be ~2 nM.

A key requirement for expression cloning of Aβ-oligomer binding sites is the existence of a cell line with a low background level of binding. We observed that the monkey COS-7 kidney cell line exhibits less than 5% of the biotin-Aβ42-oligomer binding level seen in differentiated hippocampal neurons. Therefore, we expressed cDNAs from an adult mouse brain library in this cell line and screened for high affinity biotin-Aβ42 binding sites.

In preparation for binding assays, COS-7 cells were transiently transfected with cDNA plasmids and hippocampal neurons was dissected from E18 (18 day) mouse embryos and maintained in Neurobasal A medium. The binding of oligomeric biotin-Aβ42 was detected using avidin-alkaline phosphatase or fluorescent avidin conjugates. Expression cloning of binding sites was as described for other ligands. Rajagopalan, et al., *Nature Cell Biology* 6: 756-762 (2004) and Fournier, et al., *Nature* 409: 341-346 (2001).

From a screen of 225,000 clones, two independent positive clones were isolated and both were found to encode full-length mouse PrP (FIG. 1D, E). Aβ42-oligomers bind to cells expressing the PrP$^c$ conformation. Interaction is not dependent on the PrP$^{Sc}$ conformation required for infectious prion disease. Prusiner, *Proc Natl Acad Sci USA* 95: 13363-13383 (1998). Like hippocampal neurons, PrP$^c$-expressing COS-7 cells have low affinity for freshly prepared low molecular weight biotin-Aβ42 (FIG. 1F). The apparent dissociation constant for biotin-Aβ42-oligomer binding to PrP$^c$-expressing COS-7 cells is indistinguishable from biotin-Aβ42-oligomer binding to hippocampal neurons (FIG. 1K, L). Binding data in K are mean±standard error of the mean (sem) and the Scatchard analysis is presented in FIG. 1L.

In order to assess whether the interaction of biotin-Aβ42-oligomer with PrP$^c$-expressing cells might be mediated by the biotin tag, we prepared untagged Aβ42-oligomer and examined binding to PrP$^c$-expressing cells with anti-Aβ antibody 6E10 (FIG. 1H-J). Untagged Aβ42 binding is selectively localized to PrP$^c$-expressing cells in transiently transfected cultures. Thus, binding is mediated by the Aβ residues.

The simplest model for PrP$^c$ expression inducing Aβ42-oligomer binding is a direct interaction between the two polypeptides. Phosphatidyl-Inositol-specific Phospholipase C treatment to remove Glycosyl-Phosphatidyl-Inositol(GPI)-anchored membrane proteins, including PrP$^c$, abolishes the ability of PrP$^c$-expressing COS-7 cells to bind Aβ42. To see this, binding of oligomeric biotinAβ42 to COS-7 cells, transfected with PrP cDNA or non-transfected cells, was assayed in F12 supplemented with 1 μM Cu$^{++}$. Pre-treatment of PrP cDNA transfected cells with vehicle (PBS) or PI-PLC (phosphatidylinositol-specific phospholipase C from *Bacillus cereus*, 1 unit/ml, 1 h) demonstrates that PI-PLC abolishes the Aβ42 binding, consistent with a direct physical interaction. (data not shown)

To verify this, we examined the interaction of purified PrP-Fc with Aβ42 using affinity chromotography (FIG. 1G). A control Fc protein, immobilized on a resin, retained neither freshly prepared monomeric nor oligomeric preparations of Aβ42. In contrast, PrP-Fc protein retained Aβ42 peptide through a direct physical interaction (FIG. 1G). The pre-incubated oligomeric form of Aβ42 was retained to a greater degree than the freshly prepared peptide, but the preference of PrP for Aβ-oligomer was not as complete with the concentrated solid-phase purified reagents as in cell binding studies. We conclude that PrP$^c$ expressed at the cell surface provides a high-affinity binding site for oligomeric Aβ42 that matches the characteristics of binding sites in hippocampal neurons.

Example 2

Characterization of Aβ-Oligomer Binding to PrP$^c$

One striking aspect of Aβ42-oligomer binding to neurons is the dependence on developmental stage. There is minimal binding to neurons when the E18 (18 day) mouse hippocampus is first dissociated and placed into culture. Not until 15-20 days have elapsed in vitro does Aβ42-oligomer binding to hippocampal neurons become robust (FIG. 2A). Endogenous proteins mediating Aβ42-oligomer binding are expected to have a similar pattern of expression. By immunoblot, the level of PrP$^c$ expression closely matches this developmental pattern (FIG. 2B). By immunocytochemistry, PrP$^c$ expression is largely restricted to MAP2 positive dendrites of fully differentiated hippocampal neurons (data not shown). These observations lend further support to the hypothesis that PrP$^c$ is a binding site for Aβ42-oligomers in vivo. If $^{PrPc}$ were the only cellular binding site for Aβ42-oligomers, then no binding would be detected in hippocampal cultures from Prnp −/− knockout mice (Zurich strain) at 20 Days in Vitro (DIV). Because we find that Aβ42-oligomer binding is detectable in such cultures (data not shown), PrP$^c$ cannot be the only cell surface molecule capable of binding Aβ42-oligomers.

We mapped the Aβ42-oligomer binding site using PrP deletion mutants (FIG. 3A). Each of the mutant proteins was expressed at the surface of COS-7 cells by live staining with anti-PrP antibodies, 6D11 and 7D9, so differences in binding cannot be attributed to expression levels. COS-7 cells transfected with indicated expression vectors encoding either full-length PrP$^C$ or various PrP$^C$ deletion constructs. 2 days after transfection, the cells were incubated with 6D11 or 7D9 PrP$^C$ monoclonal antibodies. After washing and formaldehyde-fixation, the bound antibodies were visualized by fluorescent secondary antibodies, and nuclei were stained with DAPI. (data not shown). Deletion of the N-terminal Copper ion binding domain and the central domain (Δ32-121) abrogates binding, indicating that the globular domain alone cannot mediate binding. The hydrophobic 105-125 region is not a major determinant of binding, since the Δ105-125 protein binds Aβ42-oligomers indistinguishably from full length PrP$^c$, and since the Δ32-106 variant behaves like the Δ32-121 variant, having no Aβ42-oligomer affinity. (FIG. 3A). However, these two deletion constructs (Δ32-121 and Δ32-106) were detected by 7D9 antibody, indicating that the mutant proteins were displayed on the plasma membrane. 7D9 failed to bind to a PrP$^C$ deletion construct lacking amino acids 105-125 indicating that this region is likely the epitope for 7D9.

To distinguish whether the 95-110 charge cluster or the Copper ion binding domain is crucial for Aβ42 binding, a deletion mutant lacking the Copper ion binding domain was expressed. The Δ52-91 exhibits significant Aβ42 binding, implicating the 95-110 region as a principal site for Aβ42-oligomer binding. (FIG. 3A).

As an alternative method to localize Aβ42 binding interaction domains in PrP$^c$, we screened a panel of anti-PrP antibodies (FIG. 3B-D; FIG. 7). COS-7 cells transfected with PrP cDNA were pre-incubated with indicated concentrations of antibodies in F12 at 22° C. for 1 h. Next, oligomeric Aβ42 was added to a final concentration of 250 nM. After 2 h, the cells were washed, fixed, and bound biotin-Aβ42 was visualized by streptavidin-AP.

From the initial pool of seven antibodies, only one (6D11) blocked the binding of Aβ42 assemblies to PrP$^c$ with an IC50 of 1 nM (FIG. 3B, C). Micrographs demonstrate that 6D11 but not 7D9 antibody at 30 nM blocks Aβ42 binding detected by streptavidin-AP. (FIG. 3B) The 6D11 blockade is epitope-specific since the 7D9 antibody binds avidly to a different epitope but fails to block Aβ42 binding (FIG. 3A-C). The epitope for 6D11 corresponds to aa 93-109 of mouse PrP$^c$, matching the conclusion from the deletion analysis that the 95-110 region is a primary determinant of Aβ42 binding. To confirm this hypothesis, we examined the effect of an additional antibody (8G8) with an overlapping epitope, aa 95-110. The 8G8 antibody blocked Aβ42-PrP$^c$ interaction, though with a lesser potency than 6D11. (FIG. 3D and FIG. 7)

The blockade of Aβ42 binding to PrP by 6D11 was not due to the superior ability of 6D11 to recognize PrP, since both 7D9 and 6D11 bound avidly to PrP and neither antibody showed non-specific binding to non-transfected cells by fluorescence microscopy. (data not shown)

The effect of 6D11 was not caused by internalization of PrP$^c$, since similar cell surface levels of PrP$^c$ were detectable after 6D11 pre-incubation by fluorescence microscopy. (data not shown)

To show that 6D11 is highly specific for PrP$^c$, both adult wild-type and Prnp −/− (Zurich) mouse brains were fresh-frozen within one mold filled with tissue-freezing medium. Samples (14 μm) containing sagittal sections of both brains were dried on microsope slide in dessicator at 22° C. for 30 min. The sections were then rehydrated with F12 medium, incubated for 1 hr with 6D11 antibody, washed twice with F12, fixed in 4% formaldehyde for 15 min, and rinsed with phosphate-buffered saline. The sections were subsequently treated with fluorescent secondary antibodies and DAPI. 6D11 antibody failed to bind to brain sections from Prnp −/− brains, but demonstrated widespread PrP$^C$ expression in the wild-type brain. This result shows that the 6D11 antibody is highly specific for PrP$^c$, as no immunoreactivity was observed in Prnp −/− (Zurich) null brain sections nor is there any reactivity to Aβ42. (data not shown) We conclude that the central 95-110 segment of PrP$^c$ mediates Aβ42 binding in a 6D11-sensitive manner. The contribution of this domain to non-infectious PrP$^c$-mediated neurodegeneration (Baumann, et al., *EMBO J* 26: 538-547 (2007) and Li, et al., *EMBO J* 26: 548-558 (2007)) provides a possible link to the deleterious effect of Aβ42-oligomers.

Example 3

PrP$^c$ Mediates Aβ-Oligomer Inhibition of Hippocampal LTP

While the above data demonstrate that PrP$^c$ is a high affinity binding site for soluble Aβ42-oligomers, they do not assess its functional role as a receptor mediating pathological actions of Aβ. It has been noted by several laboratories that soluble Aβ42-oligomers potently suppress long-term potentiation (LTP) of the Schaffer collateral pathway between hippocampal CA3 and CA1 pyramidal cells. Walsh, et al., *Nature* 416: 535-539 (2002) and Knobloch, et al., *J Neurosci* 27: 7648-7653 (2007). Therefore, we compared the effects of soluble Aβ42-oligomers on LTP measured from slices of wild-type versus Prnp −/− mice (Zurich). Bueler, et al., *Nature* 356: 577-582 (1992). Hippocampal slices (400 μm) were prepared from adult mice and bathed in oxygenated artificial cerebrospinal fluid (aCSF). The Schaffer collateral pathway was stimulated with a bipolar tungsten electrode at 0.033 Hz at levels that evoked less than 50% of maximal EPSPs. Evoked CA1 field potentials were recorded through a 3 MΩ micropipette filled with aCSF and the slope of the EPSP was determined (Clampfit, Molecular Devices). Aβ42 was bath applied by continuous perfusion for 20-40 minutes before inducing long-term potentiation by stimulation with ten 100 Hz trains at five pulses delivered at 5 Hz.

As reported previously, soluble Aβ42-oligomers (500 nM total peptide) block nearly all LTP in hippocampal slices from wild-type mice (FIG. 4A, D). Thus, the initial slope of the excitatory postsynaptic potential (EPSP) after theta burst stimulation is augmented by 85% in control but only by 15% in slices exposed to Aβ42-oligomer preparations for 30 minutes. In slices from PrP null mice without Aβ42 treatment, Schaffer collateral LTP is indistinguishable from baseline levels of wild type mice (FIG. 4B), as described previously. Lledo, et al., *Proc Natl Acad Sci USA* 93: 2403-2407 (1996). Strikingly, there is no inhibition of LTP by Aβ42-oligomers in the Prnp −/− slices (FIG. 4B, D).

The lack of Aβ42 sensitivity for LTP in Prnp −/− slices suggests that $PrP^c$ acts as a receptor for Aβ42-oligomers mediating inhibition of LTP in wild-type slices. Alternatively, the chronic loss of $PrP^c$ may lead to developmental and/or compensatory effects that account indirectly for Aβ42-oligomer ineffectiveness. To separate these possibilities, we treated wild-type slices with the 6D11 anti-PrP antibody (100 nM) shown to block Aβ42 binding acutely (FIG. 4D). Antibodies were bath applied by continuous perfusion for 20-40 minutes before inducing long-term potentiation by stimulation with ten 100 Hz trains at five pulses delivered at 5 Hz. In 6D11-pretreated wild-type slices, the later addition of Aβ42-oligomer preparations did not reduce the magnitude of EPSP slope augmentation by theta burst stimulation (FIG. 4D). Thus, we conclude that $PrP^c$ exerts a receptor action acutely to mediate Aβ42-oligomer inhibition of synaptic plasticity in the hippocampal slice.

Example 4

Anti-$PrP^c$ Antibody Reverses a Memory Deficit in APP-PSEN1 Transgenic Mice

Transgenic mouse models of Alzheimer's disease show deficits in spatial memory function. Chen, et al., *Nature* 408: 975-979 (2000); Chapman, et al., *Nat Neurosci* 2: 271-276 (1999) and Park, et al., *J Neurosci* 26: 13279-13286 (2006). To the extent that $PrP^c$ acts as a receptor for Aβ42-oligomers, such deficits may be reversed by specific PrP antagonism. The 6D11 mouse monoclonal antibody blocks Aβ42 binding to $PrP^c$ and also the ability of Aβ42 to inhibit LTP. Therefore, we infused this antibody into transgenic mice expressing human APPswe (Swedish amyloid precursor protein mutation) and PSEN1ΔE9 (exon 9 deletion of the presenilin 1 gene). Park, et al., *J Neurosci* 26: 13279-13286 (2006). The APPswe/PSEN1ΔE9 transgenic mice (Jankowsky, et al., *Human Molecular Genetics* 13: 159-170 (2004)) were obtained from Jackson Laboratories, Prnp −/− mice (Edinburgh strain) (Manson, et al., *Molecular neurobiology* 8: 121-127 (1994)) on a C57B16 background were obtained from Dr. Chesebro of the Rocky Mountain Laboratories and Prnp −/− mice (Zurich I) (Bueler, et al., *Nature* 356: 577-582 (1992)) on a mixed C57×129 background from the European Mutant Mouse Archive.

Previous studies have indicated that some PrP antibodies but not others induce neuronal damage in wild type mouse brain (Solforosi, et al., *Science* 303: 1514-1516 (2004)); we observed no evidence of 6D11-induced toxicity (data not shown). The intracerebroventricular (i.c.v.) injection of 6D11 or control mouse IgG was performed at 7 months of age, when this transgenic strain first demonstrates Aβ plaque deposition and memory deficits. Park, et al., *J Neurosci* 26: 13279-13286 (2006); Jankowsky, et al., *Human Molecular Genetics* 13: 159-170 (2004) and Park, et al., *J Neurosci* 26: 1386-1395 (2006). For antibody injection studies, mice were anesthetized with isofluorane and a craniotomy was created. Thirty µg of antibody in 3 µl of sterile saline was injected stereotaxically into one lateral ventricle over 5 minutes. Wang, et al., *Ann Neurol* 60:540-549 (2006) and Lee, et al., *J Neurosci* 24: 6209-6217 (2004).

A radial arm water maze with 6 arms was utilized for spatial memory testing as described previously. Park, et al., *J Neurosci* 26: 13279-13286 (2006). Immediately before injection, mild deficits in spatial memory learning were apparent for the transgenic mice in the radial arm water maze testing training protocol that included 3 blocks of 5 swims each day (15 swims) for 2 days. (FIG. 5A) Park, et al., *J Neurosci* 26: 1386-1395 (2006). Mice were trained to a new escape location beginning the day after antibody i.c.v. injection of 6D11 or control IgG, and no differences between the two groups of antibody-injected transgenic mice was observed (FIG. 5B). In acute i.c.v. administration studies of amyloid beta star 56 (Aβ56*), which is a cluster of approximately 10 amyloid beta peptides, the retention of spatial memories is sensitive to Aβ-oligomer disruption while spatial learning per se is relatively resistant. Lesne, et al., *Nature* 440: 352-357 (2006). Therefore, mice injected with 6D11 or control IgG were assessed for retention of the newly learned spatial memory at 4 and 8 days after the post-injection training session (6 or 10 days after antibody injection). The 6D11-treated group made significantly fewer errors than did the control IgG-treated cohort (FIG. 5C). This difference is due to improved retention of the learned memory, rather than swimming talent or motivation, since escape to a visible platform was not altered by 6D11 versus control IgG injection (xx±y sec n=z for IgG versus xx±y sec n=z for 6D11). Improved memory retention after the acute blockade of the $PrP^c$ binding site for Aβ42-oligomer in these AD model mice is consistent with $PrP^c$ serving as a pathological receptor for Aβ42 peptide oligomers.

What is claimed is:

1. A method of reducing or inhibiting the ability of Aβ-oligomers to bind to PrP$^c$ in a subject having Alzheimer's disease (AD), comprising administering to the subject a therapeutically effective amount of a PrPc antagonist comprising an anti-PrPc antibody, or antigen-binding fragment thereof, which specifically binds to an epitope consisting essentially of amino acids 95 to 110 of SEQ ID NOs:2, 4, or 6.

2. The method of claim 1, wherein said anti-PrPc antibody is a monoclonal antibody.

3. The method of claim 2, wherein said monoclonal antibody is 6D11.

4. The method of claim 2, wherein said monoclonal antibody is 8G8.

5. The method of claim 1, wherein said anti-PrPc antibody specifically binds to the same epitope as 6D11.

6. The method of claim 1, wherein said anti-PrPc antibody specifically binds to the same epitope as 8G8.

7. The method of claim 1, further comprising administering an additional therapeutic agent.

8. A method of inhibiting suppression of long term potentiation (LTP) in a subject having Alzheimer's disease (AD), comprising administering to the subject a therapeutically effective amount of a PrPc antagonist comprising an anti-PrPc antibody, or antigen-binding fragment thereof, which specifically binds to an epitope consisting essentially of amino acids 95 to 110 of SEQ ID NOs:2, 4, or 6.

9. The method of claim 8, wherein said anti-PrPc antibody is a monoclonal antibody.

10. The method of claim 9, wherein said monoclonal antibody is 6D11.

11. The method of claim 9, wherein said monoclonal antibody is 8G8.

12. The method of claim 8, wherein said anti-PrPc antibody specifically binds to the same epitope as 6D11.

13. The method of claim 8, wherein said anti-PrPc antibody specifically binds to the same epitope as 8G8.

14. The method of claim 8, further comprising administering an additional therapeutic agent.

15. A method of improving or increasing spatial memory performance in a subject having Alzheimer's disease (AD), comprising administering to the subject a therapeutically effective amount of a PrPc antagonist comprising an anti-PrPc antibody, or antigen-binding fragment thereof, which specifically binds to an epitope consisting essentially of amino acids 95 to 110 of SEQ ID NOs:2, 4, or 6.

16. The method of claim 15, wherein said anti-PrPc antibody is a monoclonal antibody.

17. The method of claim 16, wherein said monoclonal antibody is 6D11.

18. The method of claim 16, wherein said monoclonal antibody is 8G8.

19. The method of claim 15, wherein said anti-PrPc antibody specifically binds to the same epitope as 6D11.

20. The method of claim 15, wherein said anti-PrPc antibody specifically binds to the same epitope as 8G8.

21. The method of claim 15, further comprising administering an additional therapeutic agent.

22. A method of improving or increasing acute memory retention in a subject having Alzheimer's disease (AD), comprising administering to the subject a therapeutically effective amount of a PrPc antagonist comprising an anti-PrPc antibody, or antigen-binding fragment thereof, which specifically binds to an epitope consisting essentially of amino acids 95 to 110 of SEQ ID NOs:2, 4, or 6.

23. The method of claim 22, wherein said anti-PrPc antibody is a monoclonal antibody.

24. The method of claim 23, wherein said monoclonal antibody is 6D11.

25. The method of claim 23, wherein said monoclonal antibody is 8G8.

26. The method of claim 22, wherein said anti-PrPc antibody specifically binds to the same epitope as 6D11.

27. The method of claim 22, wherein said anti-PrPc antibody specifically binds to the same epitope as 8G8.

28. The method of claim 22, further comprising administering an additional therapeutic agent.

* * * * *

UNITED STATES PATENT AND TRADEMARK OFFICE
CERTIFICATE OF CORRECTION

PATENT NO. : 9,217,036 B2
APPLICATION NO. : 12/597535
DATED : December 22, 2015
INVENTOR(S) : Strittmatter et al.

It is certified that error appears in the above-identified patent and that said Letters Patent is hereby corrected as shown below:

In the Specification

In Column 1, above "REFERENCE TO A SEQUENCE LISTING SUBMITTED ELECTRONICALLY VIA EFS-WEB" at Line 10, please insert the following:
--GOVERNMENT LICENSE RIGHTS
This invention was made with government support under NS033020, NS056485, NS042304, NS039962 and NS035476 awarded by National Institutes of Health. The Government has certain rights in the invention.--

Signed and Sealed this
Eighth Day of December, 2020

Andrei Iancu
*Director of the United States Patent and Trademark Office*

SEQUENCE LISTING

```
<160> NUMBER OF SEQ ID NOS: 18

<210> SEQ ID NO 1
<211> LENGTH: 2415
<212> TYPE: DNA
<213> ORGANISM: Homo sapiens

<400> SEQUENCE: 1
cggcgccgcg agcttctcct ctcctcacga ccgaggcaga gcagtcatta tggcgaacct      60
tggctgctgg atgctggttc tctttgtggc cacatggagt gacctgggcc tctgcaagaa     120
```

```
gcgcccgaag cctggaggat ggaacactgg gggcagccga tacccggggc agggcagccc    180
tggaggcaac cgctacccac ctcagggcgg tggtggctgg gggcagcctc atggtggtgg    240
ctgggggcag cctcatggtg gtggctgggg gcagccccat ggtggtggct ggggacagcc    300
tcatggtggt ggctggggtc aaggaggtgg cacccacagt cagtggaaca agccgagtaa    360
gccaaaaacc aacatgaagc acatggctgg tgctgcagca gctggggcag tggtgggggg    420
ccttggcggc tacatgctgg gaagtgccat gagcaggccc atcatacatt tcggcagtga    480
ctatgaggac cgttactatc gtgaaaacat gcaccgttac cccaaccaag tgtactacag    540
gcccatggat gagtacagca accagaacaa ctttgtgcac gactgcgtca atatcacaat    600
caagcagcac acggtcacca caaccaccaa gggggagaac ttcaccgaga ccgacgttaa    660
gatgatggag cgcgtggttg agcagatgtg tatcacccag tacgagaggg aatctcaggc    720
ctattaccag agaggatcga gcatggtcct cttctcctct ccacctgtga tcctcctgat    780
ctctttcctc atcttcctga tagtgggatg aggaaggtct tcctgttttc accatctttc    840
taatcttttt ccagcttgag ggaggcggta tccacctgca gccttttag tggtggtgtc    900 tcactctttc ttctctcttt gtcccggata ggctaatcaa taccctggc actgatgggc    960 actggaaaac atagagtaga cctgagatgc tggtcaagcc cccttgatt gagttcatca    1020 tgagccgttg ctaatgccag gccagtaaaa gtataacagc aaataaccat tggttaatct    1080
ggacttattt ttggacttag tgcaacaggt tgaggctaaa acaaatctca gaacagtctg    1140
aaataccttt gcctggatac ctctggctcc ttcagcagct agagctcagt atactaatgc    1200
cctatcttag tagagatttc atagctattt agagatattt tccattttaa gaaaacccga    1260
caacatttct gccaggtttg ttaggaggcc acatgatact tattcaaaaa atcctagag    1320 attcttagct cttgggatgc aggctcagcc cgctggagca tgagctctgt gtgtaccgag    1380
aactggggtg atgtttttact tttcacagta tgggctacac agcagctgtt caacaagagt    1440
aaatattgtc acaacactga acctctggct agaggacata ttcacagtga acataactgt    1500
aacatatatg aaaggcttct gggacttgaa atcaaatgtt tgggaatggt gcccttggag    1560
gcaacctccc attttagatg tttaaaggac cctatatgtg gcattccttt ctttaaacta    1620
taggtaatta aggcagctga aaagtaaatt gccttctaga cactgaaggc aaatctcctt    1680
tgtccattta cctggaaacc agaatgattt tgacatacag gagagctgca gttgtgaaag    1740
caccatcatc atagaggatg atgtaattaa aaaatggtca gtgtgcaaag aaaagaactg    1800
cttgcatttc tttatttctg tctcataatt gtcaaaaacc agaattaggt caagttcata    1860
gtttctgtaa ttggcttttg aatcaaagaa tagggagaca atctaaaaaa tatcttaggt    1920
tggagatgac agaaatatga ttgatttgaa gtggaaaaag aaattctgtt aatgttaatt    1980
aaagtaaaat tattccctga attgtttgat attgtcacct agcagatatg tattactttt    2040
ctgcaatgtt attattggct tgcactttgt gagtatctat gtaaaaatat atatgtatat    2100
aaaatatata ttgcatagga cagacttagg agttttgttt agagcagtta acatctgaag    2160
tgtctaatgc attaactttt gtaaggtact gaatacttaa tatgtgggaa acccttttgc    2220
gtggtcctta ggcttacaat gtgcactgaa tcgtttcatg taagaatcca agtggacac    2280 cattaacagg tctttgaaat atgcatgtac tttatatttt ctatatttgt aactttgcat    2340
gttcttgttt tgttatataa aaaaattgta aatgtttaat atctgactga aattaaacga    2400
gcgaagatga gcacc                                                    2415
```

<210> SEQ ID NO 2
<211> LENGTH: 253
<212> TYPE: PRT
<213> ORGANISM: Homo sapiens

<400> SEQUENCE: 2

```
Met Ala Asn Leu Gly Cys Trp Met Leu Val Leu Phe Val Ala Thr Trp
1               5                   10                  15
Ser Asp Leu Gly Leu Cys Lys Lys Arg Pro Lys Pro Gly Gly Trp Asn
            20                  25                  30
Thr Gly Gly Ser Arg Tyr Pro Gly Gln Gly Ser Pro Gly Gly Asn Arg
        35                  40                  45
Tyr Pro Pro Gln Gly Gly Gly Trp Gly Gln Pro His Gly Gly Gly
    50                  55                  60
Trp Gly Gln Pro His Gly Gly Gly Trp Gly Gln Pro His Gly Gly Gly
65                  70                  75                  80
Trp Gly Gln Pro His Gly Gly Gly Trp Gly Gln Gly Gly Gly Thr His
                85                  90                  95
Ser Gln Trp Asn Lys Pro Ser Lys Pro Lys Thr Asn Met Lys His Met
            100                 105                 110
Ala Gly Ala Ala Ala Gly Ala Val Val Gly Gly Leu Gly Gly Tyr
        115                 120                 125
Met Leu Gly Ser Ala Met Ser Arg Pro Ile Ile His Phe Gly Ser Asp
    130                 135                 140
Tyr Glu Asp Arg Tyr Tyr Arg Glu Asn Met His Arg Tyr Pro Asn Gln
145                 150                 155                 160
Val Tyr Tyr Arg Pro Met Asp Glu Tyr Ser Asn Gln Asn Asn Phe Val
                165                 170                 175
His Asp Cys Val Asn Ile Thr Ile Lys Gln His Thr Val Thr Thr Thr
            180                 185                 190
Thr Lys Gly Glu Asn Phe Thr Glu Thr Asp Val Lys Met Met Glu Arg
        195                 200                 205
Val Val Glu Gln Met Cys Ile Thr Gln Tyr Glu Arg Glu Ser Gln Ala
    210                 215                 220
Tyr Tyr Gln Arg Gly Ser Ser Met Val Leu Phe Ser Ser Pro Pro Val
225                 230                 235                 240
Ile Leu Leu Ile Ser Phe Leu Ile Phe Leu Ile Val Gly
                245                 250
```

<210> SEQ ID NO 3
<211> LENGTH: 2115
<212> TYPE: DNA
<213> ORGANISM: Rattus norvegicus

<400> SEQUENCE: 3

| | | | | |
|---|---|---|---|---|
| ttcaaaactg | aaccatttca | acccaactga | agtattctgc | cttcttagcg | gtaccagtcc | 60 |
| ggtttaggag | agccaagccg | actatcagcc | atcatggcga | accttggcta | ctggctgctg | 120 |
| gccctctttg | tgactacatg | tactgatgtt | ggcctctgca | aaaagcggcc | aaagcctgga | 180 |
| gggtggaaca | ctggtggaag | ccggtaccct | gggcagggaa | gccctggagg | caaccgttac | 240 |
| ccacctcaga | gtggtggtac | ctgggggcag | ccccatggtg | gtggctgggg | acaacctcat | 300 |
| ggtggtggct | gggacaacc | tcatggtggt | ggctggggtc | agccccatgg | cggggctgg | 360 |
| agtcaaggag | gggtacccca | taatcagtgg | aacaagccca | gcaagccaaa | accaacctc | 420 |
| aagcatgtgg | caggggctgc | cgcagctggg | gcagtagtgg | ggggccttgg | tggctacatg | 480 |

```
ttggggagtg ccatgagcag gcccatgctc cattttggca acgactggga ggaccgctac    540
taccgagaaa acatgtaccg ttaccctaac caagtgtact acaggccggt ggatcagtac    600
agcaaccaga caacttcgt gcacgactgt gtcaatatca ccatcaagca gcatacagtc     660
accaccacca ccaaggggga gaacttcacg gagaccgacg tgaagatgat ggagcgtgtg    720
gtggagcaga tgtgcgtcac ccagtatcag aaggagtccc aggcctatta cgacgggaga    780
agatctagcg ccgtgctttt ctcctcccct cctgtgatcc tcctcatctc cttcctcatc    840
ttcctgatcg tgggatgagg aggccttcct gcttgttcct tctcattctc gtggtctagg    900 ctggggagg ggttacccac ctgtagctct ttcaattgag gtggtgtctc attcttgctt     960
ctctttgtcc cccataggct aatacccttg gcagtgatgg gtctggggaa atgtacagta    1020
gaccagatgc tattcgcttc agcgtccttt gattgagtcc atcatgggcc agggttaaca    1080
ccaggccagt aagaatataa caccaaataa ctgctggcta gtcagggctt tgttttggtc    1140
tactgagtaa atactgtgta acccctgaat tgtacccaga ggacatggtg acagagacac    1200
acataactta gtataggcaa agggttctat agccaaagaa gccactgtgt gggcatggca    1260
ccctggaaaa cagcctcccg cctgggatat ctagagcatc cacatgtgga attctttctt    1320
ttctaacata accatagct gattgaaggc aacaagaaaa agaatcaaat tatcctactg      1380
acattgaaag caaactgtgt tcattcccta ggcgctggaa tgattttttag ccttggatta   1440 aaccaggaga ttttgactct gaggagaacc agcagtacaa aagcatggtc tcctgtgatg    1500
ggagagatgg tgaagggaca aaggcaagac ccctgcgttt cttcatttct gtctcataat    1560
tatcaagagc tagaattagg tcgtgcccta agtttctgta ctcgtatttg aactggacaa    1620
caaagagaca atctacaaat tctcttgggc tgcagaggag agaaataggc tccattccaa    1680
agtggaaaga gaaattctgc tagcattgtc taagtaaggc taacttttcc ttaaatcgct    1740
ttgtatttcc cccagcagac atcacaaccc tgtgatcggt tcagcctgca ccgcgggtgt    1800
tctgtgtaga atatataaat ataacttcaa gcttaggcct tctattttaa agcatctgaa    1860
gtgtggaacg cactggccgt tctgtgcagt actaagtgtg acccttgggc tttcaatgtg    1920
cactcggttc cgtatgattc caaagtagag ccctagctgg tcttcgaatc tgcatgtact    1980
tcacgttttc tatatttgta acttcgcatg tatttgtttt gtcatataaa agtttataa     2040 atgtttgcta tctgactgac attaaataga agctatgatg agcaaaaaaa aaaaaaaaa    2100 aaaaaaaaaa aaaaa                                                    2115
```

<210> SEQ ID NO 4
<211> LENGTH: 254
<212> TYPE: PRT
<213> ORGANISM: Rattus norvegicus

<400> SEQUENCE: 4

```
Met Ala Asn Leu Gly Tyr Trp Leu Leu Ala Leu Phe Val Thr Thr Cys
1               5                   10                  15

Thr Asp Val Gly Leu Cys Lys Lys Arg Pro Lys Pro Gly Gly Trp Asn
                20                  25                  30

Thr Gly Gly Ser Arg Tyr Pro Gly Gln Gly Ser Pro Gly Gly Asn Arg
            35                  40                  45

Tyr Pro Pro Gln Ser Gly Gly Thr Trp Gly Gln Pro His Gly Gly Gly
        50                  55                  60

Trp Gly Gln Pro His Gly Gly Gly Trp Gly Gln Pro His Gly Gly Gly
65                  70                  75                  80
```

| | | | | | | | | | | | |
|---|---|---|---|---|---|---|---|---|---|---|---|
| Trp | Gly | Gln | Pro | His | Gly | Gly | Trp | Ser | Gln | Gly | Gly | Thr | His |
| | | | | 85 | | | | 90 | | | | 95 | |

Trp Gly Gln Pro His Gly Gly Trp Ser Gln Gly Gly Thr His
            85                  90                  95

Asn Gln Trp Asn Lys Pro Ser Lys Pro Lys Thr Asn Leu Lys His Val
            100                 105                 110

Ala Gly Ala Ala Ala Gly Ala Val Val Gly Leu Gly Gly Tyr
            115                 120                 125

Met Leu Gly Ser Ala Met Ser Arg Pro Met Leu His Phe Gly Asn Asp
    130                 135                 140

Trp Glu Asp Arg Tyr Tyr Arg Glu Asn Met Tyr Arg Tyr Pro Asn Gln
145                 150                 155                 160

Val Tyr Tyr Arg Pro Val Asp Gln Tyr Ser Asn Gln Asn Asn Phe Val
            165                 170                 175

His Asp Cys Val Asn Ile Thr Ile Lys Gln His Thr Val Thr Thr Thr
            180                 185                 190

Thr Lys Gly Glu Asn Phe Thr Glu Thr Asp Val Lys Met Met Glu Arg
            195                 200                 205

Val Val Glu Gln Met Cys Val Thr Gln Tyr Gln Lys Glu Ser Gln Ala
    210                 215                 220

Tyr Tyr Asp Gly Arg Arg Ser Ser Ala Val Leu Phe Ser Ser Pro Pro
225                 230                 235                 240

Val Ile Leu Leu Ile Ser Phe Leu Ile Phe Leu Ile Val Gly
            245                 250

<210> SEQ ID NO 5
<211> LENGTH: 2097
<212> TYPE: DNA
<213> ORGANISM: Mus musculus

<400> SEQUENCE: 5

```
aattccttca gaactgaacc atttcaaccg agctgaagca ttctgccttc ctagtggtac      60
cagtccaatt taggagagcc aagcagacta tcagtcatca tggcgaacct tggctactgg    120
ctgctggccc tctttgtgac tatgtggact gatgtcggcc tctgcaaaaa gcggccaaag    180
cctggagggt ggaacaccgg tggaagccgg tatcccgggc agggaagccc tggaggcaac    240
cgttacccac ctcagggtgg cacctggggg cagccccacg gtggtggctg ggacaaccc     300
catgggggca gctggggaca acctcatggt ggtagttggg gtcagcccca tggcggtgga    360
tggggccaag gaggggtac ccataatcag tggaacaagc ccagcaaacc aaaaaccaac     420
ctcaagcatg tggcaggggc tgcggcagct ggggcagtag tggggggcct tggtggctac    480
atgctgggga gcgccgtgag caggcccatg atccattttg gcaacgactg ggaggaccgc    540
tactaccgtg aaaacatgta ccgctaccct aaccaagtgt actacaggcc agtggatcag    600
tacagcaacc agaacaactt cgtgcacgac tgcgtcaata tcaccatcaa gcagcacacg    660
gtcaccacca ccaccaaggg ggagaacttc accgagaccg atgtgaagat gatggagcgc    720
gtggtggagc agatgtgcgt cacccagtac cagaaggagt cccaggccta ttacgacggg    780
agaagatcca gcagcaccgt gcttttctcc tcccctcctg tcatcctcct catctccttc    840
ctcatcttcc tgatcgtggg atgagggagg ccttcctgct tgttccttcg cattctcgtg    900
gtctaggctg ggggaggggt tatccacctg tagctctttc aattgaggtg ttctcattc     960
ttgcttctct gtgtccccca taggctaata cccctggcac tgatgggccc tgggaaatgt   1020
acagtagacc agttgctctt tgcttccaggt cccttttgatg gagtctgtca tcagccagtg  1080
ctaacaccgg gccaataaga atataacacc aaataactgc tggctagttg ggctttgtt    1140
```

```
ttggtctagt gaataaatac tggtgtatcc cctgacttgt acccagagta caaggtgaca    1200
gtgacacatg taacttagca taggcaaagg gttctacaac caaagaagcc actgtttggg    1260
gatggcgccc tggaaaacag cctcccacct gggatagcta gagcatccac acgtggaatt    1320 cttctttac taacaaacga tagctgattg aaggcaacaa aaaaaaaaaa atcaaattgt     1380
cctactgacg ttgaaagcaa acctttgttc attcccaggg cactagaatg atctttagcc    1440
ttgcttggat tgaactagga gatcttgact ctgaggagag ccagccctgt aaaaagcttg    1500
gtcctcctgt gacgggaggg atggttaagg tacaaaggct agaaacttga gtttcttcat    1560
ttctgtctca caattatcaa aagctagaat tagcttctgc cctatgtttc tgtacttcta    1620
tttgaactgg ataacagaga gacaatctaa acattctctt aggctgcaga taagagaagt    1680
aggctccatt ccaaagtggg aaagaaattc tgctagcatt gtttaaatca ggcaaaattt    1740
gttcctgaag ttgcttttta ccccagcaga cataaactgc gatagcttca gcttgcactg    1800
tggattttct gtatagaata tataaaacat aacttcaagc ttatgtcttc tttttaaaac    1860
atctgaagta tgggacgccc tggccgttcc atccagtact aaatgcttac cgtgtgaccc    1920
ttgggctttc agcgtgcact cagttccgta ggattccaaa gcagacccct agctggtctt    1980
tgaatctgca tgtacttcac gttttctata tttgtaactt tgcatgtatt ttgttttgtc    2040
atataaaaag tttataaatg tttgctatca gactgacatt aaatagaagc tatgatg       2097
```

<210> SEQ ID NO 6
<211> LENGTH: 254
<212> TYPE: PRT
<213> ORGANISM: Mus musculus

<400> SEQUENCE: 6

```
Met Ala Asn Leu Gly Tyr Trp Leu Leu Ala Leu Phe Val Thr Met Trp
1               5                   10                  15

Thr Asp Val Gly Leu Cys Lys Lys Arg Pro Lys Pro Gly Gly Trp Asn
            20                  25                  30

Thr Gly Gly Ser Arg Tyr Pro Gly Gln Gly Ser Pro Gly Gly Asn Arg
        35                  40                  45

Tyr Pro Pro Gln Gly Gly Thr Trp Gly Gln Pro His Gly Gly Gly Trp
    50                  55                  60

Gly Gln Pro His Gly Gly Ser Trp Gly Gln Pro His Gly Gly Ser Trp
65                  70                  75                  80

Gly Gln Pro His Gly Gly Gly Trp Gly Gln Gly Gly Thr His Asn
                85                  90                  95

Gln Trp Asn Lys Pro Ser Lys Pro Lys Thr Asn Leu Lys His Val Ala
            100                 105                 110

Gly Ala Ala Ala Ala Gly Ala Val Val Gly Gly Leu Gly Gly Tyr Met
        115                 120                 125

Leu Gly Ser Ala Met Ser Arg Pro Met Ile His Phe Gly Asn Asp Trp
    130                 135                 140

Glu Asp Arg Tyr Tyr Arg Glu Asn Met Tyr Arg Tyr Pro Asn Gln Val
145                 150                 155                 160

Tyr Tyr Arg Pro Val Asp Gln Tyr Ser Asn Gln Asn Asn Phe Val His
                165                 170                 175

Asp Cys Val Asn Ile Thr Ile Lys Gln His Thr Val Thr Thr Thr Thr
            180                 185                 190

Lys Gly Glu Asn Phe Thr Glu Thr Asp Val Lys Met Met Glu Arg Val
        195                 200                 205
```

```
Val Glu Gln Met Cys Val Thr Gln Tyr Gln Lys Glu Ser Gln Ala Tyr
        210                 215                 220

Tyr Asp Gly Arg Arg Ser Ser Thr Val Leu Phe Ser Pro Pro
225                 230                 235                 240

Val Ile Leu Leu Ile Ser Phe Leu Ile Phe Leu Ile Val Gly
                245                 250
```

<210> SEQ ID NO 7
<211> LENGTH: 15
<212> TYPE: PRT
<213> ORGANISM: Artificial Sequence
<220> FEATURE:
<223> OTHER INFORMATION: Synthetic Peptide Linker

<400> SEQUENCE: 7

```
Gly Gly Gly Gly Ser Gly Gly Gly Gly Ser Gly Gly Gly Gly Ser
1               5                   10                  15
```

<210> SEQ ID NO 8
<211> LENGTH: 10
<212> TYPE: PRT
<213> ORGANISM: Artificial Sequence
<220> FEATURE:
<223> OTHER INFORMATION: Synthetic Peptide Linker

<400> SEQUENCE: 8

```
Gly Gly Gly Gly Ser Gly Gly Gly Gly Ser
1               5                   10
```

<210> SEQ ID NO 9
<211> LENGTH: 15
<212> TYPE: PRT
<213> ORGANISM: Artificial Sequence
<220> FEATURE:
<223> OTHER INFORMATION: Synthetic Peptide Linker

<400> SEQUENCE: 9

```
Glu Ser Gly Arg Ser Gly Gly Gly Ser Gly Gly Gly Gly Ser
1               5                   10                  15
```

<210> SEQ ID NO 10
<211> LENGTH: 14
<212> TYPE: PRT
<213> ORGANISM: Artificial Sequence
<220> FEATURE:
<223> OTHER INFORMATION: Synthetic Peptide Linker

<400> SEQUENCE: 10

```
Glu Gly Lys Ser Ser Gly Ser Gly Ser Glu Ser Lys Ser Thr
1               5                   10
```

<210> SEQ ID NO 11
<211> LENGTH: 15
<212> TYPE: PRT
<213> ORGANISM: Artificial Sequence
<220> FEATURE:
<223> OTHER INFORMATION: Synthetic Peptide Linker

<400> SEQUENCE: 11

```
Glu Gly Lys Ser Ser Gly Ser Gly Ser Glu Ser Lys Ser Thr Gln
1               5                   10                  15
```

<210> SEQ ID NO 12
<211> LENGTH: 14
<212> TYPE: PRT

```
<213> ORGANISM: Artificial Sequence
<220> FEATURE:
<223> OTHER INFORMATION: Synthetic Peptide Linker

<400> SEQUENCE: 12

Glu Gly Lys Ser Ser Gly Ser Gly Ser Glu Ser Lys Val Asp
1               5                   10

<210> SEQ ID NO 13
<211> LENGTH: 14
<212> TYPE: PRT
<213> ORGANISM: Artificial Sequence
<220> FEATURE:
<223> OTHER INFORMATION: Synthetic Peptide Linker

<400> SEQUENCE: 13

Gly Ser Thr Ser Gly Ser Gly Lys Ser Ser Glu Gly Lys Gly
1               5                   10

<210> SEQ ID NO 14
<211> LENGTH: 18
<212> TYPE: PRT
<213> ORGANISM: Artificial Sequence
<220> FEATURE:
<223> OTHER INFORMATION: Synthetic Peptide Linker

<400> SEQUENCE: 14

Lys Glu Ser Gly Ser Val Ser Ser Glu Gln Leu Ala Gln Phe Arg Ser
1               5                   10                  15

Leu Asp

<210> SEQ ID NO 15
<211> LENGTH: 16
<212> TYPE: PRT
<213> ORGANISM: Artificial Sequence
<220> FEATURE:
<223> OTHER INFORMATION: Synthetic Peptide Linker

<400> SEQUENCE: 15

Glu Ser Gly Ser Val Ser Ser Glu Glu Leu Ala Phe Arg Ser Leu Asp
1               5                   10                  15

<210> SEQ ID NO 16
<211> LENGTH: 200
<212> TYPE: DNA
<213> ORGANISM: Artificial Sequence
<220> FEATURE:
<223> OTHER INFORMATION: Synthetic general structure for an
      oligonucleotide used in preparation of siRNA molecule
<220> FEATURE:
<221> NAME/KEY: misc_feature
<222> LOCATION: (1)..(200)
<223> OTHER INFORMATION: n is a, g, c, t, or u
<220> FEATURE:
<221> NAME/KEY: misc_feature
<222> LOCATION: (2)..(200)
<223> OTHER INFORMATION: nucleotide may be missing

<400> SEQUENCE: 16
nnnnnnnnnn nnnnnnnnnn nnnnnnnnnn nnnnnnnnnn nnnnnnnnnn nnnnnnnnnn      60
nnnnnnnnnn nnnnnnnnnn nnnnnnnnnn nnnnnnnnnn nnnnnnnnnn nnnnnnnnnn     120
nnnnnnnnnn nnnnnnnnnn nnnnnnnnnn nnnnnnnnnn nnnnnnnnnn nnnnnnnnnn     180
nnnnnnnnnn nnnnnnnnnn                                                 200

<210> SEQ ID NO 17
```

```
<211> LENGTH: 200
<212> TYPE: DNA
<213> ORGANISM: Artificial Sequence
<220> FEATURE:
<223> OTHER INFORMATION: Synthetic general structure for an
      oligonucleotide used in preparation of siRNA molecule
<220> FEATURE:
<221> NAME/KEY: misc_feature
<222> LOCATION: (1)..(200)
<223> OTHER INFORMATION: n is a, g, c, t, or u
<220> FEATURE:
<221> NAME/KEY: misc_feature
<222> LOCATION: (2)..(200)
<223> OTHER INFORMATION: nucleotide may be missing

<400> SEQUENCE: 17
nnnnnnnnnn nnnnnnnnnn nnnnnnnnnn nnnnnnnnnn nnnnnnnnnn nnnnnnnnnn      60
nnnnnnnnnn nnnnnnnnnn nnnnnnnnnn nnnnnnnnnn nnnnnnnnnn nnnnnnnnnn     120
nnnnnnnnnn nnnnnnnnnn nnnnnnnnnn nnnnnnnnnn nnnnnnnnnn nnnnnnnnnn     180
nnnnnnnnnn nnnnnnnnnn                                                 200

<210> SEQ ID NO 18
<211> LENGTH: 42
<212> TYPE: PRT
<213> ORGANISM: Artificial Sequence
<220> FEATURE:
<223> OTHER INFORMATION: Synthetic biotin-tagged amyloid-beta peptide

<400> SEQUENCE: 18

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40
```